US012611487B2

(12) United States Patent
Zimmermann et al.

(10) Patent No.: US 12,611,487 B2
(45) Date of Patent: Apr. 28, 2026

(54) MULTILAYER ENGINEERED HEART MUSCLE

(71) Applicant: Georg-August-Universität Göttingen Stiftung Öffentlichen Rechts, Universitätsmedizin, Göttingen (DE)

(72) Inventors: Wolfram-Hubertus Zimmermann, Göttingen (DE); Malte Tiburcy, Göttingen (DE); Tim Meyer, Göttingen (DE)

(73) Assignee: GEORG-AUGUST-UNIVERSITÄT GÖTTINGEN STIFTUNG ÖFFENTLICHEN RECHTS, UNIVERSITÄTSMEDIZIN, Göttingen (DE)

( * ) Notice: Subject to any disclaimer, the term of this patent is extended or adjusted under 35 U.S.C. 154(b) by 268 days.

(21) Appl. No.: 18/031,805

(22) PCT Filed: Oct. 21, 2021

(86) PCT No.: PCT/EP2021/079164
§ 371 (c)(1),
(2) Date: Apr. 13, 2023

(87) PCT Pub. No.: WO2022/084429
PCT Pub. Date: Apr. 28, 2022

(65) Prior Publication Data
US 2023/0390460 A1 Dec. 7, 2023

(30) Foreign Application Priority Data
Oct. 22, 2020 (EP) .................................... 20203316

(51) Int. Cl.
*A61L 27/38* (2006.01)
*A61L 27/52* (2006.01)

(52) U.S. Cl.
CPC ....... *A61L 27/3895* (2013.01); *A61L 27/3886* (2013.01); *A61L 27/52* (2013.01); *A61L 2430/20* (2013.01)

(58) Field of Classification Search
CPC .................................................. A61L 27/3895
See application file for complete search history.

(56) References Cited

U.S. PATENT DOCUMENTS

| | | | |
|---|---|---|---|
| 4,738,740 A | 4/1988 | Pinchuk et al. | |
| 2010/0167373 A1* | 7/2010 | Zimmermann | A61L 27/38 |
| | | | 435/174 |
| 2015/0164784 A1 | 6/2015 | Zimmerman et al. | |
| 2018/0015029 A1 | 1/2018 | Zimmerman et al. | |
| 2019/0106663 A1 | 4/2019 | Meyer et al. | |

FOREIGN PATENT DOCUMENTS

| | | |
|---|---|---|
| EP | 2 099 508 B1 | 9/2009 |
| EP | 2 842 581 A1 | 3/2015 |
| EP | 2 840 132 B1 | 11/2016 |
| EP | 3 945 133 A1 | 2/2022 |
| JP | 2003-508130 A | 3/2003 |
| JP | 2011-130995 A | 7/2011 |
| WO | 01/15754 A1 | 3/2001 |
| WO | 2007/054286 A1 | 5/2007 |
| WO | 2008/058917 A1 | 5/2008 |
| WO | 2015/025030 A1 | 2/2015 |
| WO | 2015/040142 A1 | 3/2015 |
| WO | 2017/207431 A1 | 12/2017 |
| WO | 2020/012033 A1 | 1/2020 |

OTHER PUBLICATIONS

Bao et al. "Long-term self-renewing human epicardial cells generated from pluripotent stem cells under defined xeno-free conditions," *Nat Biomed Eng.* (2016).
Bao et al. "Directed differentiation and long-term maintenance of epicardial cells derived from human pluripotent stem cells under fully defined conditions," *Nat Protoc.* Sep.;12(9): 1890-1900 (2017).
Brewer et al., "Optimized Survival of Hippocampal neurons in B27-Supplemented Neurobasal™, a New Serum-Free Medium Combination," *J. Neurosci. Res.*, 35: 567-576 (1993).
Fujita et al., "Variation in left ventricular regional wall stress with cine magnetic resonance imaging: normal subjects versus dilated cardiomyopathy," *Am Heart J.* 125: 1337-45 (1993).
Hanses et al., "Intronic CRISPR Repair in a Preclinical Model of Noonan Syndrome-Associated Cardiomyopathy," *Circulation* (2020).
Hesse et al., "Lights on for HIF-1α: Genetically Enhanced Mouse Cardiomyocytes for Heart Tissue Imaging," *Cell Physiol Biochem.* 34:455-462 (2014).
Hynes et al., "Overview of the Matrisome—An Inventory of Extracellular Matrix Constituents and Functions," *Cold Spring Harb Perspect Biol.* 4(1):a004903 (2012).
Ieda et al., "Direct Reprogramming of Fibroblasts into Functional Cardiomyocytes by Defined Factors," *Cell* 142(3):375-86 (2010).
Iyer et al., "Robust derivation of epicardium and its differentiated smooth muscle cell progeny from human pluripotent stem cells," *Development.* 142(8): 1528-41 (2015).
Iyer et al., "Synthetic Oxygen Carriers in Cardiac Tissue Engineering," *Artif Cells Blood Substit Immobil Biotechnol.* 35(1): 135-48 (2007).

(Continued)

*Primary Examiner* — Amy L Clark
(74) *Attorney, Agent, or Firm* — GREENBLUM & BERNSTEIN, P.L.C.

(57) ABSTRACT

A method for manufacturing a multilayer engineered heart muscle that includes (i) providing a liquid reconstitution mixture in a mould and (ii) culturing the mixture. The method includes a sequential addition of one or more further liquid reconstitution mixtures to obtain a multilayer engineered heart muscle. The muscle ideally has the form of a patch, a pouch, or a cylinder. Furthermore, a multilayer engineered heart muscle having collagen, cardiac myocytes and non-myocytes originating from at least 2 layers is disclosed. The multilayer engineered heart muscle forms the basis for several in vitro and in vivo applications such as the production of a multilayer engineered heart muscle for use in a patient, for example for use in heart repair.

14 Claims, 11 Drawing Sheets

(56) References Cited

OTHER PUBLICATIONS

Kawel et al., "Normal Left Ventricular Myocardial Thickness for Middle-Aged and Older Subjects with Steady-State Free Precession Cardiac Magnetic Resonance: The Multi-Ethnic Study of Atherosclerosis," *Circ Cardiovasc Imaging.* Jul.;5(4): 500-8. (2012).

Kensah et al., "Murine and human pluripotent stem cell-derived cardiac bodies form contractile myocardial tissue in vitro," *Eur Heart J* 34, 1134-114 (2013).

Mills et al., "Drug Screening in Human PSC-Cardiac Organoids Identifies Pro-proliferative Compounds Acting via the Mevalonate Pathway," *Cell Stem Cell* 24, 895-907 e896 (2019).

Mouw et al., "Extracellular matrix assembly: a multiscale deconstruction," *Nat Rev Mol Cell Biol.* 15(12):771-785. doi: 10.1038/nrm3902 (2014).

Mulieri et al., "Altered Myocardial Force-Frequency Relation in Human Heart Failure," *Circulation.* 85(5): 1743-50 (1992).

Nam et al., "Reprogramming of human fibroblasts toward a cardiac fate," *Proc Natl Acad Sci USA* 110(14): 5588-93 (2013).

Nowosielski et al., "Comparison of wall thickening and ejection fraction by cardiovascular magnetic resonance and echocardiography in acute myocardial infarction," *J Cardiovasc Magn Reson.* 11(1):22 (2009).

Naito et al., "Optimizing Engineered Heart Tissue for Therapeutic Applications as Surrogate Heart Muscle," *Circulation* 114, 172-7 (2006).

O'Leary et al., Multi-hierarchical self-assembly of a collagen mimetic peptide from triple helix to nanofibre and hydrogel, *Nat Chem.* 3(10):821-8. doi: 10.1038/nchem.ll23. PMID: 21941256 (2011).

Pislaru et al., "Viscoelastic properties of normal and infarcted myocardium measured by a multifrequency shear wave method: comparison with pressure-segment length method," *Ultrasound Med Biol.* 40(8): 1785-95 (2014).

Radisic et al., "Mathematical model of oxygen distribution in engineered cardiac tissue with parallel channel array perfused with culture medium containing oxygen carriers," *Am J Physiol Heart Circ Physiol.* 288(3):H1278-89 (2005).

Riegler et al., "Human Engineered Heart Muscles Engraft and Survive Long Term in a Rodent Myocardial Infarction Model," *Circulation Research* 117, 720-730 (2015).

Ronaldson-Bouchard et al., "Advanced maturation of human cardiac tissue grown from pluripotent stem cells," *Nature* 556, 239-243 (2018).

Rump et al., "Fractional Encoding of Harmonic Motions in MR Elastography," *Magn. Reson. Med.,* 57: 388-395 (2007).

Schlick et al., "Agonistic and antagonistic roles of fibroblasts and cardiomyocytes on viscoelastic stiffening of engineered human myocardium," *Prog Biophys Mol Biol* 144:51-60 (2019).

Song et al., "Heart repair by reprogramming non-myocytes with cardiac transcription factors,". *Nature.* 485(7400): 599-604 (2012).

Soong et al., "Cardiac Differentiation of Human Embryonic Stem Cells and their Assembly into Engineered Heart Muscle," *Curr Protoc Cell Biol.* Chapter 23: Unit23.8 (2012).

Stoker et al., "Regional Differences in Capillary Density and Myocyte Size in the Normal Human Heart," *Anat Rec.* 202(2): 187-91 (1982).

Tulloch et al., "Growth of Engineered Human Myocardium with Mechanical Loading and Vascular Coculture," *Circ Res* 109(1):47-59 (2011).

Tiburcy et al., "Collagen-Based Engineered Heart Muscle," *Methods Mol Biol.* 1181:167-76. doi:10.1007/978-1-4939-1047-2_15. PMID: 25070336 (2014).

Tiburcy et al., "Defined Engineered Human Myocardium With Advanced Maturation for Applications in Heart Failure Modeling and Repair," *Circulation* 135, 1832-1847 (2017).

Tiburcy et al., "Generation of Engineered Human Myocardium in a Multi-well Format," *STAR Protocols* 1, 100032, (2020).

Wiegerinck et al., "Force Frequency Relationship of the Human Ventricle Increases During Early Postnatal Development," *Pediatr Res.* 65:414-419 (2009).

Weinberger et al., "Cardiac repair in guinea pigs with human engineered heart tissue from induced pluripotent stem cells," *Sci Transl Med* 8(363):363ra148 (2016).

Witty et al., "Generation of the epicardial lineage from human pluripotent stem cells," *Nat Biotechnol.* 32(10): 1026-1035 (2014).

Yildirim et al., "Development of a Biological Ventricular Assist Device: Preliminary Data From a Small Animal Model," *Circulation.* 116(11 Suppl):I16-23 (2007).

Zhang et al., "Tissue-engineered Cardiac Patch for Advanced Functional Maturation of Human ESC-derived Cardiomyocytes," *Biomaterials* 34, 5813-5820 (2013).

Zimmermann et al., "Engineered heart tissue grafts improve systolic and diastolic function in infarcted rat hearts," *Nat Med* 12(4):452-8 (2006).

International Search Report issued in PCT/EP2021/079164, dated Jan. 4, 2022.

Written Opinion of the International Searching Authority issued in PCT/EP2021/079164, dated Jan. 4, 2022.

Bian et al., "Controlling the Structural and Functional Anisotropy of Engineered Cardiac Tissues," *Biofabrication,* Jun. 2014, 6(2): 024109.

Brewer et al., "Neurobasal™ Medium/B27 Supplement: A New Serum-Free Medium For Survival of Neurons," *Focus* 16, No. 1, 1994.

Burridge et al., "Production of De Novo Cardiomyocytes: Human Pluripotent Stem Cell Differentiation and Direct Reprogramming," *Cell Stem Cell,* 10, Jan. 6, 2012.

Tiburcy, et al., "Terminal Differentiation, Advanced Organotypic Maturation, and Modeling of Hypertrophic Growth in Engineered Heart Tissue," *Circulation Research,* Oct. 28, 2011.

Zhang, J., "Engineered Tissue Patch for Cardiac Cell Therapy," *Curr Treat Options Cardiovasc Med.,* Aug. 2015; 17(8): 399.

Zimmerman, et al., "Three-Dimensional Engineered Heart Tissue from Neonatal Rat Cardiac Myocytes," *Biotechnology and Bioengineering,* vol. 68, No. 1, Apr. 5, 2000.

Office Action dated Nov. 22, 2025, issued in Chinese patent application No. 202180083433.6, with English translation thereof.

"Trauma Fundamentals", edited by Fu Xiaobing and Wang Zhengguo, Hubei Science and Technology Press, published on Nov. 30, 2016, pp. 362-363.

\* cited by examiner

180 µl
EHM in
loop
format

450 µl
EHM
loop
format 2 ml
EHM as
patch 8 ml
EHM as patch 1 cm

Luminescence 6.0    4.0    2.0

A

B

A

B          1 h

C          24 h

D          18 d

A

B

Field stimulation
field strength ~2 V/cm

Point stimulation via
co-axial electrode

A

B

C

15

⌀0.9mm

17

⌀1.1mm

No gradient

Vertical gradient

⌀0.7mm

D upper part lower part

Left bars: upper part
Right bars: lower part

FAC (%)

1.5

1.0

0.5

0.0

No gradient          Vertical gradient
                     P<0.05

A

Perforating Pole

3 Layers

Inlet to flexible
balloon 3.5 mm
interpole
distance 1.5 mm pole
diameter

B  Cylinder with radial inward poles   Cylinder with radial outward poles

Rotation to facilitate layering

Optimally porous cylinder to support layering in outside pole design

Outer wall

Cylinder with radial outward poles

Layer 1

Layer 2

Layer 3

Outer wall

C1

Top view

Projection side view

Bottom Layer     Middle Layer     Top Layer

C2

Top view

Projection side view

Bottom Layer          Middle Layer          Top Layer

MULTILAYER ENGINEERED HEART MUSCLE

BACKGROUND OF THE INVENTION

Regenerating a failing heart remains a huge challenge. A common cause of heart failure is a heart attack. A heart attack, or myocardial infarction, is caused by a block of arterial blood flow leading to underperfused tissue that is consequently deprived from oxygen and nutrients. During a heart attack, millions or even up to a billion of cells undergo rapid necrosis, which is leading cause of a reduced heart performance and in clinical terms heart failure. As the heart is largely post-mitotic tissue, the heart tissue cannot regenerate on its own. Implantation of an engineered heart muscle is a sought for goal in the field. Different engineered heart muscle formats have been developed for application in disease modelling, drug screening, and heart repair. The inventors and others have published several applications of engineered human myocardium models for in vitro studies of cardiomyocyte maturation and hypertrophy (Tiburcy et al. 2017), disease modelling (Hanses et al., 2020) and drug screening (Mills et al. 2019) as well as in vivo heart repair (Riegler et al. 2015).

One approach to support cardiomyocyte self-assembly into 3D tissue is a scaffold-containing approach, wherein the scaffold is mainly supported by either collagen or fibrin (Zimmermann et al. 2006, Tulloch et al. 2011, Soong et al. 2012, Zhang et al. 2013, Riegler et al. 2015, Weinberger et al. 2016, Tiburcy et al. 2017). Furthermore, non-myocytes are essential for the generation of a 3D tissue. Similar as in rodent models (Naito et al. 2006), said non-myocytes are mainly fibroblasts or stromal cells with fibroblast-activity (Kensah et al. 2013; Ronaldson-Bouchard et al. 2018; Tiburcy et al. 2017, Zhang et al. 2013).

In addition to the cellular components and the scaffold, the highest degree of maturation has been achieved under support by biophysical stimuli, i.e. either mechanical, electrical or a combination of both (Ronaldson-Bouchard et al. 2018; Tiburcy et al. 2017). Mechanical loading is an absolute requirement for the engineering of heart muscle with advanced maturation.

For the production of artificial heart muscle tissue for the treatment of patients with heart muscle weakness, an engineered heart muscle needs to support the force of a beating human heart. The cardiac wall to be treated is typically 5-10 mm thick in the patient (Kawel et al. 2012), i.e. an implant must ideally reach this thickness and must also be able to develop mechanical force to support cardiac wall function.

A key challenge when trying to obtain an engineered heart muscle of such a thickness is the oxygen and nutrient supply of the cells embedded in the engineered heart muscle at all times. Thus, there is a need in the art for an engineered heart muscle with an adequate thickness to support a human heart. The inventors have overcome this challenge by a repetitive and sequential casting process of the engineered heart muscle.

SUMMARY OF THE INVENTION

To generate a multilayer engineered heart muscle (MEHM), a compacted layer (reconstitution mixture) of a cell-containing hydrogel is coated by at least one other layer. This repetitive and sequential process ensures the formation of a thickened and enforced engineered heart muscle, wherein at least one new layer merges to the previous layer(s). Put differently, an engineered heart muscle is expanded in thickness by repetitive and sequential layering. Furthermore, it is important that the engineered heart muscle is penetrated by a mechanical support, wherein poles extend through the engineered tissue in order to support auxotonic contractions and introduce channels for oxygen and nutrient supply throughout the engineered tissue.

One particular advantage of the method as disclosed herein is that the cells within reconstitution mixture/MEHM are sufficiently supplied with nutrients and oxygen at all times. Sufficient oxygen and nutrient supply is achieved by keeping the overall diffusion distance from the MEHM surface to the core (center) of the MEHM minimal at all times during the manufacturing process while still producing a thickened MEHM, which may for example be used as an implant. This is achieved by a perforated MEHM design. Perforations are for example introduced by the perforating poles used for inter alia mechanical support (as shown in e.g. FIGS. 7 and 8). The poles are capable of providing oxygen and/or nutrients to the cells in the MEHM. The poles create "channels" though the reconstitution mixture/MEHM for supply with oxygen and/or nutrients and independently introduce a mechanical load onto the MEHM.

To obtain such a thick MEHM, reconstitution mixtures comprising cardiomyocytes, non-cardiomyocytes and collagen are cast repetitively and sequentially. By repetitively casting individual layers on top of the previous layer and/or from the bottom of the previous layer, the layers merge, which is a key advantage of the disclosed method. By sequential casting, a layer has condensed at least by 20% of the original volume before a further layer is added. The embedded cells are supplied with oxygen and nutrients by diffusion from the tissue surface in order to avoid e.g. hypoxia and/or necrosis. The reconstitution mixtures are perforated by poles, which extends the tissue surface area. Thus, the overall thickness of the muscle can be scaled as desired while considering diffusion as well as cell specific oxygen and nutrient requirements.

In a first aspect, a method of manufacturing a multilayer engineered heart muscle (MEHM) is disclosed, wherein the method comprises the steps of:

(i) providing a liquid reconstitution mixture in a mould, wherein said reconstitution mixture is perforated by at least two poles,
wherein said reconstitution mixture comprises (a) collagen, (b) a cellular mixture of cardiac myocytes and non-myocytes and (c) a suitable reconstitution medium, whereby said reconstitution mixture undergoes gelation in the mould, (ii) culturing the mixture obtained by step (i) in said mould in a suitable culturing medium, whereby the reconstitution mixture compacts in the mould;

(iii) a) adding a further liquid reconstitution mixture as defined in step (i) from the top and/or from the bottom to the compacted reconstitution mixture obtained by step (ii) whereby said further liquid reconstitution mixture undergoes gelation, followed by culturing under the same conditions as in step ii), whereby said further reconstitution mixture compacts in the mould; or b) transferring the compacted reconstitution mixture obtained by step (ii) into a different mould, wherein said reconstitution mixture is perforated by at least two poles, followed by carrying out step (iii) a) in said different mould;

thereby obtaining a multilayer engineered heart muscle (MEHM), preferably wherein the MEHM is thickened by repeating step (iii)a) and/or step (iii)b) at least once, and (iv) optionally culturing the MEHM of step (iii) in said mould in a suitable maturating medium, wherein the MEHM is capable of contracting.

In another aspect, a multilayer engineered heart muscle (MEHM) obtained by a method as disclosed herein is contemplated.

Furthermore, a multilayer engineered heart muscle (MEHM) is described, wherein the MEHM comprises (a) collagen and (b) a cellular mixture of cardiac myocytes and non-myocytes, and wherein the EHM comprises at least 2 layers.

Moreover, an engineered heart muscle (EHM) is disclosed, preferably an engineered heart patch, engineered heart pouch, or engineered heart cylinder, wherein the EHM comprises (a) collagen, (b) a cellular mixture of cardiac myocytes and non-myocytes and wherein the EHM has a thickness of at least about 0.6 mm.

In addition, the present disclosure discloses a use of the MEHM obtained by the method as disclosed herein or the MEHM as disclosed herein in an in vitro manufacture of an engineered human myocardium.

Finally, a multilayer EHM obtained by the method as disclosed herein or the MEHM as disclosed herein for the use in medicine, in particular heart failure, is described.

DETAILED DESCRIPTION OF THE INVENTION

In a first aspect, a method of manufacturing a multilayer engineered heart muscle (MEHM) is disclosed, wherein the method comprises the steps of:

(i) providing a liquid reconstitution mixture in a mould, wherein said reconstitution mixture is perforated by at least two poles, wherein said reconstitution mixture comprises (a) collagen, (b) a cellular mixture of cardiac myocytes and non-myocytes and (c) a suitable reconstitution medium, whereby said reconstitution mixture undergoes gelation in the mould, (ii) culturing the mixture obtained by step (i) in said mould in a suitable culturing medium, whereby the reconstitution mixture compacts in the mould;

(iii) a) adding a further liquid reconstitution mixture as defined in step (i) from the top and/or from the bottom to the compacted reconstitution mixture obtained by step (ii) whereby said further liquid reconstitution mixture undergoes gelation, followed by culturing under the same conditions as in step ii), whereby said further reconstitution mixture compacts in the mould; or b) transferring the compacted reconstitution mixture obtained by step (ii) into a different mould, wherein said reconstitution mixture is perforated by at least two poles, followed by carrying out step (iii) a) in said different mould;

thereby obtaining a multilayer engineered heart muscle (MEHM), preferably wherein the MEHM is thickened by repeating step (iii)a) and/or step (iii)b) at least once, and (iv) optionally culturing the MEHM of step (iii) in said mould in a suitable maturating medium, wherein the MEHM is capable of contracting.

In general, an engineered heart muscle (EHM), as used herein, refers to an artificial heart muscle comprising cells and collagen, which is capable of contracting. Furthermore, a multilayer engineered heart muscle (MEHM) originates from at least 2 layers of engineered heart muscle (EHM). In order to manufacture a multilayer engineered heart muscle (MEHM), the layers are sequentially added. When a sequential layering occurs, a subsequent layer is added to an original (first) layer. The subsequent layer then merges to the original (first) layer. This process of layering may be repeated several times. In other words, a subsequent layer merges to the previously added layer. When carrying out the layering, the MEHM thickens layer-by-layer. The key advantage of this method is that a thickened MEHM is more stable and is able to sustain greater forces than a single-layer EHM. Furthermore, another key feature of the MEHM is that it is capable of contraction, similarly to a natural heart myocardium, preferably as further defined below. Ideally, such a multilayer engineered heart muscle is suitable for use as an implant such as a heart implant.

In an embodiment, the MEHM obtained by step (iii) and optionally step (iv) has the ability to contract, which can be assessed by visual inspection. Alternatively, the contraction of the MEHM can be determined by the capability of the reconstitution mixture of step (i) to form a force-generating engineered heart muscle (EHM) by carrying out steps (i), (ii) and optionally (iv), and wherein the engineered heart muscle (EHM) is capable of developing contractile forces of at least 0.05 mN force of contraction (FOC) as measured under standard isometric conditions in Supplementary FIG. 6C of Tiburcy et al. Circulation 135(19)1832-1847 (2017). More specifically, the contraction of the MEHM can further be determined by assessing in parallel the capability of the reconstitution mixture of step (i) to form a force-generating engineered human muscle in loop-format, as described in Tiburcy et al. Circulation 135(19)1832-1847 (2017), by carrying out steps (i), (ii) and (iv), and wherein the engineered heart muscle in loop-format generates at least 0.05 mN force of contraction (FOC), as measured in Supplementary FIG. 6C of Tiburcy et al. Circulation 135(19)1832-1847 (2017). In other words, the contraction of the MEHM can be determined by generating a EHM in loop-format in parallel to the MEHM. The advantage of such a parallel approach is that the EHM formation in loop format is well established (see e.g. Tiburcy et al. 2017 and 2020) and can be also performed in a 48-well format. Furthermore, the force of contraction can more conveniently be determined in a loop-format as the force between two poles is measured. Thus, the quality of the reconstitution mixture and the media can more easily be assessed in the well-established loop format. Furthermore, it is expected that a well developing EHM in loop format also ensures that the MEHM is provided in equal quality. Alternatively, force of contraction (FOC) in an MEHM may also be directly measured. For example, Zimmermann et al. (2000) describes the measurement of FOC in tissue. Thus, the skilled person can also adapt said setup for the measurement of an FOC in an MEHM. In a preferred embodiment, the MEHM generates a force of contraction (FOC) of at least 0.05 mN, more preferably at least 0.1 mN, more preferably at least 0.3 mN, more preferably at least 0.5 mN, more preferably at least 1 mN, more preferably at least 3 mN, even more preferably at least 5 mN, and most preferably at least 10 mN.

In another preferred embodiment, each layer of the MEHM has a thickness of at least about mm, preferably of at least about 0.15 mm, more preferably of at least about 0.2 mm, more preferably of at least about 0.25 mm, more preferably of at least about 0.3 mm, more preferably of at least about 0.4 mm, and most more preferably of least about 0.5 mm. In an especially preferred embodiment the MEHM is from about 0.2 mm to about 30 mm in thickness, preferably from about 0.3 mm to about 30 mm, preferably from about 0.5 mm to about 30 mm in thickness, more preferably from about 0.7 mm to about 25 mm, more preferably from about 0.9 mm to about 23 mm, more preferably from about 1.5 mm to about 20 mm, more preferably from about 2 mm to about 18 mm, more preferably from about 2.8 mm to about 15 mm, more preferably from about 3.3 mm to about 13 mm, more preferably from about 3.8 mm to about 12 mm, more preferably from about 4.2 mm to about 11 mm, more preferably from about 4.6 mm to about 10.5 mm, and most preferably from about 5 mm to about 10 mm. The term "about" herein when used with reference to the thickness of both an individual layer of an multilayer engineered heart muscle of the invention and the thickness of an engineered heart muscle as described herein means that the thickness can deviate from the respective numerical value by ±1%, ±2%, ±3%, ±4%, ±5%, ±6%, ±7%, ±8%, ±9%, or ±10%. This means, for example, if the thickness of an individual layer is "about 0.3 mm", this layer can have a thickness ranging from 0.27 mm (a deviation of −10%) to 0.33 mm (a deviation of +10%). Likewise, if the engineered heart muscle as such has a thickness of about 0.8 mm, the engineered heart muscle includes a thickness ranging from 0.72 mm to 0.88 mm.

Ideally, the MEHM matches the thickness of a human myocardium, which is from 5 to 12 mm in thickness in a non-contracted state. For example, Kawel et al. 2012 published that the human heart wall is at most 12 mm at maximal relaxation. Nowosielski et al. 2009 published that the wall thickness typically increases by 60% upon contraction. Thus, it is estimated that a human heart has a maximal thickness of 20 mm. Consequently, an MEHM for use as a heart implant preferably has a thickness between 5 mm and 20 mm.

To the inventor's knowledge, this is the first thickened EHM design in the art. The key advantage of the disclosed method is that the MEHM originates from at least 2 layers, which are merged together. By this sequential and repetitive layering, the MEHM thickens layer-by-layer, while at the same time ensuring that the overall surface-tissue diffusion distance is minimal throughout the MEHM. The desired surface-tissue diffusion distance is ensured by the perforating pole design and density. A minimal or metabolically adequate surface-tissue diffusion ensures that the cells are supplied with oxygen and nutrients at all times. A reconstitution mixture or multilayered tissue thereof without perforations of e.g. several centimeters would exhibit rapid (tissue core) necrosis of the cells in the middle of the reconstitution mixture as said cells in the tissue core would not be supplied with sufficient oxygen and/or nutrients.

In another embodiment, the contraction of the MEHM can also be measured video-optically. For example, the fractional area change (FAC) of the MEHM can be measured. The method of assessing the FAC has been previously described in Tiburcy et al. (2017). Briefly, the area of the MEHM in a relaxed state and the contracted state is compared and the change is reported in percent. In an especially preferred embodiment, the contraction is determined by fractional area change (FAC) measurements of the MEHM using the method described in Tiburcy et al., Circulation 135(19)1832-1847 (2017), and wherein the fractional area change (FAC) is at least 0.5% upon electrical stimulation, preferably wherein the FAC is at least more preferably at least 1%, more preferably at least 2%, more preferably at least 3%, and even more preferably at least 5%. In an especially preferred embodiment, the FAC is at most 20%, preferably at most 19%, more preferably at most 18%, even more preferably at most 17%, even more preferably at most 16%, and even more preferably at most 15%. Electrical stimulation may be achieved by an electrical field or by point stimulation. Examples for an electrical field are shown in Example 4. Point stimulation with an electrode is also known to the skilled person. In general, electrical stimulation will lead to a contraction of the MEHM. It can be derived from Tiburcy et al. 2017, that around 7% FAC correspond to around 1 mN FOC (Supplementary FIG. 11). Based on this Figure, the skilled person is able to correlate FOC and FAC, if desired.

In order to manufacture such a MEHM, a liquid reconstitution mixture is provided in a mould. In general, a 'liquid' mixture is able to flow and fill out a mould. Furthermore, medium can be dissolved into the liquid reconstitution mixture. As used here, a 'liquid' mixture is meant in contrast to a 'gel-like' mixture, since a gel-like mixture is not able to flow and medium cannot be freely dissolved into a gel-like mixture and is defined as below.

A 'reconstitution mixture', as used herein, comprises collagen, a cellular mixture and a suitable reconstitution medium, wherein the cellular mixture is made up from cardiac myocytes and non-myocytes. The skilled person readily understands that the reconstitution mixture forms the basis of the MEHM, as the different components of the reconstitution mixture build up the key parts of the engineered heart muscle, i.e. reconstituting the key parts of a heart muscles in order to tissue-engineer a MEHM.

Collagen is one of the components of the reconstitution mixture. Collagen is the main structural protein in the extracellular matrix in various connective tissues in the body. Collagen consists of amino acids to form a triple helix of elongated fibrils, which is known to the skilled person. Furthermore, collagen support engineered tissues such as the MEHM and give the cells a structural support from the outside. The skilled person is also aware that collagen can be purchased from various vendors, such as 'Collagen Solutions'. For example, the reconstitution mixture may provide a final concentration of 0.5 and 3 mg/ml collagen, preferably between 0.55 and 2.5 mg/ml collagen, more preferably between 0.6 and 2.2 mg/ml collagen 0.65 and 2 mg/ml collagen, more preferably between 0.7 and 1.75 mg/ml collagen, more preferably between 0.75 and 1.5 mg/ml collagen, more preferably between 0.8 and 1.2 mg/ml collagen, even more preferably between 0.85 and 1 mg/ml collagen and most preferably about 0.9 mg/ml collagen. In a preferred embodiment, the collagen of step (i) is selected from the group consisting of collagen type I, collagen type III, collagen type IV, collagen type V, collagen type VI, collagen type XII, collagen type XIII, collagen type XIV, collagen type XV, and a mixture thereof. The skilled person knowns that type I collagen is the most abundant collagen in the human body. In a particularly preferred embodiment, at least 90% of the collagen of the reconstitution mixture of step (i) is collagen type I. Particularly if the MEHM is used as an implant, the collagen of the reconstitution mixture of step (i) may be of medical grade.

Of course, the collagen can be derived from various sources and various vendors. For example, the collagen can be of bovine origin, equine origin, human origin, or marine origin. In an especially preferred embodiment, the collagen is of bovine origin. In an especially preferred embodiment the collagen used is free of porcine endogenous retrovirus and any transmissible spongiform encephalopathies. It is also contemplated that the collagen in the reconstitution mixture of step (i) further comprises one or more additional extracellular matrix component other than collagen. The term "extracellular matrix protein" refers to any extracellular matrix (ECM) protein known by the person of average skill (Hynes and Naba (2012)). Furthermore, the skilled person is aware of the composition of extracellular matrices from e.g. Mouw J K, et al. (2014), which can be used for the generation of an EHM. In an especially preferred embodiment, said one or more additional matrix components is selected from the group consisting of elastin, laminin, entactin, nidogen, proteoglycans (e.g. decorin), glycosaminoglycans (e.g. hyaluronic acid), and fibronectin. Furthermore, the skilled person is aware that there are synthetic mimetics of said extracellular proteins commercially available and that said synthetic mimetics are also suitable for the manufacture of a MEHM. For example, the skilled person is aware of literature such as O'Leary et al. (2011), which describes the self-assembly of a collagen mimetic peptide from triple helix to nanofibre and hydrogel.

In a preferred embodiment, the cellular mixture in step (i) provides a final cell concentration in the reconstruction mixture of $1-26.5\times10^6$ cells per ml, preferably of $2-13.2\times10^6$ cells per ml, more preferably of $3-10\times10^6$ cells per ml, more preferably of $3.5-9\times10^6$ cells per ml, more preferably of $4-8\times10^6$ cells per ml, more preferably of $4.3-7\times10^6$ cells per ml, more preferably of $4.6-6\times10^6$ cells per ml, even more preferably of about $5\times10^6$ cells per ml. However, the skilled person is able to determine a suitable concentration of cells in the reconstitution mixture. The skilled person may for example be guided to determine a suitable cell concentration and composition by Tiburcy et al. (2017) or Schlick et al. (2019).

The cellular mixture is made up from cardiac myocytes and non-myocytes. Cardiac myocytes are the muscle cells (myocytes) that make up the cardiac muscle (heart muscle) in natural tissue. Each cardiac myocyte contains myofibrils, which are specialized organelles consisting of long chains of sarcomeres—the fundamental contractile units of muscle cells. The skilled person is aware that cardiac myocytes can be obtained commercially or by differentiation from pluripotent stem cells, e.g. from induced pluripotent stem cells. In a particularly preferred embodiment, the cardiac myocytes are human cardiac myocytes. In another particularly preferred embodiment, the cardiac myocytes are derived from embryonic stem cells, wherein the cells are not produced using a process which involves modifying the germ line genetic identity of human beings or which involves the use of a human embryo for industrial or commercial purposes. For example, the cardiac myocytes can be derived from induced pluripotent stem cells, parthenogenetic stem cells, programmed somatic cells or adult stem cells, preferably wherein the cardiac myocytes are derived from induced pluripotent stem cells. The skilled person is aware of induced pluripotent stem cells, parthenogenetic stem cells, or adult stem cells, as described in the art. Programmed somatic cells are directly re-programmed into a desired cell type. This method avoids the induction of pluripotency and subsequent differentiation procedures (see for example Ieda et al. 2010, Song et al. 2012, Nam et al. 2013). In particular, the skilled person is aware of various protocols in the literature, which describe the generation of cardiac myocytes such as by serum-free differentiation as described in WO2015/040142 or alternative protocols such as reviewed in Burridge et al. (2012), Production of de novo cardiomyocytes: human pluripotent stem cell differentiation and direct reprogramming, Cell Stem Cell. 2012 Jan. 6; 10(1):16-28. In addition, the book chapter *Engineered Heart Muscle Models in Phenotypic Drug Screens* of Zimmermann in the book of Schäfer-Korting_Stucchi Maria-Engler, Landsiedel (87017223) Organotypic Models in Drug Development, Handbook of Experimental Pharmacology (Springer, 2020) summarizes various protocols in order to obtain cardiac myocytes, which can be used for the method as disclosed herein. In said protocols, it is also contemplated that the cardiac myocytes can be non-human primate stem cell-derived, fetal, or neonatal cardiac myocytes. The skilled person is also aware of methods to assess the identity of cardiac myocytes such as by flow cytometry or RNA-sequencing. Said methods for example allow to determine the expression of the markers ACTN2, RYR2, and/or troponins, which are characteristic for cardiac myocytes.

In an embodiment the cellular mixture of step (i) comprises at least 10% cardiac myocytes, preferably at least 20%, more preferably at least 30%, even more preferably at least 40%, and most preferably at least 50%. The skilled person is able to determine the optimal ratio of cardiomyocytes and non-myocytes. The optimization of the optimal ratio will be guided by a compaction of the EHM and in particular of the ability of the EHM to contract. For example, Tiburcy et al. (2017) and Schlick et al. (2019) demonstrate that cardiomyocytes and non-myocytes such as stromal cells are required for engineered human myocardium contraction and compaction. Specifically, the cardiomyocytes are causing the contraction, while the non-myocytes such as stromal cells, cause the compaction. Furthermore, the non-myocytes excrete extracellular matrix proteins such as collagens in order to support the three-dimensional organization of EHM and/or bind extracellular matrix via integrins. In a preferred embodiment, the contraction of the MEHM is caused by the cardiac myocytes thereby generating a contractile force development of the MEHM.

The non-myocytes, as used herein, are the other cellular component of the cellular mixture in addition to the cardiac myocytes. The non-myocytes are essential for the development of a MEHM. As for example demonstrated in Schlick et al. (2019), engineered human myocardium does not compact when no non-myocytes are provided in the reconstitution mixture. In a preferred embodiment, the non-myocytes are selected from one or more of the group consisting of stromal cells, endothelial cells, smooth muscle cells, and mesenchymal stem cells, preferably wherein the non-myocytes are stromal cells or endothelial cells, more preferably wherein the non-myocytes are stromal cells, even more preferably wherein the stromal cells are cardiac stromal cells, even more preferably wherein the cardiac stromal cells have fibroblast properties, even more preferably wherein the cardiac stromal cells are fibroblasts. Typically, the non-myocytes excrete extracellular matrix proteins and/or bind extracellular matrix via integrins in order to support the formation of MEHM. In other words and in a preferred embodiment, the non-myocytes are ideally capable of compacting the reconstitution via cell-matrix interactions in step (ii). Thus, any cells capable of biophysical cell-matrix interactions and capable of secretion of extracellular matrix proteins are suitable non-myocytes. In a particularly preferred embodiment, the non-myocytes express CD90, as determined by flow cytometry, preferably wherein the non-myocytes express CD90, CD74 and CD44. As mentioned above, the non-myocytes ideally excrete extracellular matrix proteins, in particular collagen, and/or express integrins to facilitate cell-matrix interactions, wherein the non-myocytes compact the reconstitution mixture. Non-myocytes can be obtained by various sources. For example, the non-myocytes can be derived from induced pluripotent stem cells, parthenogenetic stem cells, programmed somatic cells, adult stem cells, or mesenchymal stem cells, preferably wherein the non-myocytes are derived from induced pluripotent stem cells. Furthermore, the non-myocytes can be derived from embryonic stem cells, wherein the cells are not produced using a process, which involves modifying the germ line genetic identity of human beings or which involves the use of a human embryo for industrial or commercial purposes. In another preferred embodiment the non-myocytes are derived from biopsies obtained from human subjects, preferably from patients, even more preferably from patients for autologous or allogeneic administration of EHM. Autologous patient derived non-myocytes have the advantage that the cells are obtained from the same patient and thus these cells are immunologically compatible with said patient. This is a particular advantage in case the MEHM is used as an implant for a patient. Allogeneic cells also have the advantage that they are patient derived and thus these cells are similar to the patient in need of a MEHM implant. The skilled person can use a plethora of protocols in order to obtain suitable non-myocytes. For example EP20188364.2 describes a serum-free method to obtain cardiac stromal cells with fibroblast properties. Furthermore, Witty et al. (2014), Iyer D, et al. (2015), Bao X, et al. (2016), or Bao X, et al. (2017) describe protocols for obtaining suitable non-myocytes.

In a particularly preferred embodiment, the non-myocytes of cellular mixture of step (i) are stromal cells, as for example described in EP20188364.2, preferably wherein the stromal cells are human stromal cells. In case the non-myocytes are stromal cells, the cellular mixture of step (i) may comprise at least 10% stromal cells, preferably at least 20%, more preferably at least 30%, even more preferably at least 40%, and even more preferably at least 50%. The skilled person understands that the cardiac myocytes and the non-myocytes together make up the cellular mixture, i.e. 100%. An exemplary ratio of cardiac myocytes and non-myocytes would be 50:50, 60:40, 70:30, 80:20, or 90:10, respectively. Of course any intermediate ratio could also be selected. As described above, several ratios have been tested and can be found in the literature such as in Tiburcy et al. (2017) and Schlick et al. (2019).

Typically, the reconstitution medium comprises (a) a basal medium and (b) a serum-free supplement. The serum-free supplement can be comprised within the reconstitution medium and thereby within the reconstitution mixture, the culturing medium and/or the maturation medium. In a preferred embodiment, the serum-free supplement can be formulated to provide a final concentration (1) in the reconstitution mixture, (2) the culturing medium and/or (3) the maturation medium. Of course, the concentrations and the ingredients can be independently selected for (1) in the reconstitution mixture, (2) the culturing medium or (3) the maturation medium.

For example the serum-free supplement can be formulated to provide a final concentration in any of (1)-(3) of the following components: 0.5-50 mg/ml albumin (preferably 1-40 mg/ml, more preferably 2-30 mg/ml, more preferably 3-20 mg/ml, more preferably 4-10 mg/ml and most preferably 4.5-7.5 mg/ml, such as approximately 5 mg/ml);
  1-100 µg/ml transferrin, (preferably 2-90 µg/ml, more preferably 3-80 µg/ml, more preferably 4-70 µg/ml, more preferably 5-60 µg/ml, more preferably 6-50 µg/ml, more preferably 7-40 µg/ml, more preferably 8-30 µg/ml, more preferably 9-20 µg/ml, such as about 10 µg/ml);
  0.1-10 µg/ml ethanolamine, (preferably 0.2-9 µg/ml, more preferably 0.3-8 µg/ml, even more preferably 0.4-7 µg/ml, even more preferably 0.5-6 µg/ml, more preferably 0.6-5 µg/ml, more preferably 0.7-4 µg/ml, more preferably 0.8-3 µg/ml, most preferably 1-2.5 µg/ml, such as about 2 µg/ml);
  14.4-1446 nM selenium or a bioavailable salt thereof, (preferably 40-700 nM, more preferably 70-300 nM, even more preferably 130-160 nM, most preferably about 144.6 nM); 0.4-40 µg/ml L-carnitine HCl (preferably 0.5-30 µg/ml, more preferably 1-20 µg/ml, even more preferably 2-10 µg/ml, more preferably 3-5 µg/ml, and most preferably about 4 µg/ml);
  1-100 µg/ml fatty acid supplement, (preferably 1.4-80 µg/ml, more preferably 1.8-40 µg/ml, even more preferably 2-24 µg/ml, more preferably 2.4-8 µg/ml, and most preferably 3.2-6 µg/ml, such as about 4 µg/ml); and
  0.0004-0.04 µg/ml triodo-L-thyronine (T3) (preferred 0.0010-0.02 µg/ml, more preferred 0.0016-0.010 µg/ml, even more preferred 0.002-0.006 µg/ml, most preferred about 0.004 µg/ml).

The fatty acid supplement may, for example, include linoleic acid and/or linolenic acid.

For example, a bioavailable salt of selenium is sodium selenite, so that a final concentration of sodium selenite in the reconstitution mixture, the culturing or reconstitution medium of 0.003-0.3 µg/ml (preferably 0.005-0.16 µg/ml, more preferably 0.010-0.1 µg/ml, even more preferably 0.02-0.05 µg/ml, and most preferably 0.03 µg/ml) is provided.

In another embodiment, the serum-free supplement may also comprise one or more of vitamin A, D-galactose, progesterone, and putrescine. These components are beneficial for cell viability. Suitable concentrations of the respective components are known to the skilled person or can be easily determined by routine experimentation.

An example of a serum-free supplement may be prepared according to published protocols (see also Brewer et al. (1993)) or may be commercially purchased. For example, B27 minus insulin (Table 1) can be used. In a preferred embodiment, the serum-free supplement is provided by 0.2-20% (v/v) B27 minus insulin in the reconstitution mixture, the culturing or reconstitution medium, preferably 1-16% (v/v), more preferably 2-12% (v/v), more preferably 3-8% (v/v), even more preferably 3-8% (v/v), even more preferably 3.4-5% (v/v) B27 minus insulin, and most preferably about 4% (v/v) B27 minus insulin in the reconstitution mixture, the culturing or reconstitution medium, as commercially obtained or as preferably prepared according to Table 1. Alternatively, B27 with insulin may also be applied. The optimal B27 composition can be experimentally determined for every cell type used. The person skilled in the art knows how to determine the optimal B27 composition and/or its concentration. For example Tiburcy et al. (2017) compared the used of B27 and B27 minus insulin in the online-only Data Supplementary Figure IIIF. The engineered muscle produced with B27 minus insulin shows higher force compared to the muscle produced with B27. However, said Figure also shows that B27 (with insulin) can be used for successful generation of an engineered human myocardium in order to achieve good contractility.

Furthermore, the basal medium of the reconstitution medium, the culturing medium and/or the maturating medium may additionally comprise ascorbic acid or a derivative thereof. For example, when ascorbic acid is comprised in the basal medium of the reconstitution medium, the culturing medium and/or the maturating medium, a concentration of 10-1000 µM, preferably 50-400 µM, more preferably 100-300 µM, even more preferably 150-250 µM, and most preferably about 200 µM is provided in the reconstitution mixture, the culturing medium and/or the maturating medium. Even more preferred is ascorbic acid in the form of ascorbate-2-phosphate.

In addition, the basal medium of the reconstitution medium, the culturing medium and/or the maturating medium can be RPMI, which further comprises pyruvate. An especially preferred concentration range of pyruvate in RPMI is 0.1-10 mM pyruvate, more preferably 0.2-5 mM pyruvate, even more preferably 0.4-2.5 mM pyruvate, even more preferably 0.8-1.5 mM pyruvate, even more preferably 0.9-1.2 mM pyruvate, most preferably about 1 mM pyruvate.

The basal medium of the reconstitution medium may be for example selected from Iscove's medium, RPMI, αMEM, and DMEM or a mixture thereof, preferably wherein the basal medium is selected from Iscove's medium, RPMI, αMEM or a mixture thereof, more preferably wherein the basal medium is a mixture of Iscove's medium and RPMI. However, any suitable basal medium can be used for the method. Basal media are commercially available or can be produced according to publicly available recipes, e.g. from ATCC catalogues. In general, the media, as used herein, combine suitable amounts of glucose, lactate and/or fatty acids as essential nutrients. Glucose, lactate and/or fatty acids ensure a suitable nutrient supply of the cells embedded in the reconstitution mixture.

If deemed appropriate, the basal medium may be supplemented with amino acids. If αMEM is used as the basal medium, the basal medium does, for example, not need to be supplemented additionally with non-essential amino acids. The non-essential amino acids are commercially available as a combined supplement. Such a supplement for example comprises 750 mg/L glycine, 890 mg/L L-alanine, 1320 mg/L L-asparagine, 1330 mg/L L-aspartic acid, 1470 mg/L L-glutamic acid, 1150 mg/L L-proline, and 1050 mg/L L-serine.

In an especially preferred embodiment, the reconstitution medium further comprises (c) 35-790 uM ascorbic acid, (d) 5-500 ng/ml IGF-1, (e) 0.3-26 ng/ml VEGF, (f) 0.5-53 ng/ml FGF-2, and (g) 0.5-10 ng/ml TGFβ1. In an even more preferred embodiment, the reconstitution medium further comprises (c) 75-300 uM ascorbic acid, (d) 26-105 ng/ml IGF-1, (e) 1.3-5.2 ng/ml VEGF, (f) 2.6-10.5 ng/ml FGF-2, and (g) 1-6 ng/ml TGFβ1. In an even more preferred embodiment medium further comprises (c) about 158 uM ascorbic acid, (d) about 53 ng/ml IGF-1, (e) about 2.6 ng/ml VEGF (f) about 5.3 ng/ml FGF-2, and about 3 ng/ml TGFβ1.

It is especially preferred that the VEGF is $VEGF_{165}$. The skilled person is aware of published protocols for suitable the reconstitution media such as Tiburcy et al. (2017) or Tiburcy et al. (2020), and the skilled person is capable of identifying equally suitable protocols.

The 'mould' as used herein is freely selectable and can be geometrically variable in shape. It is key that the mould holds the reconstitution mixture and that the reconstitution mixture undergoes gelation in the mould. The mould may be custom-made for the intended purpose. For example, if the purpose is an implant for the human body, the custom-made mould may match the myocardial defect. In case the purpose of the MEHM is to test, e.g. drug efficacy, a different shape may be used. The skilled person, is able to tailor the shape of the mould depending on the skilled person's need or aims. For example, the skilled person may use a 3D-printer in order to tailor the shape of the mould individually. In a preferred embodiment, the mould is formed to facilitate the formation of a planar shaped MEHM, a pouch-shaped MEHM or a cylinder-shaped MEHM. In a preferred embodiment, the mould has the form of a patch, a pouch or a cylinder. It is further preferred that the MEHM has the form of a patch, a pouch or a cylinder. In an even more preferred embodiment, the patch has the form of a disc.

If the mould is formed to facilitate the formation of a planar shaped MEHM, the mould may have the form of a disc, preferably the form of a circular or polygonal disc, more preferably the form of a hexagonal disc. Exemplary hexagonal discs are also shown in FIG. 2 and FIG. 7 as disclosed herein, and are used for the formation of a MEHM as described in Example 2.

If the mould is formed to facilitate the formation of a pouch-shaped MEHM, the mould may have the form of a pouch, preferably the form of a sphere-shaped or an ellipsoid-shaped pouch. In as especially preferred embodiment, the said mould is formed by an inner and outer sphere- or ellipsoid-shaped wall, and more preferably the inner sphere- or ellipsoid-shaped wall is inflatable. Examples of a pouch-shaped mould can be seen in FIG. 8A as disclosed herein. Furthermore, WO2008/058917 A1 and EP2842581 A1 disclose methods to generate a pouch-like engineered heart tissue as depicted in FIG. 1 therein. Thus, the skilled person is in general aware of the generation of pouch-like engineered heart tissue. However, the skilled person is not aware of a multilayer pouch-shaped EHM, wherein the reconstitution mixtures (forming MEHM) are perforated by at least two poles. As mentioned above, the moulds may be 3D-printed in order to adjust e.g. the radius of the pouch. After the completion of the pouch shaped generation of the MEHM, the pouch is detached from the mould and may be sliced open, if desired.

If the mould is formed to facilitate the formation of a cylinder shaped MEHM, the mould may have the form of a cylinder, preferably the mould is a cylindrical mould. In an especially preferred embodiment, the cylindrical mould is formed by an inner and outer cylindrical wall. In another embodiment, the cylindrical mould is formed by a single cylindrical wall. The single cylindrical wall may be covered with reconstitution mixture by centrifugation. Exemplary cylindrical mould are shown in FIG. 8B as disclosed herein. As mentioned above, the moulds may be 3D-printed in order to adjust e.g. the length or the diameter of the cylinder. A key advantage of a cylindrical shaped MEHM is that a large MEHM can be generated by using up a relatively small space. Thus, several MEHMs can be generated in parallel. A cylindrical MEHM may be sliced open along the long axis before potential use, e.g. in a patient.

As shown in exemplary FIGS. 2, 7, and 8 the reconstitution mixture is perforated by at least two poles. In an embodiment, the poles are flexible and thereby capable of introducing mechanical load on the MEHM. In general, the poles are key to the manufacture of an MEHM, as the poles serve at least two purposes: Firstly, the poles penetrating the MEHM produce channels allowing for sufficient oxygen and nutrient supply of the cells within the reconstitution mixture/MEHM. Secondly, the poles provide a physical stimulus for the developing muscle. The skilled person is aware that chemical as well as physical stimuli are crucial for the development of an engineered muscle. In other words, the poles support the force development of the MEHM as training of the muscle is crucial for its development. In an embodiment, the channels created by the perforating poles are capable of allowing perfusion of the MEHM with culturing medium in step (ii), (iii), and optionally with maturating medium in step (iv), and with oxygen in steps (ii), (iii) and optionally (iv). In an especially preferred embodiment, the perfusion of the culturing medium and/or maturating medium leads to suitable nutrient support of the cardiac myocytes and non-myocytes during steps (ii), (iii) and/or optionally (iv).

In a preferred embodiment, the reconstitution mixture is perforated by at least two poles, wherein the perforating poles are introducing channels in the reconstitution mixture/ MEHM and thereby increase the surface area of the reconstitution mixture/MEHM. In an even more preferred embodiment, the reconstitution mixture/MEHM is perforated by at least two poles, wherein the increase in surface area of the MEHM controls oxygen and nutrient diffusion distance in the MEHM. Said increase in surface area provides on average a decreased distance of the cells to the surface of the reconstitution mixture/MEHM such that the cells are sufficiently supplied with oxygen and/or nutrients, as may be determined by e.g. a hypoxia sensor (for example Hesse et al. 2014) or cell death (e.g. using well known Viability Assay dyes) as further described below. In a further preferred embodiment, the interpole distance is from 0.1 to 10 mm, preferably from 0.5 to 9 mm, more preferably from 1 mm to 8 mm, even more preferably from 2 mm to 7 mm, even more preferably from 2.5 mm to 6 mm, even more preferably from 3 mm to 5 mm, even more preferably from 3.1 mm to 6 mm, even more preferably from 3.2 mm to 5 mm, even more preferably from 3.3 mm to 4 mm, even more preferably from 3.4 mm to 3.7 mm, and most preferably about 3.5 mm. FIG. 8 shows a strongly preferred embodiment. The optimal interpole distance is of particular importance for MEHM, which are thicker than the interpole distance, as cells then may have a shorter distance to the next perforating pole than to the top or bottom surface.

In an embodiment, the reconstitution mixture is perforated by at least two poles from the bottom and/or from the top. Specifically, the reconstitution mixture may be perforated throughout its thickness. This means that the poles extend through the reconstitution mixture. In an especially preferred embodiment, the at least two poles perforate the reconstitution mixture from the bottom and the mould has the form a disc. Furthermore, the at least two poles extend from the bottom of the mould through the reconstitution mixture. It is even more preferred that the poles are permanently attached to the mould or a base plate. For example, the poles may be firmly attached to the casting area of the mould or to a removable base plate. Said base plate may also be transferred to a different mould. The advantage of a base plate is that the base plate can be removed and thereby transferred to a different mould, if desired (see e.g. FIG. 8). For example, the poles may be an integral part of the mould as permanently attached or removable elements, more preferably wherein the mould and the at least two pole element are 3D-printed, and even more preferably wherein the mould with the at least two poles is 3D-printed as one entity. It is even more preferred that the mould comprising the at least two poles is 3D-printed as one entity. 3D-printing has the advantage that the mould, such as the disc can be custommade and/or tailored. A base-plate has the advantage that a MEHM is removable and can be easily transferred from the mould to the place of use, e.g. the operating room in a suitable transport container.

In another embodiment, the at least two poles perforate the reconstitution mixture from the top and wherein the mould has the form of a disc. In an especially preferred embodiment, the at least two poles are inserted into the liquid reconstitution mixture from the top. The at least two poles may, for example, be inserted as a grid-shaped comb from the top.

In another embodiment, the at least two poles perforate the reconstitution mixture from the bottom and wherein the mould is designed to support the formation of a pouch. In an especially preferred embodiment, the pouch is formed by an inner and outer sphere- or ellipsoid-shaped wall. It is even more preferred that the at least two poles extend from the inner sphere-shaped or ellipsoid-shaped wall and thereby perforate the reconstitution mixture. In an even further preferred embodiment, the at least two poles are permanently attached to the inner sphere-shaped or ellipsoid-shaped wall.

In another embodiment, the at least two poles perforate the reconstitution mixture from the top and the mould is designed to support the formation of a pouch. In an especially preferred embodiment the pouch is formed by an inner and outer sphere- or ellipsoid-shaped wall. In an even further preferred embodiment, the at least two poles extend from the outer sphere-shaped or ellipsoid-shaped wall and thereby perforate the reconstitution mixture. It is even further preferred, that the at least two poles are permanently attached to the outer sphere-shaped or ellipsoid-shaped wall.

In another embodiment, the at least two poles perforate the reconstitution mixture from the bottom and the mould is a cylindrical mould. In a preferred embodiment, the cylindrical mould is formed by an inner and outer cylindrical wall. It is even further preferred that the at least two poles extend from the outer cylindrical wall through the reconstitution mixture and thereby perforate the reconstitution mixture. In an even more preferred embodiment, the poles are permanently attached to the outer cylindrical wall. In particular, the outer cylindrical wall comprising the at least two poles may be 3D-printed as one entity. 3D-printing has the advantage that any shape, such as a cylinder with at least 2 poles, can my created and the size can be adjusted individually.

In another embodiment, the at least two poles perforate the reconstitution mixture from the top and the mould is a cylindrical mould. In a preferred embodiment, the cylindrical mould is formed by an inner and outer cylindrical wall. In a more preferred embodiment, the at least two poles extend from the inner cylindrical wall through the reconstitution mixture. In an even more preferred embodiment, the poles are permanently attached to the inner cylindrical wall. In particular, the inner cylindrical wall comprising the at least two poles may be 3D-printed as one entity. 3D-printing has the advantage that any shape, such as a cylinder with at least two poles, can my created and the size can be adjusted individually. The mould and or the poles can be produced by any suitable engineering method, including 3D printing, cast molding, milling or glass blowing. Specifically, the mould may be manufactured by injection moulding, or milling in, e.g., a PTFE block. In a strongly preferred embodiment, the mould and/or the poles are 3D-printed.

The reconstitution mixture is cast into the mould and fully or partially fills the mould, i.e. the casting area. The skilled person is able to determine the optimal volume depending on the size of the mould. Typically, one liquid reconstitution mixture is from 1 mm to about 10 mm in thickness. Depending on the casting area and the desired thickness, the skilled person is able to determine the optimal volume by simple multiplication. In a preferred embodiment, each liquid reconstitution mixture has a volume of 0.5-200 ml, preferably 1-150 ml, more preferably 1.5-100 ml, more preferably 2-50 ml, more preferably 2.5-40 ml, more preferably 3-30 ml, more preferably 3.5-25 ml, more preferably 4-20 ml, more preferably 4.5-15 ml, more preferably 5-11.5 ml, more preferably 6-9.5 ml, even more preferably 6.5-8.5, and most preferably about 8 ml. An exemplary EHM, wherein a volume of 8 ml was used, is shown in FIG. 2 as disclosed herein.

The mould may hold a volume of 1-400 ml. The volume the mould may hold can be determined by the casting area multiplied by the possible height of the MEHM. For example, if the mould enables the formation of a disc, the mould volume can be calculated by the casting area multiplied by the height of the mould. Exemplary casting mould in order to generate a hexagonal disc are shown in FIG. 7A. If the mould, has the form of a pouch, the volume of the mould is the difference between sphere- or ellipsoid-volume of the outer and the inner wall. Similarly, if the cylinder-shaped mould has an outer and an inner wall, the volume of the mould can be determined by the volume difference between the outer and the inner wall of the cylinder. In case the cylinder-shaped mould only comprises one outer wall, the cylinder-shaped mould could theoretically hold the whole cylinder volume. In a preferred embodiment, the mould holds a volume of 2-300 ml, more preferably of 3-200 ml, more preferably of 4-100 ml, more preferably of 5-80 ml, more preferably of 6-60 ml, more preferably of 6.5-50 ml, more preferably of 7-40 ml, more preferably of 7.5-30 ml, more preferably of 8-23 ml, more preferably of 13-19 ml even more preferably of 13-17 ml, and even more preferably about 15 ml. As described above, the mould may be patch-shaped, pouch-shaped or cylinder-shaped.

As described above, the mould has a casting area. The liquid reconstitution mixture is cast into the casting area. In other words, the size of the mould describes the casting area size. Furthermore, the skilled person is able to determine the ideal casting area of the mould depending on the skilled person's need. For example, if the MEHM is desired to be used as a implant, the mould may be custom-made with e.g. a 3D-printer. In a preferred embodiment, the mould has a size of 1-400 cm$^2$, preferably of 2-300 cm$^2$, more preferably of 3-200 cm$^2$, more preferably of 4-100 cm$^2$, more preferably of 5-80 cm$^2$, more preferably of 6-60 cm$^2$, more preferably of 7-50 cm$^2$, more preferably of 8-40 cm$^2$, more preferably of 9-30 cm$^2$, more preferably of 10-23 cm$^2$, more preferably of 12-19 cm$^2$ even more preferably of 13-17 cm$^2$, even more preferably about 16 cm$^2$. In a strongly preferred embodiment, the mould is used for the formation of an MEHM in patch-shape.

As mentioned above, the reconstitution mixture is perforated by at least two poles. In a preferred embodiment, the reconstitution mixture is perforated by at least three poles. In an even more preferred embodiment, the poles are arranged as a grid, more preferably wherein the poles are arranged as a triangular or rectangular grid, even more preferably as a triangular grid. An exemplary triangular grid arrangement is shown in e.g. FIG. 7 as disclosed herein. However, the skilled person is able to identify other suitable grid arrangements.

A suitable number as well as the diameter of the poles perforating the reconstitution mixture is dependent on the mould size. The poles perforating the reconstitution mixture serve two purposes: Firstly, the poles ensure the formation of channels for sufficient oxygen and nutrient supply of the cells within the reconstitution mixture. Secondly, the poles support the training of the developing muscle, i.e. the poles support the force development of the muscle. The skilled person is able to determine the optimal number of poles depending on the mould size. With simple experimentation, the skilled person is able to determine whether the cells are not sufficiently supplied with oxygen and/or nutrients. For example, Hesse et al. (2014) describe that a hypoxia sensor can be used in engineered tissues such as engineered heart muscle, in order to determine whether the cells suffer from hypoxia. Furthermore, the cells may die, if they are not supplied sufficiently with oxygen and/or nutrients, which can also be determined by standard experimentation using staining methods. In addition, the skilled person is able to determine the optimal number and diameter of the poles, by the contractility of the MEHM. As described above, contraction can be measured by FAC or FOC as described e.g. in Tiburcy et al. (2017) or Zimmermann et al. (2000). In a preferred embodiment, the reconstitution mixture is perforated by at least 5 poles, more preferably at least 7 poles, more preferably at least 14 poles, even more preferably at least 20 poles, even more preferably at least 30 poles, even more preferably at least 37 poles, and most preferably at least 52 poles. The exemplary casting moulds as depicted in FIGS. 7A and 7C herein show 52 and 14 poles respectively. According to the inventors' best knowledge, there is no fixed upper limits for the number of poles. For example, the reconstitution mixture might be perforated by at most 2000, preferably at most 1500, even more preferably at most 1000. In light of the present disclosure, the skilled person can freely combine the boundaries of the number of poles. In another especially preferred embodiment, the poles have a diameter of 0.5 to 3 mm, preferably of 0.6 to 2.5 mm, more preferably of 0.65 to 2 mm, even more preferably of 0.7-1.7 mm, and even more preferably of about 0.8-1.5 mm. As further shown in FIG. 7C, varying diameters from 0.8-1.1 mm have also been experimentally tested. In an especially preferred embodiment, the reconstitution mixture may be perforated by at least seven poles, wherein the poles are arranged in a grid and wherein the diameters of the poles form a gradient along one planar axis. One example of a gradient of the diameter is depicted in FIG. 7C, as disclosed herein. Furthermore, a gradient in diameter can lead to the technical effect that the measured FAC along the gradient is larger than the measured FAC along poles with an equal pole thickness. This finding is also supported by experimental data, as shown in FIG. 7C.

For example, the casting mould as depicted in FIG. 7A comprises 52 poles and each liquid reconstitution mixture has a volume of 8 ml. The skilled person may also extrapolate the reconstitution mixture volume and number of poles from this example.

In a preferred embodiment, each pole has a base area and the base may be circular, rectangular, elliptical, triangular or polygonal, preferably wherein the base area is circular. The circular base area of the poles is also depicted in e.g. FIGS. 7 and 8 herein.

Advantageously, the poles create restoring forces to simulate the heart wall stress of the normal and/or infarcted heart during a contraction cycle. The restoring force is a force which acts to bring a body to its equilibrium position. As described above, the poles are typically flexible in order to introduce mechanical load on the MEHM. Thus, the poles ideally have elastic properties (flexibility). In general, the elastic properties of the poles are quantified by the elastic modulus, or Young's modulus, which defines the amount of stress needed to achieve a unit of strain. For example, a higher modulus indicates that the material is harder to deform. In general, the SI unit of this modulus is the pascal (Pa). For example, Rump et al. (2007) and Pislaru et al. (2014) describe the viscoelastic properties of normal and infarcted myocardium. The ideal engineered tissue mimics the contractile (about 0.3 to 60 mN/mm$^2$; Wiegerinck et al.

2009, Muleri et al. 1992) and viscoelastic (5 to 27 kPa; Rump et al. 2007) properties of the normal and/or infarcted myocardium.

In an especially preferred embodiment, the restoring force of the poles ideally matches the wall tension of normal and/or diseased myocardium (10 to 200 kdynes/cm2 or 1 to 20 kPa; Fujita et al. 1993). The elastic properties may be defined by the working spring rate. In the present case the working spring rate may be assessed at the point at which the MEHM is in contact with the poles. In general, the spring rate is defined as the amount of force it takes to deform a spring by one distance unit. The units of measurement of spring rate is typically N/mm (newtons per millimeter) or mN/mm (millinewtons per millimeter). In a strongly preferred embodiment, the elastic properties of the poles, as defined by the elastic modulus, create restoring forces from 0.5 to 50 mN/mm, preferably from 0.7 to 40 mN/mm, more preferably from 0.9 to 30 mN/mm, even more preferably from 1 to 20 mN/mm, even more preferably from 2 to 10 mN/mm, even more preferably from 3 to 5 mN/mm, and most preferably about 4 mN/mm. In an especially preferred embodiment, the restoring forces of the poles match the wall tension of normal and/or diseased human heart, even more preferably wherein the wall tension is from 1 to 20 kPa. Said range is also disclosed in Fujita et al. (1993).

The elastic properties of the poles may exhibit varying elastic moduli to establish biomechanical anisotropy. In other words, the elastic moduli exhibit variations between the poles. In another embodiment, the elastic properties of the poles exhibit similar elastic moduli to establish biomechanical isotropy. In other words, the elastic moduli are uniform across the poles.

In another embodiment, the poles are surrounded by a circumferential wall in the lower part of the poles, wherein the circumferential wall forms a ring-shaped ramp around the poles, and wherein the ring-shaped ramp tapers from the bottom upwards. Exemplary dimensions, of the circumferential wall are depicted in FIG. 4B for ring-shaped EHM. Furthermore, WO 2017/207431 A1 describes said circumferential wall in detail. The advantage of a circumferential wall at the bottom of the poles is that a compacted reconstitution mixture moves upwards along to ramp due to compaction and/or muscle force development. This sliding upwards due to compaction and/or muscle force development facilitates the addition of a further reconstitution mixture from the bottom, as described in step (iii) of the method.

In another embodiment, the poles taper conically and the poles have the largest diameter at the bottom. A tapering from the bottom to the top of the poles has a similar advantage as the circumferential wall: The EHM can detach from the mould and slide upwards in order to facilitate the addition of a further reconstitution mixture, particularly an addition from the bottom.

The skilled person is aware of suitable conditions in order to perform tissue culture experiments. In a preferred embodiment, steps (i), (ii), and/or optionally (iv) are carried out at a temperature range of 36.4-37.6° C., preferably at a temperature range of 36.6-37.4° C., preferably at a temperature range of 36.8-37.2° C., more preferably at about 37° C. Furthermore and in another preferred embodiment, steps (i), (ii), and/or optionally (iv) are carried out in a humidified cell culture incubator in the presence of 2-10% $CO_2$, preferably 2.5-8% $CO_2$, more preferably 3-7% $CO_2$, even more preferably 3.5-6.5% $CO_2$, even more preferably 4-6% $CO_2$ and most preferably about 5% $CO_2$. In general, the culturing may be at ambient oxygen or oxygen carriers, e.g. hemoglobin-based oxygen carriers (HBOCs) and perfluorocarbon-based oxygen carriers (PFOCs) may be present (Iyer et al. 2007). In another preferred embodiment, steps (i), (ii), and/or optionally (iv) are carried out in a humidified cell culture incubator in the presence of 5-40% $O_2$, preferably 10-30% $O_2$, more preferably 15-35% $O_2$, even more preferably 17-33% $O_2$, even more preferably 19-25-% $OP_2$ and most preferably about 21% $O_2$. Furthermore, the skilled person is aware from common general knowledge, that said temperature ranges and CO2 ranges are standard tissue culture conditions in the art. Furthermore, 21% O2 corresponds to the usual concentration of oxygen in dry air In step (i), the liquid reconstitution mixture undergoes gelation. When the reconstitution mixture has undergone gelation, the reconstitution mixture is no longer liquid—in other words non-liquid. In a preferred embodiment, gelation is characterized in that the reconstitution mixture obtained by step (i) is gel-like. Gelation of the reconstitution mixture occurs, due to the collagen in the reconstitution mixture. For example, if highly purified bovine corium (skin) type I acid solubilized collagen is used in the reconstitution mixture, the pH value of the reconstitution mixture is adjusted to a physiological pH, e.g. between 7.0-8.0. Upon this ph-value shift, the collagen forms a gel. In fact, the ideal conditions for gel formation (3D-scaffold) of collagen is at a pH of around 7. Biochemically, the native collagen molecules are covalently cross-linking hydroxylysine and lysine residues. Thus, native collagen molecules are able to self-assemble into collagen fibrils and form hydrogels, through crosslinking at 37° C. and near neutral pH in vitro. Said self-assembling gelation process can be initiated by the pH-shift and occurs optimally at 37° C. The physicochemical properties of collagen hydrogels are influenced by collagen concentration, polymerization pH, and ionic strength during crosslinking. The skilled person is aware of this process and said process has been performed for various tissue engineering applications in order to form a 3D-scaffold (e.g. Tiburcy et al. 2017). In an especially preferred embodiment, the reconstitution mixture has a pH from 7.0 to 7.8, preferably a pH from 7.2 to 7.6, more preferably from 7.3 to 7.5, and most preferably wherein the reconstitution mixture has a pH of around 7.4.

In another preferred embodiment, the gelation in step (i) is characterized in that the culturing medium surrounds the reconstitution mixture and does not dissolve the reconstitution mixture, if added to the mould. The skilled person may for example assess the gelation of the reconstitution mixture by testing whether the culturing medium dissolves the reconstitution mixture after various time points. This testing could also be performed in experimental tubes in parallel to the manufacture of an MEHM. Furthermore, the gelation in step (i) may be characterized in that the reconstitution mixture is opaque, preferably as determined by visual inspection as shown in FIG. 3B of Tiburcy M, et al. (2014).

In a strongly preferred embodiment, step (i) is carried out for at least 15 minutes, preferably for at most 24 hours, more preferably from 20 minutes to 15 hours, more preferably from minutes to 8 hours, even more preferably from 45 minutes to 1.5 hours, and most preferably for about 1 hour.

In another embodiment, the culturing medium in step (ii), comprises (a) a basal medium, (b) a serum-free supplement, (c) L-glutamine, (d) ascorbic acid, (e) IGF-1, (f) VEGF, and (g) TGFβ1. However, the skilled person is able to identify suitable culturing media. For example, Tiburcy et al. (2017), (2020) and Schlick et al. (2019) provide exemplary culturing media suitable for culturing EHM. Each of the factors, such as IGF-1, VEGF and/or TGFβ1 can be substituted by a factor with an equal or similar effect. For example, TGFβ1 may be substituted with any other factor, which stimulates non-myocytes, in particular stromal cells, in order to initiate the compaction of the reconstitution mixture.

In a preferred embodiment, the basal medium of the culturing medium is selected from Iscove's medium, αMEM, DMEM, and RPMI, preferably the basal medium is Iscove's medium or αMEM, more preferably wherein the basal medium is Iscove's medium. However, any suitable basal medium can be used for the method. Basal media are commercially available or can be produced according to publicly available recipes, e.g. from ATCC catalogues. If deemed appropriate, the basal medium may be supplemented with amino acids. In another preferred embodiment, the culturing medium may comprise a serum-free supplement. The serum-free supplement may provide a final concentration in the culturing medium as defined above. In another preferred embodiment, the culturing medium in step (ii) may comprise mM L-glutamine, preferably 0.8-6 mM L-glutamine, more preferably 1.2-5 mM L-glutamine, more preferably 1.5-4 mM L-glutamine, more preferably 1.7-3 mM L-glutamine and most preferably about 2 mM L-glutamine. In a very strongly preferred embodiment, the culturing medium in step (ii) may comprise 30-3000 µM ascorbic acid or a derivative thereof, preferably 100-1000 µM ascorbic acid or a derivative thereof, more preferably 180-500 µM ascorbic acid or a derivative thereof, more preferably 220-370 µM ascorbic acid or a derivative thereof, more preferably 270-330 µM ascorbic acid or a derivative thereof and most preferably about 300 µM ascorbic acid or a derivative thereof. One example of a derivate of ascorbic acid is ascorbate-2-phosphate.

In another preferred embodiment, the culturing medium in step (ii) comprises 10-1000 ng/ml IGF1, preferably 50-500 ng/ml IGF1, more preferably 70-200 ng/ml IGF1, even more preferably 90-120 ng/ml IGF1, and most preferably about 100 ng/ml IGF1. In particular, IGF1 may be human IGF1.

In another preferred embodiment, the culturing medium in step (ii) comprises 2.5-10 ng/ml VEGF, preferably 3-9 ng/ml VEGF, more preferably 3.5-8 ng/ml VEGF, more preferably 4-7 ng/ml VEGF, more preferably 4.5-6 ng/ml VEGF, most preferably about 5 ng/ml VEGF. In particular, the VEGF may be human VEGF, preferably wherein VEGF is $VEGF_{165}$.

In another preferred embodiment, the culturing medium in step (ii) comprises 5-20 ng/ml FGF-2, preferably 6-18 ng/ml FGF-2, more preferably 7-16 ng/ml FGF-2, more preferably 8-14 ng/ml, more preferably 9-12 ng/ml FGF-2, most preferably about 10 ng/ml FGF-2. In particular, the FGF-2 may be human FGF-2.

In another preferred embodiment, the culturing medium in step (ii) comprises 2-8 ng/ml TGFβ1, preferably 3-7 ng/ml TGFβ1, more preferably 4-6 ng/ml TGFβ1, even more preferably 4.5-5.5 ng/ml TGFβ1, even more preferably about 5 ng/ml TGFβ1, and most preferably wherein the TGFβ1 is human TGFβ1.

In another preferred embodiment, the culturing medium in step (ii) comprises about 750 mg/L glycine, about 890 mg/L L-alanine, about 1320 mg/L L-asparagine, about 1330 mg/L L-aspartic acid, about 1470 mg/L L-glutamic acid, about 1150 mg/L L-proline, and about 1050 mg/L L-serine.

During step (ii) the reconstitution mixture compacts. Step (ii) results in a compacted reconstitution mixture. In a preferred embodiment, the reconstitution mixture in step (ii) compacts by at least about 20% of the original reconstitution mixture volume, preferably by at least about 25%, more preferably by at about least 30%, more preferably by at least about 40%, more preferably by at least about 50%, even more preferably by at least about 60%, more preferably by at least about 70%, more preferably by at least about 80%, even more preferably by at least about 90%, as preferably determined by visual inspection and/or video-optic analysis. EHM volume can, for example, be assessed by planimetric methods, assuming that EHM volume compaction is symmetrical in all dimensions. In addition, the thickness can for example be precisely determined by ultrasound, laser interferometry, or optical coherence tomography. By a combination of planimetric area and thickness measurements the EHM volume can be determined. In a preferred embodiment, the completion of step (ii) is determined by (a) generating an engineered heart muscle (EHM) in loop format in parallel to the MEHM by carrying out steps (i) and (ii), and (b) determining the detachment of the engineered heart muscle (EHM) in loop-format from the mould, as described in in FIG. 3C of Tiburcy M, et al., Collagen-based engineered heart muscle, Methods Mol Biol. (2014); 1181: 167-176. The detachment from the mould can easily be assessed by generating an EHM in loop format in parallel, as the detachment is clearly visible. For example FIG. 5C herein also shows a clear detachment of the EHM in loop format from the mould. In a further preferred embodiment, the completion of step (ii) can be further determined by generating an EHM in loop format in parallel to the MEHM by following steps (i) and (ii), and wherein the reconstitution mixture in loop format compacts by at least 20% of the original reconstitution mixture cross-sectional area, preferably by at least 25%, more preferably by at least 30%, more preferably by at least 40%, more preferably by at least 50%, more preferably by at least 60%, more preferably by at least 70%, more preferably by at least 80%, even more preferably by at least 90%. Said compaction can be assessed by visual inspection and/or video-optic analysis of the EHM. FIG. 5C herein shows an optimal compaction of an EHM in loop format as an example.

In an especially preferred embodiment, step (ii) is carried out for at least 12 hours, preferably for at most 15 days, more preferably 12 hours to 7 days, preferably from 14 hours to 6 days, more preferably from 16 hours to 5.5 days, more preferably from 18 hours to 5 days, more preferably from 20 hours to 4.5 days, even more preferably from 22 hours to 4 days, even more preferably from 23 hours to 3.5 days, and most preferably from 24 hours to 3 days.

In step (iii), a further reconstitution mixture is added from the top and/or the bottom to the reconstitution mixture of step (ii). In a preferred embodiment, in step (iii)a) one further reconstitution mixture is added on top of the compacted reconstitution mixture of step (ii), In another preferred embodiment, in step (iii)a) one additional reconstitution mixture is added from the bottom to the compacted reconstitution mixture of step (ii). In another preferred embodiment, in step (iii)a) one additional reconstitution mixture is added to the compacted reconstitution mixture of step (ii) from top and bottom simultaneously. In an even more preferred embodiment, in step (iii)a) the further reconstitution mixture coats the compacted reconstitution mixture of step ii) from the top and/or the bottom. For example, the surface area of the compacted reconstitution mixture of step (ii) and the further reconstitution mixture of step (iii)a) is the same. For illustration, the five-layered EHM as shown in FIG. 3 has been generated by coating the compacted reconstitution mixture of step (ii) and wherein the surface area of the further reconstitution mixture of step (iii)a) and the compacted reconstitution mixture of step (ii) is the same. In another example, in step (iii)a) the further reconstitution mixture coats a restricted area of the compacted reconstitution mixture of step ii) from the top or the bottom. The surface area of the further reconstitution mixture of step (iii)a) may be smaller than the surface area of the reconstitution mixture of step (ii). For illustration, FIG. 8C2 depicts inlets, which can be placed on the compacted reconstitution mixture of step (ii) in order to provide a smaller sized liquid reconstitution mixture on top of the compacted reconstitution of step (ii). For example, a smaller surface area of the reconstitution mixture of step (iii)a) may be adjustable to a patient specific defect or another desired shape. This has the advantage that a MEHM for use in heart repair may be more enforced at a particular restricted area compared to the rest of the MEHM.

In another embodiment, the surface area of the further reconstitution mixture is larger than the surface area of the compacted reconstitution mixture of step (ii). For example, in step (iii)b) the different mould has a larger casting area than the mould of step (i), preferably wherein the further reconstitution mixture coats at least the compacted reconstitution mixture of step (ii) from the top or from the bottom. It is even more preferred that the further reconstitution mixture coats the compacted reconstitution mixture of step (ii) from the top or from the bottom and fills the larger casting area of the different mould. For illustration, FIG. 8C1 depicts compacted reconstitution mixtures of smaller size has been transferred into a mould with a larger surface area. For example, a larger surface area of the different mould in step (iii)b) may be adjustable to a patient specific defect. This has the advantage that a MEHM for use in heart repair may be tailored to the specific need.

By adding the further reconstitution mixture in step (iii), an additional layer of the EHM is generated. Thus, the addition the further reconstitution mixture thickens the EHM layer-by-layer. The desired thickness can be determined by the skilled person. For example, the MEHM may be used as an implant for a human heart. Preferably, the human defect is imaged by state in the art imaging techniques such as echocardiography, magnetic resonance imaging, or computed tomography, and the desired thickness and dimensions can be determined. In a preferred embodiment, step (iii)a) or (iii)b) is repeated at least 2 times, preferably at least 3 times, more preferably at least 4 times, more preferably at least 5 times, more preferably at least 6 times, more preferably at least 7 times, more preferably at least 8 times, even more preferably at least 9 times, and most preferably at least 10 times. In an even more preferred embodiment, step (iii)a) or (iii)b) is repeated 2-200 times, preferably 2-100 times, more preferably 2-80 times, more preferably 2-70 times, more preferably 2-60 times, more preferably 2-50 times, more preferably 2-40 times, more preferably 3-30 times, more preferably 3-25 times, more preferably 4-20 times, more preferably 4-15 times, more preferably 4-10 times, even more preferably 5-9 times, and most preferably 5-8 times. However, the skilled person is able to determine how many times step (iii) shall be repeated and whether step (iii)a) or (iii)b) should be performed. The skilled person will be guided by the desired dimensions and geometries and will thereby assess whether the layers should have the same surface area or whether individual layers shall be smaller or larger. For example, the skilled person may desire a heart implant. Thus, the surface area of the individual layers will be customized to the myocardial defect size. In addition, the thickness of the MEHM ideally matches the thickness of the healthy tissue. For example, one compacted reconstitution mixture may have the thickness of e.g. ~500 µm. In order to achieve the desired heart wall thickness of up to 10 mm (Kawel et al. (2012)), 20 compacted reconstitution mixtures may be layered. In another example, a compacted reconstitution mixture may be thinner than 500 µm. Then, 50 reconstitution mixtures may need to be layered in order to obtain a typical heart wall thickness. The skilled person is able to determine how many reconstitution mixtures are required in order to obtain a MEHM with the thickness of a typical human heart and/or the myocardial defect of a patient.

After completion of step (iii), the EHM may be further matured in maturating medium. The skilled person can find exemplary compositions of maturating medium for example in Tiburcy et al. (2017) or Tiburcy et al. (2020). In a particularly preferred embodiment, the maturating medium in step (iv) is defined as the culturing medium above, except that TGFβ1 is omitted from the maturating medium compared to the culturing medium. In an even more preferred embodiment, step (iv) is carried out for 4-200 days, preferably 6-150 days, more preferably 8-120 days, more preferably 9-110 days, more preferably 10-90 days, more preferably 15-70 days, more preferably 20-50 days, and most preferably 28-42 days.

In a preferred embodiment, the MEHM of step (iii) is cultured in a suitable maturating medium in step (iv), whereby the MEHM of step (iv) exhibits enhanced maturation as determined by increased cardiomyocyte sarcomeric protein abundance, such as alpha sarcomeric actinin, myosin heavy chain proteins, myosin light chain proteins, and troponins determined by for example fluorescence microscopy after antibody labelling of one or several of the indicated proteins, western blotting, flow cytometry or RNA-sequencing to determine the abundance of the respective protein encoding transcripts as described in Tiburcy et al. Circulation 135(19)1832-1847 (2017). Further, MEHM of step (iv) may exhibit increased force development when compared to the MEHM of step (iii), wherein the increased force development is determined by a fractional area change (FAC) measurement using the method described in Tiburcy et al. Circulation 135(19)1832-1847 (2017), and wherein the fractional area change (FAC) of the MEHM of step (iv) is at least 0.5% upon electrical stimulation, preferably at least 1%, more preferably at least 1.2%, more preferably at least 1%, more preferably at least 2%, more preferably at least 3%, and even more preferably at least 5%.

One particular advantage of the method as disclosed herein is that the cells within reconstitution mixture/MEHM are sufficiently supplied with nutrients and oxygen at all times. The sufficient nutrient supply is ideally achieved by ensuring a minimally acceptable surface-tissue diffusion distance by creation of channels via the perforating poles at all times during the manufacturing process while still producing a thickened MEHM, which may for example be used as an implant. For example, the inter-pole distance may be 3.5 mm so that the diffusion distance is 1.75 mm, i.e. the distance from the pole (tissue surface) to the tissue core (center between two poles; FIG. 8 and further described above). In other words, the diffusion distance from the tissue surface (pole or top/bottom surface) to the tissue core is kept at an optimum. Said diffusion distance can be adjusted by the number of perforating poles and the pole design. Optimal surface-tissue diffusion distance can be determined by tissue hypoxia measurements (e.g. using the ODD-Luc hypoxia reporter described in Hesse A R, et al. (2014)) or cell survival assays (e.g. using well known Viability dyes). Viability dyes, also known as live/dead stains, are known in the art and can be commercially purchased from various suppliers. For example, an intracellular esterase can hydrolyzes a dye to produce a hydrophilic, strongly fluorescent compound in live cells so that a fluorescent signal can be measured at e.g. Ex/Em=485/530 nm in live cells. Dead cell dyes enter damaged cell membranes and may undergo a 40-fold enhancement of fluorescence upon binding to nucleic acid, thereby producing a bright red fluorescence (Ex/Em=495/635 nm) in dead cells. In MEHM formulations surface-tissue distance is defined by the interpole distance of the perforating poles. An example of a suitable interpole distance of 3.5 mm resulting in a maximal surface-core diffusion distance of 1.75 mm is depicted in FIG. 8. To exemplify, with this a choice of a interpole distance of 3.5 mm there will be a maximal surface-tissue core diffusion distance of 1.75 mm irrespective of the MEHM thickness. The person skilled in the art can with the information provided herein determine and adapt the optimal interpole distance in MEHM as required to ensure oxygen and nutrient support throughout MEHM of desired dimensions and thickness. For example, a liquid reconstitution mixture of 8 ml compacts to around 0.8 ml when a single-layered EHM is generated, e.g. by following steps (i), (ii) and (iv), and as shown in FIG. 3C, right side. Such single-layered EHMs can be between 0.5 mm and 1 mm. Thus, the reconstitution mixture may compact by around 90% throughout the process. However, an artificial heart tissue for use in the clinic ideally has a thickness of at least 5 mm in order to sustain the stress of the beating heart and support the beating heart. As a thought experiment and in order to obtain an EHM with a thickness of at least 5 mm with a single reconstitution mixture, the skilled person would need to cast a reconstitution mixture of at least 80 ml, which corresponds to a thickness of the liquid reconstitution mixture of 50 mm (5 cm). However, the cells at the center of such a thick single-reconstitution mixture would not survive such a method as said cells would suffer from necrosis in the core of the reconstitution mixture and subsequently compacting tissue due to hypoxia and lack of nutrients. The introduction of perforating poles circumvents this limitation as it establishes a desired optimal surface-tissue core diffusion distance to ensure sufficient oxygen and nutrient supply throughout the MEHM.

The other key advantage of the method as disclosed herein is that the layers are added sequentially. Thus, each further reconstitution mixture merges to the compacted reconstitution mixture of step (ii). Due to said merging, the resulting MEHM originates from several layers, however, the layers are inseparable. In other words, the forming MEHM behaves like single muscle, as the individual layers merge to form a single entity. This is a particular advantage compared to a fusion of individually stacked engineered heart myocardiums as disclosed in WO2007054286, Zimmermann et al. 2006, and Naito et al. 2006.

In a preferred embodiment, hypoxia is determined with a hypoxia reporter. In a particularly preferred embodiment, the cardiac myocytes in the MEHM are sufficiently supplied with oxygen, preferably wherein the oxygen supply is determined by the ODD-Luc hypoxia reporter as described in Hesse A R, et al. (2014). This embodiment is also supported by experimental evidence as illustrated in FIG. 3D. In said experiment, the cardiomyocytes of the inner most layer of the MEHM and the single layer EHM comprise the ODD-Lux hypoxia reporter. As can be seen from the comparison in FIG. 3D, the single-layer EHM in fact shows more hypoxia than the 5-layered EHM. In a particularly preferred embodiment, the cardiac myocytes in the MEHM are suf-ficiently supplied with oxygen, which is determined by the ODD-Luc hypoxia reporter as described in Hesse A R et al. (2014), preferably wherein a sufficient oxygen supply is ensured if the mean relative luminescence of cardiac myocytes of the MEHM is at most 6-fold higher than in a single-layer EHM as obtained by following steps (i), (ii) and optionally (iv) of the method, more preferably at most 5-fold, more preferably at most 4-fold, more preferably at most 3-fold, more preferably at most 2.5-fold, even more preferably at most 2-fold, and even more preferably at most 1.5-fold. In an even more preferred embodiment, the cardiac myocytes in the MEHM are sufficiently supplied with oxygen, which is determined by the ODD-Luc hypoxia reporter as described in Hesse A R et al. (2014), and wherein the mean relative luminescence of cardiac myocytes of the MEHM is not greater than the mean relative luminescence measured in cardiac myocytes of a single-layer EHM, as e.g. experimentally shown in FIG. 3C.

In another aspect, a multilayer engineered heart muscle (MEHM) obtained by the method as disclosed herein is also described. Furthermore, a multilayer engineered heart muscle (MEHM) obtainable by the method as disclosed herein is also described.

In another aspect, a multilayer engineered heart muscle (MEHM) is disclosed, wherein the MEHM comprises (a) collagen and (b) a cellular mixture of cardiac myocytes and non-myocytes, and wherein the EHM comprises at least 2 layers. It is preferred that the MEHM is a patch, a pouch, or a cylinder. It is even more preferred that the MEHM has a thickness of at least 0.2 mm. It is further preferred, that the MEHM has been generated by a repetitive and sequential layering method, wherein the MEHM originates from 2-200 layers. It is further preferred that the layers have been merged to each other and thereby expand the MEHM thickness. The skilled person is aware that the cellular mixture requires a medium in order to supply the cells with nutrients. It is even further preferred, that each layer of the MEHM originates from a reconstitution mixture, wherein the reconstitution mixture comprises (a) collagen, (b) a cellular mixture of cardiac myocytes and non-myocytes, and (c) a suitable reconstitution medium.

In a preferred embodiment, a multilayer engineered heart muscle (MEHM) is described wherein the MEHM is characterized in that the MEHM has been generated by a repetitive and sequential layering method, wherein the MEHM originates from 2-200 layers, wherein the layers have been merged to each other and thereby expand the MEHM thickness, wherein each layer originates from a reconstitution mixture, and wherein each reconstitution mixture comprises (a) collagen, (b) a cellular mixture of cardiac myocytes and non-myocytes and (c) a suitable reconstitution medium.

It is even further preferred that the MEHM is capable of contracting, as measured by determining the fractional area change (FAC) of the MEHM using the method described in Tiburcy et al. Circulation 135(19)1832-1847 (2017). In an even more preferred embodiment, the FAC is at least 0.5% upon electrical stimulation, preferably wherein the FAC is at least more preferably at least 1%, more preferably at least 2%, more preferably at least 3%, and even more preferably at least 5%.

In a very preferred embodiment, the MEHM originates from 2-100 layers, preferably 2-80 layers, more preferably 2-70 layers, more preferably 2-60 layers, more preferably 2-50 layers, more preferably 2-40 layers, more preferably 3-30 layers, more preferably 3-25 layers, and even more preferably 4-20 layers. For example, 20 layers with an individual fully compacted thickness of 0.5 mm per reconstitution mixture may be a desirable setup for the manufacture of an MEHM for the use as a human implant.

As a result of the at least two layer, the MEHM may be from 0.2 mm to about 30 mm in thickness, preferably from about 0.3 mm and to about 30 mm, more preferably from about mm to about 30 mm, more preferably from about 0.7 mm to from about 25 mm, more preferably from about 0.9 mm to about 20 mm, more preferably from about 1 mm to about 17 mm, more preferably from about 2.3 mm to about 15 mm, more preferably from about 2.8 mm to about 14 mm, more preferably from about 3.3 mm to about 13 mm, more preferably from about 3.8 mm to about 12 mm, more preferably from about 4.2 mm to about 11 mm, more preferably from about 4.6 mm to about 10.5 mm, and most preferably from about 5 mm to about 10 mm.

It is even more preferred that the MEHM is not vascularized and/or the MEHM is not under the control of the central nervous system. In a preferred embodiment, the MEHM is perforated by at least 2 poles with similar diffusion distances throughout the MEHM to ensure nutrient and oxygen supply of the cellular mixture. For example, the cardiac myocytes in the MEHM are sufficiently supplied with oxygen, preferably wherein the oxygen supply is determined by the ODD-Luc hypoxia reporter as described in Hesse A R et al. (2014). Specifically, the cardiac myocytes in the MEHM may be sufficiently supplied with oxygen, which is determined by the ODD-Luc hypoxia reporter as described in Hesse A R et al. (2014), preferably wherein a sufficient oxygen supply may be ensured if the mean relative luminescence of cardiac myocytes of the MEHM is at most 6-fold higher than in a single-layer EHM, which can be obtained by following steps (i), (ii) and optionally (iv) of the method as disclosed herein, more preferably at most 5-fold, more preferably at most 4-fold, more preferably at most 3-fold, more preferably at most 2.5-fold, even more preferably at most 2-fold, and even more preferably at most 1.5-fold.

It is especially preferred that the cardiac myocytes in the MEHM are sufficiently supplied with oxygen, which is determined by the ODD-Luc hypoxia reporter as described in Hesse A R et al. (2014), and wherein the mean relative luminescence of cardiac myocytes of the MEHM is not greater than the mean relative luminescence measured in cardiac myocytes of a single-layer EHM.

In a preferred embodiment, the MEHM is obtained by any embodiment or combination of embodiments of the method as disclosed herein. The MEHM as disclosed herein may show any feature as disclosed with regard to the method as disclosed herein.

In another aspect, the MEHM is obtained by a carrying out steps (i)-(iii) of the method as disclosed herein.

In a further aspect, an engineered heart muscle, preferably an engineered heart patch, engineered heart pouch, or engineered heart cylinder is disclosed, wherein the EHM comprises (a) collagen, (b) a cellular mixture of cardiac myocytes and non-myocytes and wherein the EHM has a thickness of at least about 0.6 mm. Preferably said EHM is a MEHM and comprises at least 2 layers.

In another aspect, a use of the MEHM obtained by the method as disclosed herein or the MEHM as disclosed herein in an in vitro model for drug screening is also described. In particular, the MEHM may be used in an in vitro model for drug toxicity screening or drug efficacy screening.

Furthermore, a use of the MEHM obtained by the method as disclosed herein or the MEHM as disclosed herein in an in vitro manufacture of an engineered human myocardium is also described. In a preferred embodiment, the MEHM has the three-dimensional shape to match patient-specific myocardial defect, more preferably wherein the patient-specific myocardial defect is assessed by MRI, ultrasound, computer tomography, positron emission tomography and/or optical coherence tomography. The skilled person is aware of all these methods as they are standard practice in the art. After assessing the three-dimensional patient-specific myocardial defect, the skilled person can generate a MEHM with tailored dimensions. For example, the skilled person can produce a MEHM according to the myocardial wall thickness of the patient, preferably according to the myocardial wall thickness of the patient before the defect occurred.

The MEHM obtained by the method as disclosed herein or the MEHM as disclosed herein may also be used as a research tool.

In a further aspect, the MEHM obtained by the method as disclosed herein or the MEHM as disclosed herein for the use in medicine is also contemplated. In particular, the MEHM obtained by the method as disclosed herein or the MEHM as disclosed herein for use in heart repair is contemplated. For example, the MEHM may be an implant. Said implant may be used for the treatment of a patient suffering from heart failure. In a preferred embodiment, the MEHM is permanently applied to the heart of the patient. Such a permanent application of the MEHM to the heart may be achieved using standard surgical procedures such as sewing, stapling, or gluing. For example, the MEHM may be sewed to the heart of the patient.

Finally, a method of treating a subject suffering from heart failure is also disclosed, the method comprising administering to the heart of a patient a MEHM obtained by the method as disclosed herein. In a preferred embodiment, the method comprises attaching the MEHM to the heart of the subject, and wherein attaching preferably comprises sewing the MEHM onto the heart.

The invention is further described by the following embodiments:

1. A method of manufacturing a multilayer engineered heart muscle (MEHM), the method comprising the steps of:
   (i) providing a liquid reconstitution mixture in a mould, wherein said reconstitution mixture is perforated by at least two poles,
   wherein said reconstitution mixture comprises (a) collagen, (b) a cellular mixture of cardiac myocytes and non-myocytes and (c) a suitable reconstitution medium, whereby said reconstitution mixture undergoes gelation in the mould,
   (ii) culturing the mixture obtained by step (i) in said mould in a suitable culturing medium, whereby the reconstitution mixture compacts in the mould;
   (iii) a) adding a further liquid reconstitution mixture as defined in step (i) from the top and/or from the bottom to the compacted reconstitution mixture obtained by step (ii) whereby said further liquid reconstitution mixture undergoes gelation, followed by culturing under the same conditions as in step ii), whereby said further reconstitution mixture compacts in the mould; or
   b) transferring the compacted reconstitution mixture obtained by step (ii) into a different mould, wherein said reconstitution mixture is perforated by at least two poles, followed by carrying out step (iii) a) in said different mould;

thereby obtaining a multilayer engineered heart muscle (MEHM), preferably wherein the MEHM is thickened by repeating step (iii)a) and/or step (iii)b) at least once, and (iv) optionally culturing the MEHM of step (iii) in said mould in a suitable maturating medium, wherein the MEHM is capable of contracting.

2. The method of embodiment 1, wherein the ability of the MEHM to contract is assessed by visual inspection and/or by determining the capability of the reconstitution mixture of step (i) to form a force-generating engineered heart muscle by carrying out steps (i), (ii) and optionally (iv), and wherein the engineered heart muscle is capable of developing contractile forces of at least 0.05 mN force of contraction (FOC) as measured under standard isometric conditions in Supplementary FIG. 6C of Tiburcy et al. Circulation 135(19)1832-1847 (2017).

3. The method of embodiment 2, wherein the contraction of the MEHM is further determined by assessing in parallel the capability of the reconstitution mixture of step (i) to form a force-generating engineered human muscle in loop-format, as described in Tiburcy et al. Circulation 135(19)1832-1847 (2017), by carrying out steps (i), (ii) and (iv), and wherein the engineered heart muscle in loop-format generates at least mN force of contraction (FOC), as measured in Supplementary FIG. 6C of Tiburcy et al. Circulation 135(19)1832-1847 (2017).

4. The method of any of the preceding embodiments, wherein the MEHM generates a force of contraction (FOC) of at least 0.05 mN, more preferably at least 0.1 mN, more preferably at least 0.3 mN, more preferably at least 0.5 mN, more preferably at least 1 mN, more preferably at least 3 mN, even more preferably at least 5 mN, and most preferably at least 10 mN.

5. The method of any of the preceding embodiments, wherein each layer of the MEHM has a thickness of at least about 0.1 mm, of at least about 0.15 mm, of at least about 0.2 mm, of at least about 0.25 mm, of at least about 0.3 mm, of at least about 0.4 mm, or of least about 0.5 mm.

6. The method of any of the preceding embodiments, wherein the MEHM is from about mm to about 30 mm in thickness, preferably from about 0.3 mm to about 30 mm, preferably from about 0.5 mm to about 30 mm in thickness, more preferably from about 0.7 mm to about 25 mm, more preferably from about 0.9 mm to about 20 mm, more preferably from about 1.5 mm to about 17 mm, more preferably from about 2 mm to about 15 mm, more preferably from about 2.8 mm to about 14 mm, more preferably from about 3.3 mm to about 13 mm, more preferably from about 3.8 mm to about 12 mm, more preferably from about 4.2 mm to about 11 mm, more preferably from about 4.6 mm to about 10.5 mm, and most preferably from about 5 mm to about mm.

7. The method of any of the preceding embodiments, wherein the contraction of the MEHM is measured video-optically by fractional area change (FAC) measurements.

8. The method of any of the preceding embodiments, wherein the contraction is determined by fractional area change (FAC) measurements of the MEHM using the method described in Tiburcy et al. Circulation 135(19) 1832-1847 (2017), and wherein the fractional area change (FAC) is at least 0.5% upon electrical stimulation, preferably wherein the FAC is at least 0.7%, more preferably at least 1%, more preferably at least 2%, more preferably at least 3%, and even more preferably at least 5%.

9. The method of any of the preceding embodiments, wherein the reconstitution mixture has a pH from 7.0 to 7.8, preferably a pH from 7.2 to 7.6, more preferably from 7.3 to 7.5, and most preferably wherein the reconstitution mixture has a pH of around 7.4

10. The method of any of the preceding embodiments, wherein the reconstitution mixture provides a final concentration from 0.5 to 3 mg/ml collagen, preferably from 0.55 to 2.5 mg/ml collagen, more preferably from 0.6 to 2.2 mg/ml collagen, more preferably from 0.65 to 2 mg/ml collagen, more preferably from 0.7 to 1.75 mg/ml collagen, more preferably from 0.75 to 1.5 mg/ml collagen, more preferably from 0.8 to 1.2 mg/ml collagen, even more preferably from 0.85 to 1 mg/ml collagen and most preferably about 0.9 mg/ml collagen.

11. The method of any of the preceding embodiments, wherein the collagen of step (i) is selected from the group consisting of collagen type I, collagen type III, collagen type IV, collagen type V, collagen type VI, collagen type XII, collagen type XIII, collagen type XIV, collagen type XV and a mixture thereof.

12. The method of any of the preceding embodiments, wherein at least 90% of the collagen of the reconstitution mixture of step (i) is collagen type I.

13. The method of any of the preceding embodiments, wherein the collagen of the reconstitution mixture of step (i) is of medical grade.

14. The method of any of the preceding embodiments, wherein the collagen of the reconstitution mixture of step (i) is of bovine origin, equine origin, human origin, or marine origin, preferably wherein the collagen is of bovine origin.

15. The method of any of the preceding embodiments, wherein the collagen of the mixture of step (i) further comprises one or more additional extracellular matrix component other than collagen, preferably wherein said one or more additional matrix component is selected from natural-occurring or synthetic extracellular matrix components, more preferably wherein the extracellular matrix components is selected from the group consisting of elastin, laminin, entactin, nidogen, proteoglycans, glycosaminoglycans, and fibronectin or synthetic mimetics thereof.

16. The method of any of the preceding embodiments, wherein the cellular mixture in step (i) provides a final cell concentration in the reconstruction mixture of $1\text{-}26.5 \times 10^6$ cells per ml, preferably of $2\text{-}13.2 \times 10^6$ cells per ml, more preferably of $3\text{-}10 \times 10^6$ cells per ml, more preferably of $3.5\text{-}9 \times 10^6$ cells per ml, more preferably of $4\text{-}8 \times 10^6$ cells per ml, more preferably of $4.3\text{-}7 \times 10^6$ cells per ml, more preferably of $4.6\text{-}6 \times 10^6$ cells per ml, even more preferably of about $5 \times 10^6$ cells per ml.

17. The method of any of the preceding embodiments, wherein the cardiac myocytes are human cardiac myocytes.

18. The method of any of the preceding embodiments, wherein the cardiac myocytes are derived from embryonic stem cells, wherein the cells are not produced using a process which involves modifying the germ line genetic identity of human beings or which involves the use of a human embryo for industrial or commercial purposes.

19. The method of any of the preceding embodiments, wherein the cardiac myocytes are derived from induced pluripotent stem cells, parthenogenetic stem cells, programmed somatic cells, or adult stem cells, preferably wherein the cardiac myocytes are derived from induced pluripotent stem cells.

20. The method of any of the preceding embodiments, wherein the cardiac myocytes are obtained by serum-free differentiation, preferably wherein the cardiac myocytes are obtained by following the protocol of WO2015/040142 or alternative protocols such as reviewed in Burridge et al. (2012), Production of de novo cardiomyocytes: human pluripotent stem cell differentiation and direct reprogramming. Cell Stem Cell. 2012 Jan. 6; 10(1):16-28 or Zimmermann (2020).

21. The method of any of the preceding embodiments, wherein the cardiac myocytes are non-human primate stem cell-derived, fetal, or neonatal cardiac myocytes.

22. The method of any of the preceding embodiments wherein the cardiac myocytes express ACTN2, UN, RYR2, and troponins as determined by flow cytometry or RNA-sequencing.

23. The method of any of the preceding embodiments, wherein the cellular mixture of step (i) comprises at least 10% cardiac myocytes, preferably at least 20%, more preferably at least 30%, even more preferably at least 40%, and most preferably at least 50%.

24. The method of any of the preceding embodiments, wherein the contraction of the MEHM is caused by the cardiac myocytes thereby generating a contractile force development of the MEHM.

25. The method of any of the preceding embodiments, wherein the non-myocyte cells are selected from one or more of the group consisting of stromal cells, endothelial cells, smooth muscle cells, and mesenchymal stem cells, preferably wherein the non-myocytes are stromal cells or endothelial cells, more preferably wherein the non-myocytes are stromal cells, even more preferably wherein the stromal cells are cardiac stromal cells, even more preferably wherein the cardiac stromal cells have fibroblast properties, even more preferably wherein the cardiac stromal cells are fibroblasts.

26. The method of any of the preceding embodiments, wherein the non-myocytes express CD90, as determined by flow cytometry, preferably wherein the non-myocytes express CD90, CD74 and CD44, even more preferably wherein the non-myocytes excrete extracellular matrix proteins, in particular collagen, and/or express integrins to facilitate cell-matrix interactions, wherein the non-myocytes compact the reconstitution mixture.

27. The method of any of the preceding embodiments, wherein the non-myocytes are derived from embryonic stem cells, wherein the cells are not produced using a process, which involves modifying the germ line genetic identity of human beings or which involves the use of a human embryo for industrial or commercial purposes.

28. The method of any of the preceding embodiments, wherein the non-myocytes are derived from induced pluripotent stem cells, parthenogenetic stem cells, programmed somatic cells, adult stem cells, or mesenchymal stem cells, preferably wherein the non-myocytes are derived from induced pluripotent stem cells.

29. The method of any of the preceding embodiments, wherein the non-myocytes are derived from biopsies obtained from human subjects, preferably from patients, even more preferably from patients for autologous or allogeneic administration of MEHM.

30. The method of any of the preceding embodiments, wherein the non-myocytes are obtained by serum-free differentiation, preferably wherein the non-myocytes are obtained by following the protocol of EP20188364.2; Witty A D, Mihic A, Tam R Y, et al., Generation of the epicardial lineage from human pluripotent stem cells, Nat Biotechnol. 2014; 32(10): 1026-1035; Iyer D, et al., Robust derivation of epicardium and its differentiated smooth muscle cell progeny from human pluripotent stem cells. Development, 2015 Apr. 15; 142(8):1528-41; Bao X, et al., Long-term self-renewing human epicardial cells generated from pluripotent stem cells under defined xeno-free conditions, Nat Biomed Eng. 2016; 1; or Bao X, et al., Directed differentiation and long-term maintenance of epicardial cells derived from human pluripotent stem cells under fully defined conditions, Nat Protoc. 2017 September; 12(9):1890-1900.

31. The method of any of the preceding embodiments, wherein the non-myocytes of cellular mixture of step (i) are stromal cells, preferably wherein the stromal cells are human stromal cells.

32. The method of embodiment 31, wherein the cellular mixture of step (i) comprises at least 10% stromal cells, preferably at least 20%, more preferably at least 30%, even more preferably at least 40%, and even more preferably at least 50%.

33. The method of any of the preceding embodiments, wherein the non-myocytes, preferably the stromal cells, are capable of compacting the reconstitution mixture in step (ii).

34. The method of any of the preceding embodiments, wherein the reconstitution medium comprises (a) a basal medium, and (b) a serum-free supplement.

35. The method of embodiment 34, wherein the serum-free supplement provides a final concentration of 0.5-50 mg/ml albumin, 1-100 µg/ml transferrin, 0.1-10 µg/ml ethanol amine, 0.003-0.3 µg/ml sodium selenite, 0.4-40 µg/ml L-Carnitine HCl, 0.1-10 µg/ml Hydrocortisone, 0.05-5 µl/ml fatty acid supplement, and 0.0001-0.1 µg/ml triodo-L-thyronine (T3).

36. The method of embodiments 34 or 35, wherein the serum-free supplement further comprises one or more components selected from the group consisting of vitamin A, D-galactose, linoleic acid, linolenic acid, progesterone, and putrescine.

37. The method of any of embodiments 34-36, wherein the serum-free supplement is B27 supplement minus insulin.

38. The method of any of embodiments 34-37, wherein the serum-free supplement is 2-6% (v/v) B27 supplement minus insulin, preferably wherein the serum-free supplement is 4% (v/v) B27 supplement minus insulin.

39. The method of any of embodiments 34-38, wherein the basal medium in step (i) is selected from Iscove's medium, RPMI, αMEM, and DMEM or a mixture thereof, preferably wherein the basal medium is selected from Iscove's medium, RPMI, αMEM or a mixture thereof, more preferably wherein the basal medium is a mixture of Iscove's medium and RPMI.

40. The method of any of embodiments 34-39, wherein the reconstitution medium further comprises (c) 35-790 uM ascorbic acid, (d) 5-500 ng/ml IGF-1, (e) 0.3-26 ng/ml VEGF, (f) 0.5-53 ng/ml FGF-2, and (g) 0.5-10 ng/ml TGFβ1;

preferably wherein the reconstitution medium further comprises (c) 75-300 uM ascorbic acid, (d) 26-105 ng/ml IGF-1, (e) 1.3-5.2 ng/ml VEGF, (f) 2.6-10.5 ng/ml FGF-2, and (g) 1-6 ng/ml TGFβ1;

more preferably wherein the reconstitution medium further comprises (c) about 158 uM ascorbic acid, (d) about 53 ng/ml IGF-1, (e) about 2.6 ng/ml VEGF (f) about 5.3 ng/ml FGF-2, and about 3 ng/ml TGFβ1.

41. The method of embodiment 40, wherein the VEGF us VEGF$_{165}$.

42. The method of any of the preceding embodiments, wherein the mould is formed to facilitate the formation of a planar shaped EHM, a pouch-shaped EHM or a cylinder-shaped EHM.

43. The method of embodiment 42, wherein the mould formed to facilitate the formation of a planar shaped EHM, preferably wherein the mould has the form of a disc, preferably wherein the disc has the form of a circular or polygonal disc, more preferably wherein the mould has the form of a hexagonal disc, and most preferably wherein the disc has a patch-like shape; or wherein the mould forms a confined three-dimensional space, preferably wherein the three-dimensional space has the form of a circular or polygonal three-dimensional space, more preferably wherein the mould has the form of a hexagonal three-dimensional space, even more preferably wherein the three-dimensional space has a patch-like shape.

44. The method of embodiment 42, wherein the mould is formed to facilitate the formation of pouch-shaped EHM, preferably wherein the mould has the form of a pouch, more preferably wherein the mould has the form of a sphere-shaped or an ellipsoid-shaped pouch, and even more preferably wherein the mould is formed by an inner and outer sphere- or ellipsoid-shaped wall, more preferably wherein the inner sphere- or ellipsoid-shaped wall is inflatable.

45. The method of embodiment 42, wherein the mould is formed to facilitate the formation of a cylinder shaped EHM, preferably wherein the mould has the form of a cylinder, more preferably wherein the mould is a cylindrical mould, more preferably wherein the cylindrical mould is formed by an inner and outer cylindrical wall; or wherein the cylindrical mould is formed by a single cylindrical wall and wherein the cylindrical mould is covered with reconstitution mixture by centrifugation.

46. The method of any of the preceding embodiments, wherein the reconstitution mixture is perforated by at least two poles and wherein the poles are flexible and thereby capable of introducing mechanical load on the MEHM.

47. The method of any of the preceding embodiments, wherein the poles are capable of allowing perfusion of the MEHM with culturing medium in step (ii), (iii) and optionally with maturating medium in step (iv), and with oxygen in steps (ii), (iii) and optionally (iv), preferably wherein the culturing medium perfusion and maturating medium perfusion leads to a nutrient support of the cardiac myocytes and non-myocytes during steps (ii), (iii) and/or optionally (iv).

48. The method of any of the preceding embodiments, wherein the reconstitution mixture is perforated by the at the least two poles from the bottom or from the top, preferably wherein the reconstitution mixture is perforated throughout its thickness.

49. The method of embodiment 48, wherein the at least two poles perforate the reconstitution mixture from the bottom and wherein the mould has the form a disc, preferably wherein the at least two poles extend from the bottom of the mould through the reconstitution mixture, more preferably wherein the poles are permanently attached to the mould or a base plate, more preferably wherein the poles are permanently attached to the casting area of the mould or to a removable base plate of the mould, even more preferably wherein (a) the mould and the at least two poles or (b) the removable base plate and the at least two poles are 3D-printed as one entity.

50. The method of embodiment 48, wherein the at least two poles perforate the reconstitution mixture from the top and wherein the mould has the form of a disc, preferably wherein the at least two poles are inserted into the liquid reconstitution mixture from the top.

51. The method of embodiment 48, wherein the at least two poles perforate the reconstitution mixture from the bottom and wherein the mould has the form of a pouch, preferably wherein the pouch is formed by an inner and outer sphere- or ellipsoid-shaped wall, more preferably wherein the at least two poles extend from the inner sphere-shaped or ellipsoid-shaped wall, more preferably wherein the poles are permanently attached to the inner sphere-shaped or ellipsoid-shaped wall.

52. The method of embodiment 48, wherein the at least two poles perforate the reconstitution mixture from the top and wherein the mould has the form of a pouch, preferably wherein the pouch is formed by an inner and outer sphere- or ellipsoid-shaped wall, more preferably wherein the at least two poles extend from the outer sphere-shaped or ellipsoid-shaped wall, more preferably wherein the poles are permanently attached to the outer sphere-shaped or ellipsoid-shaped wall.

53. The method of embodiment 48, wherein the at least two poles perforate the reconstitution mixture from the bottom, wherein the mould is a cylindrical mould and wherein the cylindrical mould is formed by an inner and outer cylindrical wall, preferably wherein the at least two poles extend from the outer cylindrical wall through the reconstitution mixture, more preferably wherein the poles are permanently attached to the outer cylindrical wall, and even more preferably wherein the outer cylindrical wall comprising the at least two poles is 3D-printed as one entity.

54. The method of embodiment 48, wherein the at least two poles perforate the reconstitution mixture from the top, wherein the mould is a cylindrical mould and wherein the cylindrical mould is formed by an inner and outer cylindrical wall, preferably wherein the at least two poles extend from the inner cylindrical wall through the reconstitution mixture, more preferably wherein the poles are permanently attached to the inner cylindrical wall, and even more preferably wherein the inner cylindrical wall comprising the at least two poles is 3D-printed as one entity.

55. The method of any of the preceding embodiments, wherein each reconstitution mixture has a volume of 0.5-200 ml, preferably 1-150 ml, more preferably 1.5-100 ml, more preferably 2-50 ml, more preferably 2.5-40 ml, more preferably 3-30 ml, more preferably 3.5-25 ml, more preferably 4-20 ml, more preferably 4.5-15 ml, more preferably 5-11.5 ml, more preferably 6-9.5 ml, even more preferably 6.5-8.5, and most preferably about 8 ml.

56. The method of any of the preceding embodiments, wherein the mould holds a volume of 1-400 ml, preferably of 2-300 ml, more preferably of 3-200 ml, more preferably of 4-100 ml, more preferably of 5-80 ml, more preferably of 6-60 ml, more preferably of 6.5-50 ml, more preferably of 7-40 ml, more preferably of 7.5-30 ml, more preferably of 8-23 ml, more preferably of 13-19 ml even more preferably of 13-17 ml, even more preferably about 15 ml, and most preferably wherein the mould is used for the formation of an EHM, which is patch-shaped, pouch-shaped or cylinder-shaped.

57. The method of any of the preceding embodiments, wherein the mould has a size of 1-400 $cm^2$, preferably of 2-300 $cm^2$, more preferably of 3-200 $cm^2$, more preferably of 4-100 $cm^2$, more preferably of 5-80 $cm^2$, more preferably of 6-60 $cm^2$, more preferably of 7-50 $cm^2$, more preferably of 8-40 $cm^2$, more preferably of 9-30 $cm^2$, more preferably of 10-23 $cm^2$, more preferably of 12-19 $cm^2$ even more preferably of 13-17 $cm^2$, even more preferably about 16 $cm^2$, and most preferably wherein the mould is used for the formation of an EHM in patch-shape.

58. The method of any of the preceding embodiments, wherein the reconstitution mixture is perforated by at least three poles.

59. The method of any of the preceding embodiments, wherein the poles are arranged as a grid, preferably wherein the poles are arranged as a triangular or rectangular grid, preferably as a triangular grid.

60. The method of any of the preceding embodiments, wherein the reconstitution mixture is perforated by at least 5 poles, more preferably at least 7 poles, more preferably at least 14 poles, even more preferably at least 20 poles, even more preferably at least 30 poles, even more preferably at least 37 poles, most preferably at least 52 poles, and most preferably at least 61 poles.

61. The method of any of the preceding embodiments, wherein each pole has a base area and wherein the base are is circular, rectangular, elliptical, triangular or polygonal, preferably wherein the base area is circular.

62. The method of any of the preceding embodiments, wherein poles have similar or different elastic properties.

63. The method of any of the preceding embodiments, wherein the elastic properties of the poles are defined by the working spring rate at the point at which the MEHM is in contact with the poles, preferably wherein the restoring force is from 0.5 to 50 mN/mm, more preferably from 0.7 to 40 mN/mm, even more preferably from 0.9 to 30 mN/mm, even more preferably from 1 to 20 mN/mm, even more preferably from 2 to 10 mN/mm, even more preferably from 3 to 5 mN/mm, and most preferably about 4 mN/mm.

64. The method of any of the preceding embodiments, wherein the elastic properties of the poles mimic the wall tension in the human heart, preferably wherein the wall tension is 1 to 20 kPa.

65. The method of any of the preceding embodiments, wherein the elastic properties of poles exhibit varying elastic moduli to establish biomechanical anisotropy.

66. The method of any of embodiments 1-64, wherein elastic properties of the poles exhibit similar elastic moduli to establish biomechanical isotropy.

67. The method of any of the preceding embodiments, wherein the poles are surrounded by a circumferential wall in the lower part of the poles, wherein the circumferential wall forms a ring-shaped ramp around the poles, and wherein the ring-shaped ramp tapers from the bottom upwards.

68. The method of any of the preceding embodiments, wherein the poles taper conically, and wherein the poles have the largest diameter at the bottom.

69. The method of any of the preceding embodiments, wherein the poles have a diameter of 0.5 to 3 mm, preferably of 0.6 to 2.5 mm, more preferably of 0.65 to 2 mm, even more preferably of 0.7-1.7 mm, and even more preferably of about 0.8-1.5 mm.

70. The method of embodiment 69, wherein the reconstitution mixture is perforated by at least seven poles, wherein the poles are arranged in a grid and wherein the diameters of the poles form a gradient along one planar axis, in particular as depicted in FIG. 7C, preferably whereby the measured FAC along the gradient is larger than the measured FAC along poles with an equal pole thickness.

71. The method of any of the preceding embodiments, wherein step (i), (ii), and/or optionally (iv) is carried out at a temperature range of 36.4-37.6° C., preferably at a temperature range of 36.6-37.4° C., preferably at a temperature range of 36.8-37.2° C., more preferably at about 37° C.

72. The method of any of the preceding embodiments, wherein step (i), (ii), and/or optionally (iv) is carried out in a humidified cell culture incubator in the presence of 2-10% $CO_2$, preferably 2.5-8% $CO_2$, more preferably 3-7% $CO_2$, even more preferably 3.5-6.5% $CO_2$, even more preferably 4-6% $CO_2$ and most preferably about 5% $CO_2$.

73. The method of any of the preceding embodiments, wherein step (i), (ii), and/or optionally (iv) is carried out in a humidified cell culture incubator in the presence of 5-40% $O_2$, preferably 10-30% $O_2$, more preferably 15-35% $O_2$, even more preferably 17-33% $O_2$, even more preferably 19-25-% $O_2$ and most preferably about 21% $O_2$.

74. The method of any of the preceding embodiments, wherein the gelation in step (i) is characterized in that the reconstitution mixture obtained by step (i) is gel-like.

75. The method of any of the preceding embodiments, wherein the gelation in step (i) is characterized in that the culturing medium surrounds the reconstitution mixture and does not dissolve the reconstitution mixture, if added to the mould.

76. The method of any of the preceding embodiments, wherein the gelation in step (i) is characterized in that the reconstitution mixture is opaque, preferably as determined by visual inspection as shown in FIG. 3B of Tiburcy M, Meyer T, Soong P L, Zimmermann W H. Collagen-based engineered heart muscle. Methods Mol Biol. 2014; 1181:167-76.

77. The method of any of the preceding embodiments, wherein step (i) is carried out for at least 15 minutes, preferably for at most 24 hours, more preferably from 20 minutes to hours, more preferably from 30 minutes to 8 hours, even more preferably from 45 minutes to 1.5 hours, and most preferably for about 1 hour.

78. The method of any of the preceding embodiments, wherein the culturing medium in step (ii), comprises (a) a basal medium, (b) a serum-free supplement, (c) L-glutamine, (d) ascorbic acid, (e) IGF-1, (f) VEGF, and (g) TGFβ1.

79. The method of embodiment 78, wherein (a) the basal medium is selected from Iscove's medium, αMEM, DMEM, and RPMI, preferably wherein the basal medium is Iscove's medium or αMEM, more preferably wherein the basal medium is Iscove's medium.

80. The method of embodiment 78 or 79, wherein (b) the serum-free supplement is defined in any of embodiments 35-38.

81. The method of any of embodiment 78-80, wherein the culturing medium in step (ii) comprises 0.4-10 mM L-glutamine, preferably 0.8-6 mM L-glutamine, more preferably 1.2-5 mM L-glutamine, more preferably 1.5-4 mM L-glutamine, more preferably 1.7-3 mM L-glutamine and most preferably about 2 mM L-glutamine.

82. The method of any of embodiment 78-81, wherein the culturing medium in step (ii) comprises 30-3000 μM ascorbic acid or a derivative thereof, preferably 100-1000 μM ascorbic acid or a derivative thereof, more preferably 180-500 μM ascorbic acid or a derivative thereof, more preferably 220-370 μM ascorbic acid or a derivative thereof, more preferably 270-330 μM ascorbic acid or a derivative thereof and most preferably about 300 μM ascorbic acid or a derivative thereof.

83. The method of embodiment 82, wherein the derivative of ascorbic acid is ascorbate-2-phosphate.

84. The method of any of embodiment 78-83, wherein the culturing medium in step (ii) comprises 10-1000 ng/ml IGF1, preferably 50-500 ng/ml IGF1, more preferably 70-200 ng/ml IGF1, even more preferably 90-120 ng/ml IGF1, and most preferably about 100 ng/ml IGF1.

85. The method of embodiment 84, wherein the IGF1 is human IGF1.

86. The method of any of embodiment 78-85, wherein the culturing medium in step (ii) comprises 2.5-10 ng/ml VEGF, preferably 3-9 ng/ml VEGF, more preferably 3.5-8 ng/ml VEGF, more preferably 4-7 ng/ml VEGF, more preferably 4.5-6 ng/ml VEGF, most preferably about 5 ng/ml VEGF.

87. The method of embodiment 86, wherein the VEGF is human VEGF, preferably wherein VEGF is VEGF$_{165}$.

88. The method of any of embodiment 78-87, wherein the culturing medium in step (ii) comprises 5-20 ng/ml FGF, preferably 6-18 ng/ml FGF, more preferably 7-16 ng/ml FGF, more preferably 8-14 ng/ml, more preferably 9-12 ng/ml FGF, most preferably about 10 ng/ml FGF.

89. The method of any of embodiments 78-88, wherein the FGF-2 is human FGF-2.

90. The method of any of embodiments 78-89, wherein the culturing medium in step (ii) comprises 2-8 ng/ml TGFβ1, preferably 3-7 ng/ml TGFβ1, more preferably 4-6 ng/ml TGFβ1, even more preferably 4.5-5.5 ng/ml TGFβ1, even more preferably about 5 ng/ml TGFβ1, and most preferably wherein the TGFβ1 is human TGFβ1.

91. The method of any embodiments 78-90, wherein the culturing medium in step (ii) comprises about 750 mg/L glycine, about 890 mg/L L-alanine, about 1320 mg/L L-asparagine, about 1330 mg/L L-aspartic acid, about 1470 mg/L L-glutamic acid, about 1150 mg/L L-proline, and about 1050 mg/L L-serine.

92. The method of any of the preceding embodiments, wherein the reconstitution mixture in step (ii) compacts by at least about 20% of the original reconstitution mixture volume, preferably by at least about 25%, more preferably by at about least 30%, more preferably by at least about 40%, more preferably by at least about 50%, more preferably by at least about 60%, more preferably by at least about 70%, more preferably by at least about 80%, even more preferably by at least about 90%, as preferably determined by visual inspection or video-optic analysis of the EHM volume.

93. The method of any of the preceding embodiments, wherein the completion of step (ii) is determined by generating an engineered heart muscle (EHM) in loop format in parallel to the MEHM by following steps (i) and (ii) and by determining the detachment of the engineered heart muscle (EHM) in loop-format from the mould after completion of step (ii), as described in in FIG. 3C of Tiburcy M, Meyer T, Soong P L, Zimmermann W H. Collagen-based engineered heart muscle. Methods Mol Biol. 2014; 1181:167-176.

94. The method of any of the preceding embodiments, wherein step (ii) is carried out for at least 12 hours, preferably for at most 15 days, more preferably 12 hours to 7 days, preferably from 14 hours to 6 days, more preferably from 16 hours to 5.5 days, more preferably from 18 hours to 5 days, more preferably from 20 hours to 4.5 days, even more preferably from 22 hours to 4 days, even more preferably from 23 hours to 3.5 days, and most preferably from 24 hours to 3 days.

95. The method of any of the preceding embodiments, wherein in step (iii)a) one further reconstitution mixture is added on top of the compacted reconstitution mixture of step (ii).

96. The method of any of the embodiments 1-94, wherein in step (iii)a) one further reconstitution mixture is added from the bottom to the compacted reconstitution mixture of step (ii).

97. The method of any of the embodiments 1-94, wherein in step (iii)a) one further reconstitution mixture is added to coat the compacted reconstitution mixture of step (ii) from top and bottom simultaneously.

98. The method of any of the preceding embodiments, wherein in step (iii)a) the further reconstitution mixture coats the compacted reconstitution mixture of step ii) from the top and/or the bottom, preferably wherein the surface area of the compacted reconstitution mixture of step (ii) and the further reconstitution mixture of step (iii)a) is the same.

99. The method of any of embodiments 1-97, wherein in step (iii)a) the further reconstitution mixture coats a restricted area of the compacted reconstitution mixture of step ii) from the top or the bottom, preferably wherein the surface area of the further reconstitution mixture of step (iii)a) is smaller than the surface area of the reconstitution mixture of step (ii).

100. The method of any of embodiments 1-97, wherein in step (iii)b) the different mould has a larger casting area than the mould of step (i), preferably wherein in step (iii)b) the further reconstitution mixture coats at least the compacted reconstitution mixture of step (ii) from the top or from the bottom, more preferably wherein in step (iii)b) the further reconstitution mixture coats the compacted reconstitution mixture of step (ii) from the top or from the bottom and fills the larger casting area of the different mould, more preferably wherein the surface area of the further reconstitution mixture of step (iii)b) is larger than the surface area of the compacted reconstitution mixture of step (ii).

101. The method of any of the preceding embodiments, wherein step (iii)a) or step (iii)b) is repeated at least 2 times, preferably at least 3 times, more preferably at least 4 times, more preferably at least 5 times, more preferably at least 6 times, more preferably at least 7 times, more preferably at least 8 times, even more preferably at least 9 times, and most preferably at least 10 times.

102. The method of any of the preceding embodiments, wherein step (iii)a) or step (iii)b) is repeated 2-200 times, preferably 2-100 times, more preferably 2-80 times, more preferably 2-70 times, more preferably 2-60 times, more preferably 2-50 times, more preferably 2-40 times, more preferably 3-30 times, more preferably 3-25 times, more preferably 4-20 times, more preferably 4-15 times, more preferably 4-10 times, even more preferably 5-9 times, and most preferably 5-8 times.

103. The method of any of the preceding embodiments, wherein the maturating medium in step (iv) is defined as the culturing medium in any of embodiments 60-71 and 73, except that TGFβ1 is omitted from the maturating medium compared to the culturing medium.

104. The method of any of the preceding embodiments, wherein step (iv) is carried out for 4-200 days, preferably 6-150 days, more preferably 8-120 days, more preferably 9-110 days, more preferably 10-90 days, more preferably 15-70 days, more preferably 20-50 days, and most preferably 28-42 days.

105. The method of any of the preceding embodiments, wherein in step (iv) the MEHM of step (iii) is cultured in a suitable maturating medium, whereby the MEHM of step (iv) exhibits an increased force development when compared to the MEHM of step (iii), wherein the increased force development is determined by a fractional area change (FAC) measurement using the method described in Tiburcy et al., Circulation 135(19) 1832-1847 (2017), and wherein the fractional area change (FAC) of the MEHM of step (iv) is at least 0.5% upon electrical stimulation, preferably at least 1%, more preferably at least 1.2%, more preferably at least 1%, more preferably at least 2%, more preferably at least 3%, and even more preferably at least 5%.

106. The method of any of the preceding embodiments, wherein the cardiac myocytes in the MEHM are sufficiently supplied with oxygen, preferably wherein the oxygen supply is determined by the ODD-Luc hypoxia reporter as described in Hesse A R, Levent E, Zieseniss A, Tiburcy M, Zimmermann W H, Katschinski D M: Lights on for HIF-1α: Genetically Enhanced Mouse Cardiomyocytes for Heart Tissue Imaging. Cell Physiol Biochem 2014; 34:455-462.

107. The method of any of the preceding embodiments, wherein the cardiac myocytes in the MEHM are sufficiently supplied with oxygen, which is determined by the ODD-Luc hypoxia reporter as described in Hesse A R et al. (2014), preferably wherein a sufficient oxygen supply is ensured if the mean relative luminescence of cardiac myocytes of the MEHM is at most 6-fold higher than in a single-layer EHM as obtained by following steps (i), (ii) and optionally (iv) of the method, more preferably at most 5-fold, more preferably at most 4-fold, more preferably at most 3-fold, more preferably at most 2.5-fold, even more preferably at most 2-fold, and even more preferably at most 1.5-fold.

108. The method of any of the preceding embodiments, wherein the cardiac myocytes in the MEHM are sufficiently supplied with oxygen, which is determined by the ODD-Luc hypoxia reporter as described in Hesse A R et al. (2014), and wherein the mean relative luminescence of cardiac myocytes of the MEHM is not greater than the mean relative luminescence measured in cardiac myocytes of a single-layer EHM.

109. A multilayer engineered heart muscle (MEHM) obtained by a method according to any one of embodiments 1-108.

110. A multilayer engineered heart muscle (MEHM) obtainable by a method according to any one of embodiments 1-108.

111. A multilayer engineered heart muscle (MEHM), preferably an engineered heart patch, an engineered heart pouch, or an engineered heart cylinder, wherein the MEHM comprises (a) collagen and (b) a cellular mixture of cardiac myocytes and non-myocytes, and wherein the MEHM comprises at least 2 layers.

112. The MEHM of embodiment 111, wherein the MEHM has a thickness of at least 0.2 mm.

113. The MEHM of embodiments 111 or 112, wherein the MEHM has been generated by a repetitive and sequential layering method,
wherein the MEHM originates from 2-200 layers,
wherein the layers have been merged to each other and thereby expand the MEHM thickness.

114. The MEHM of any of embodiments 111-113, wherein each layer originates from a reconstitution mixture
wherein each reconstitution mixture comprises (a) collagen, (b) a cellular mixture of cardiac myocytes and non-myocytes and (c) a suitable reconstitution medium, and
wherein the MEHM is capable of contracting, as measured by determining the fractional area change (FAC) of the MEHM using the method described in Tiburcy et al., Circulation 135(19)1832-1847 (2017).

115. The MEHM of any of embodiments 111-114, wherein the MEHM originates from 2-100 layers, preferably 2-80 layers, more preferably 2-70 layers, more preferably 2-60 layers, more preferably 2-50 layers, more preferably 2-40 layers, more preferably 3-30 layers, more preferably 3-25 layers, and even more preferably 4-20 layers.

116. The MEHM of any of embodiments 111-115, wherein the FAC is at least 0.5% upon electrical stimulation, preferably wherein the FAC is at least 0.7%, more preferably at least 1%, more preferably at least 2%, more preferably at least 3%, and even more preferably at least 5%.

117. The MEHM of any one of embodiments 111-116, wherein the MEHM is from 0.2 mm to about 30 mm in thickness, preferably from about 0.3 mm and to about 30 mm, more preferably from about 0.5 mm to about 30 mm, more preferably from about 0.7 mm to from about 25 mm, more preferably from about 0.9 mm to about 20 mm, more preferably from about 1 mm to about 17 mm, more preferably from about 2.3 mm to about 15 mm, more preferably from about 2.8 mm to about 14 mm, more preferably from about 3.3 mm to about 13 mm, more preferably from about 3.8 mm to about 12 mm, more preferably from about 4.2 mm to about 11 mm, more preferably from about 4.6 mm to about 10.5 mm, and most preferably from about 5 mm to about 10 mm.

118. The MEHM of any one of embodiments 111-117, wherein the MEHM is not vascularized and/or the MEHM is not under the control of the central nervous system.

119. The MEHM of any one of embodiments 111-118, wherein the MEHM is perforated by at least 2 poles with similar diffusion distances throughout the MEHM to ensure nutrient and oxygen supply of the cellular mixture.

120. The MEHM of any one of embodiments 111-119, wherein the cardiac myocytes in the MEHM are sufficiently supplied with oxygen, preferably wherein the oxygen supply is determined by the ODD-Luc hypoxia reporter as described in Hesse A R, Levent E, Zieseniss A, Tiburcy M, Zimmermann W H, Katschinski D M: Lights on for HIF-1α: Genetically Enhanced Mouse Cardiomyocytes for Heart Tissue Imaging. Cell Physiol Biochem 2014; 34:455-462

121. The MEHM of any one of embodiments 111-120, wherein the cardiac myocytes in the MEHM are sufficiently supplied with oxygen, which is determined by the ODD-Luc hypoxia reporter as described in Hesse A R et al. (2014), preferably wherein a sufficient oxygen supply is ensured if the mean relative luminescence of cardiac myocytes of the MEHM is at most 6-fold higher than in a single-layer EHM as obtained by following steps (i), (ii) and optionally (iv) of the method, more preferably at most 5-fold, more preferably at most 4-fold, more preferably at most 3-fold, more preferably at most 2.5-fold, even more preferably at most 2-fold, and even more preferably at most 1.5-fold.

122. The MEHM of any one of embodiments 111-121, wherein the cardiac myocytes in the MEHM are sufficiently supplied with oxygen, which is determined by the ODD-Luc hypoxia reporter as described in Hesse A R et al. (2014), and wherein the mean relative luminescence of cardiac myocytes of the MEHM is not greater than the mean relative luminescence measured in cardiac myocytes of a single-layer EHM.

123. The MEHM of any one of embodiments 111-122, wherein the MEHM is obtained by any one of the methods according to embodiments 1-95.

124. A multilayer engineered heart muscle (MEHM) obtained by a carrying out steps (i)-(iii) of the method according to any one of embodiments 1-102.

125. An engineered heart muscle (EHM), preferably an engineered heart patch, engineered heart pouch, or engineered heart cylinder, wherein the EHM comprises (a) collagen, (b) a cellular mixture of cardiac myocytes and non-myocytes and wherein the EHM has a thickness of at least about 0.6 mm, preferably wherein the EHM has a thickness of at least about of least 0.61 mm, of at least 0.62 mm, of at least 0.63 mm, of at least 0.64 mm, of least 0.65 mm, of at least 0.66 mm, of at least 0.67 mm, of at least 0.68 mm, of at least 0.69 mm, of at least 0.7 mm, of at least 0.8 mm or of at least 0.9 mm.

126. The EHM of embodiment 125, wherein the EHM is a multilayer EHM and comprises at least 2 layers.

127. Use of the MEHM obtained by the method according to any of embodiments 1-108 or the MEHM according to any one of embodiments 109-126 in an in vitro model for drug screening.

128. The use of embodiment 127 in an in vitro model for drug toxicity screening or drug efficacy screening.

129. Use of the MEHM obtained by the method according to any of embodiments 1-108 or the MEHM according to any one of embodiments 109-126 in an in vitro manufacture of an engineered human myocardium, preferably wherein the MEHM has the three-dimensional shape to match patient-specific myocardial defect, more preferably wherein the patient-specific myocardial defect is assessed by MRI, ultrasound, computer tomography, positron emission tomography and/or optical coherence tomography.

130. Use of the MEHM obtained by the method according to any of embodiments 1-108 or the MEHM according to any one of embodiments 109-126 as a research tool.

131. A multilayer EHM (MEHM) obtained by the method according to any one of embodiments 1-108 or the MEHM according to any one of embodiments 109-126 for the use in medicine.

132. A multilayer EHM (MEHM) obtained by the method according to any one of embodiments 1-108 or the MEHM according to any one of embodiments 109-126 for use in heart repair, preferably for the treatment of a patient suffering from heart failure.

133. The MEHM of embodiment 132, wherein the MEHM is permanently applied to the heart of the patient, preferably wherein the MEHM is sewed to the heart of the patient.

134. A method of treating a subject suffering from heart failure, the method comprising administering to the heart of a patient a MEHM obtained by the method according to any of embodiments 1-108 or as defined in any one of embodiments 109-126.

135. The method of embodiment 134, wherein the method comprises attaching the MEHM to the heart of the subject, and wherein attaching preferably comprises sewing the MEHM onto the heart.

Of course all embodiments as disclosed herein can be applied alone or in combination with other embodiments. Furthermore, all embodiments as disclosed herein apply to the method of manufacturing a MEHM as well as to the MEHM and the in vitro and in vivo uses of the MEHM.

EXAMPLES

The following examples are intended to illustrate the invention further, but are not limited to it. The examples describe technical features, and the invention also relates to combinations of the technical features presented in this section.

Figure 2:
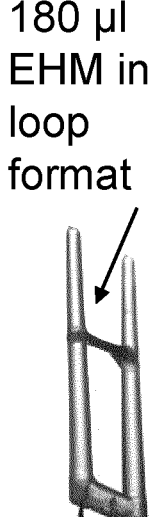
FIG. 2: Scalability of engineered heart muscle. Photographs depict typical engineered heart muscle formats used by the inventors for disease modelling, drug screening and heart repair. The indicated volumes represent the initial volumes of the respective engineered heart muscle reconstitution mixtures. In a layering approach in order to generate an MEHM as disclosed herein, each reconstitution mixture may have these exemplary volumes. Mechanical loading is realized by the integration of flexible poles into the respective tissue formulations. Geometries and scale can be further adapted as needed. After completion of the self-organization process of one layer EHM thickness (z-dimension) is typically 0.5±0.1 mm in the displayed formulations. By repetitive layering, as disclosed herein, the MEHM is thickened and enforced. Scale bar: 1 cm.
Figure 2:
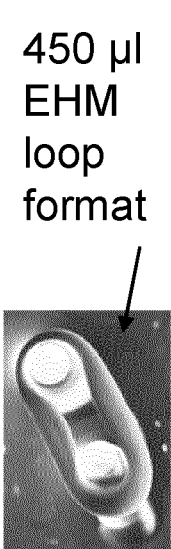
Figure 2:
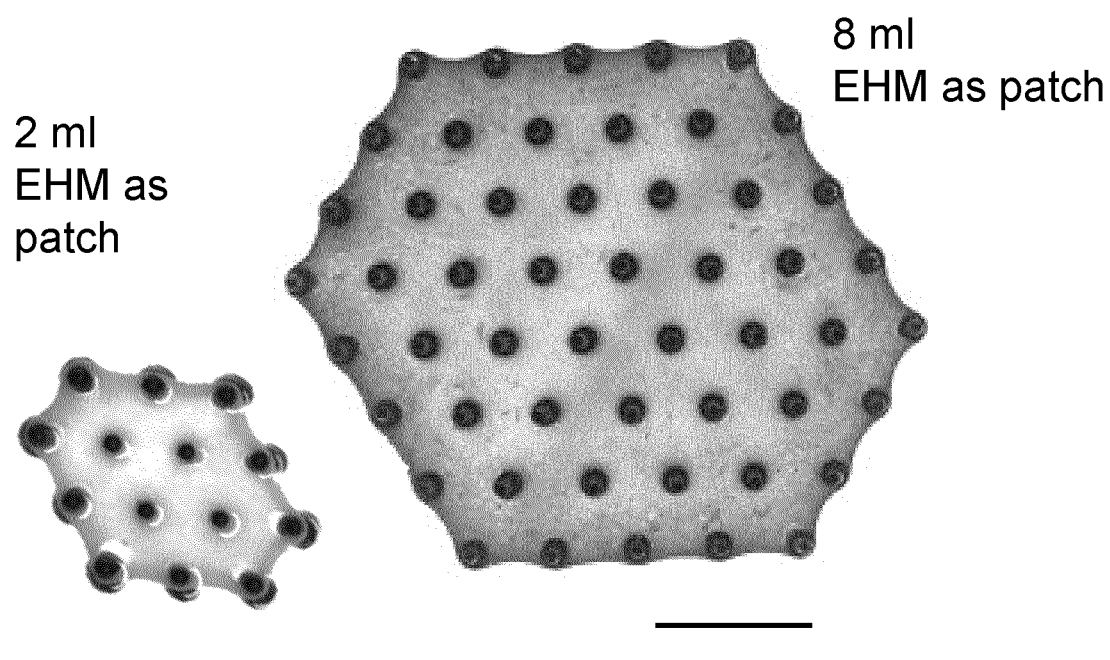

Example 1—Scalable Production of Engineered Heart Muscle (EHM) in Loop-Format and Patch Format As previously described by the inventors in Tiburcy et al. (2017) and Tiburcy et al. (2020), engineered human myocardium can be produced in a loop format and as patches. In particular for the in vivo use for heart repair, the engineered heart patches is of prime importance. FIG. 2 provides an overview, of different sizes and formats, which have been produced and published previously (Tiburcy et al. (2017) and Tiburcy et al. (2020)).

Example 2—Scaling of EHM Thickness by Sequential and Repetitive Layering Supported by Perforating Poles Ensuring Mechanical Loading and Sufficient Supply of Oxygen and Nutrients For the production of heart muscle for the treatment of patients with heart failure, an engineered heart muscle ideally needs to support the force of a beating human heart. The cardiac wall to be treated is typically 5-10 mm thick in the patient, i.e., an implant ideally reaches this thickness and is geometrically adaptable to meet the specific patient demands for mechanical support of the underperforming heart wall.

Figure 1:
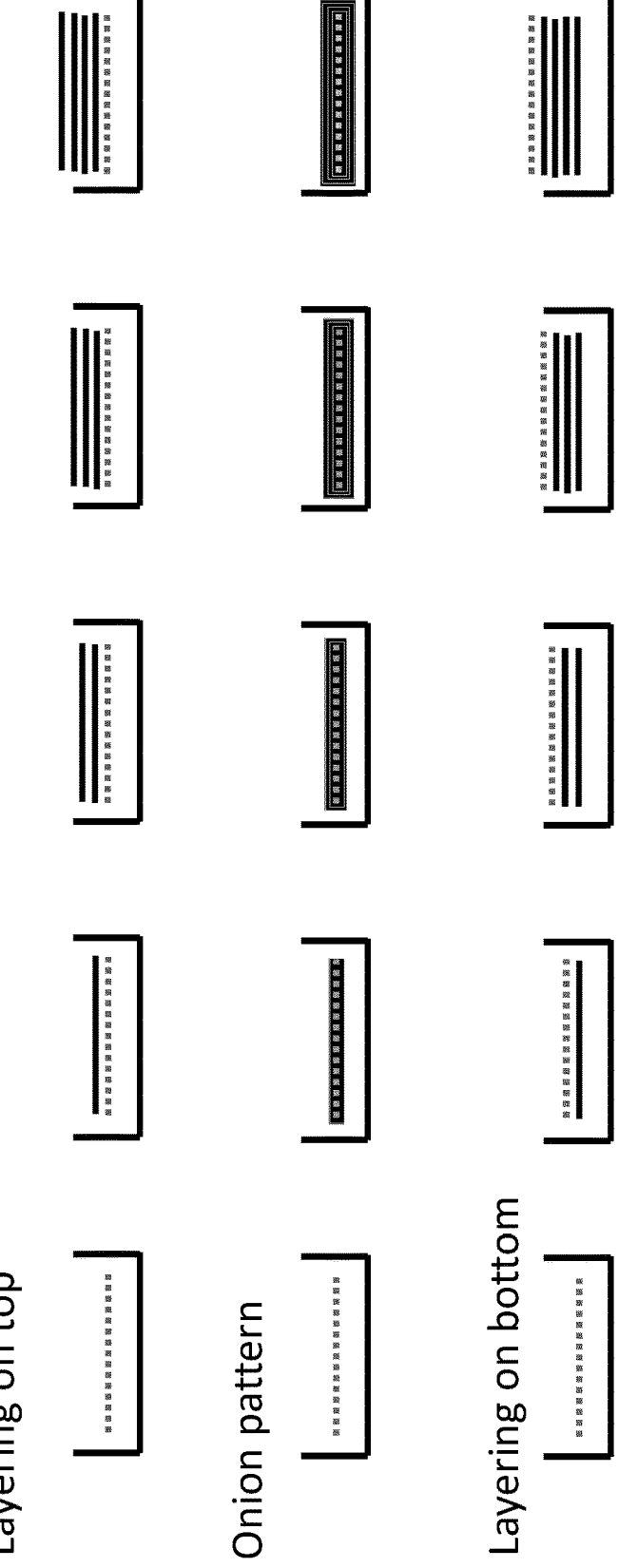
FIG. 1: Overview of repetitive layering to obtain a multilayer engineered heart muscle (MEHM) as disclosed herein. Generally, the newly added layer (reconstitution mixture) merges to the previous layer (compacted reconstitution mixture). By repetitive layering, a thick and enforced engineered heart muscle is obtained. A "Layering on top" is obtained by adding a new reconstitution mixture on top of the compacted reconstitution mixture. An "Onion pattern" is obtained by immersing the first and consecutively formed stacks of merged layers in newly added reconstitution mixture. A "Layering from the bottom" is obtained by adding a new reconstitution mixture from the bottom to the compacted reconstitution mixture. This layering can be repeated indefinitely considering oxygen and nutrient diffusion requirements of the embedded cells. Oxygen and nutrient supply is achieved by immersion in nutrient (in particular glucose, lactate, and/or fatty acids) containing oxygenated culturing medium and an increased tissue surface area by design, i.e., by the creation of channels via perforating poles (not shown in schematic; refer to FIGS. 2 and 3). The initial first layer is indicated as a dotted line; subsequent layers are indicated in black.

In order to generate a thickened (and enforced) multilayer EHM, the inventors developed a sequential and repetitive layering method. Specifically, FIG. 1 shows three different ways of repetitive and sequential layering in order to obtain a thickened engineered heart patch (note that for simplification perforating poles are excluded). As a general principle, the first reconstitution mixture, after compaction to a defined layer, is coated by additional reconstitution mixtures. Coating can be from the top, from the bottom, or from both sides as schematically shown in FIG. 1. The process is repeated until the desired tissue thickness is achieved. By design of the casting mould, any shape and desired x-y dimensions can be created (individualized patch design). A prerequisite for the coating/layering process is that the first and subsequently produced layers form a compact tissue. This compact tissue formation is achieved by repetitive and sequential layering as the individual reconstitution mixtures merge to each other. Tissue compaction is a function of the stroma cell type and content (Tiburcy et al. (2017), Schlick et al. (2019)). Stroma cell type and content are chosen to reach ≥20% compaction of the original reconstitution mixture (FIG. 5B-C demonstrates the EHM compaction in exemplarily in a loop format). This provides the structure and physical space to coat the compacting EHM with a further layer from the top and/or the bottom or a both surface coating layers. The inventors typically add new layers 24 h after casting of the previous layer. These times can be shortened or extended as desired and experimentally determined, as the desired tissue compaction process is dependent on the stroma cell type and density, the cell composition in general, and the hydrogel and culture medium composition (e.g., addition of effective TGFb1 concentrations can accelerate the process as exploited in Tiburcy et al. (2017) and WO2017/207431 for the formation of EHM). Further reconstitution mixtures may be added to the mould in order to coat the compacted, multi-layer engineered heart muscle. By performing this method, the EHM thickens layer-by-layer, so that a multi-layered EHM can reach the clinically desired thickness of 5 mm to 10 mm or even beyond. As the thickness of a human cell wall is between 5 mm to 10 mm, it is assumed that such a thickened heart patch is also able to sustain enough mechanical stability to support cardiac wall function. Furthermore, it is expected that the contractility of the cardiomyocytes embedded within the EHM support the contraction of the natural heart.

Figure 3:
FIG. 3: Scaling of EHM thickness by sequential/repetitive layering and sufficient supply of oxygen and nutrients. A: Custom-designed casting mould with stretch device (comprised of 3D-printed flexible poles with defined spacing fixed to a solid base plate) to enable the perforated EHM design and facilitate auxotonic contractions of the developing EHM or MEHM against a defined resistance. B: Schematic view of the layered perforated patch design. C: Top and side views of a 5-layered (left) and single-layered (right) EHM; the 5-layered EHM had a thickness of around 5-6 mm and the single-layered EHM has a thickness of around 1 mm. D: By making use of a human ODD-Luc hypoxia reporter iPSC line for the construction of a middle layer in the 5-layered construct (both, the 5-layered and single-layered EHM contain the same amount of ODD-Luc cardiomyocytes, Hesse et al. 2014 for the ODD-Lux hypoxia method), there was no evidence for enhanced hypoxia in the substantially thicker 5-layered design. The gray shade code on the right indicates low and high ODD-Luc activity as a sign of hypoxia sensing. The grey scale depicts luminescence of the reporter cell line. The intensity of the ODD-Luc signal was lower in the 5-layered EHM (left) compared to the background ODD-Luc signal in the single patch (right). In other words, the intensity of the luminescent signal appears to be at least the same in the single-layered EHM compared to the multi-layered EHM, if not brighter in the single-layered EHM. Thus, the 5-layered EHM does not suffer from hypoxia.

FIG. 3A depicts a casting mould with stretch device (comprised of 3D-printed flexible poles with defined spacing fixed to a solid removable base plate) to enable the perforated EHM design and facilitate auxotonic contractions of the developing patch against a defined resistance. Of course, the size of the casting mould as well as the number of poles and the size of the poles can be adapted. FIG. 3B shows a schematic overview of a multi-layered EHM as disclosed herein. In FIG. 3C, a generated 5-layered EHM and a single-layered EHM is shown next to each other. In the lower panel of FIG. 3C, the thickness of the EHM is compared specifically demonstrating that a 5-layered EHM is approximately 5-6 millimetres in thickness. By use of the introduced perforated layering design there is no limitation in overall tissue thickness with constant diffusion distances as a result of the channels produced by the perforating poles. Of course, pole distance and size can be adapted to increase channel number and alter channel size and inter-channel distance.

A key challenge in trying to obtain such a thick multilayer engineered heart muscle (MEHM) is to ensure the supply of oxygen and nutrients to the cells embedded in the engineered heart muscle. By the perforated EHM design, the inventors ensure a sufficient oxygen and nutrient supply in any given multilayer design. This is exemplified by studies of the inventors using a human ODD-Luc hypoxia reporter model (developed by the inventors based on previous experience in a mouse model; Hesse et al. (2014)). Cardiomyocytes derived from an ODD-Luc human pluripotent stem cell line in a single and 5-layer (5-6 mm thick) did not show differences in ODD-Luc signal intensity above background (reported in the single layer EHM). Channel diameter and density in the demonstrated EHM design was defined by pole diameter (1.5 mm) and pole circumference-to-circumference distance (3.5 mm). Under these conditions (effective maximal surface distance in the EHM is ≤1.75 mm) no hypoxia was observed. The perforated patch format contrasts the vascular density in the human heart (2.000-5.000 capillaries/mm$^2$, with an intercapillary distance of <25 μm). It was therefore surprising and also in contrast to theoretic assumptions that oxygen supply by diffusion over a distance of >100 μm would result in the sensing of hypoxic conditions by cardiomyocytes (Radisic et al. (2005). This discrepancy can be explained by the high hypoxia resistance in pluripotent stem cell derived cardiomyocytes in the presence of nutrient (glucose, lactate, and/or fatty acids)-containing culture medium.

By performing repetitive and sequential layering as well as in particular the perforated patch design, it is ensured that the cells within the EHM do not suffer from hypoxia and are supplied with enough nutrients. Another theoretical option of generating a thickened EHM of e.g. 10 mm would be to directly cast a large volume of reconstitution mixture in one casting step. In order to obtain an EHM of 10 mm in thickness, the single reconstitution mixture would need to be around 100 mm in thickness. The cells within said mixture would need to be supplied with oxygen and nutrients over a 1 to 10 centimetre distance depending on the stage and extent of tissue compaction. As the EHM is not vascularized, the embedded cells would suffer from hypoxia induced apoptosis and necrosis in centimetre scale EHM. In order to overcome this hurdle, the inventors have developed a method to perform repetitive and sequential layering in casting moulds equipped with perforating poles (FIGS. 3 and 7), as disclosed herein. This approach is advantageous over other approaches, which do not ensure sufficient oxygen and nutrient supply.

Furthermore, it is essential that the penetrating poles install mechanical support elements to support auxotonic contractions.

Materials and Methods of Example 2

Generation of 5-layered EHM: EHM were constructed in custom-made casting moulds (FIG. 7) using a reconstitution mixture described in Tiburcy et al. (2017) and WO2015025030. After casting of the reconstitution mixture (8 mL; refer to FIG. 2) EHM compaction was observed within 3 days to less than 50% of the original reconstitution volume. After removal of the culturing medium, a second layer (comprised of 6 mL reconstitution mixture—volume may be adjusted and depends on mould design/surface area and use, and can be adapted according to EHM compaction) was pipetted into the casting mould to cover the compacted EHM from the top and the bottom. For example, 8 ml could have also been also added or a smaller volume such as 2 ml for covering a restricted area (see Example 5 for further illustration). After approximately 1 h, gelation of the newly pipetted reconstitution mixture was completed and culturing medium was added to the mould. This process was repeated until 5 layers were obtained. Reconstitution mixture volume for repetitive layering and timing depends on casting mould dimensions and stroma-cell mediated compaction of the EHM.

Generation of a hypoxia reporter line. A piggyBAC-ODD-Luc plasmid was cloned that contains firefly luciferase fused to the oxygen-dependent degradation domain (ODD) of HIF1α under control of the chicken actin promotor (CAG). Under normoxic conditions the ODD domain is rapidly degraded by the ubiquitin-proteasome system. Under hypoxia the ODD domain is stabilized leading to measurable luminescence (Hesse et al. (2014)). TC1133 iPSC were electroporated with piggyBAC-ODDLuc constructs together with a transposase vector. 48 hrs after electroporation cells were selected with increasing concentration of Neomycin (250-500-750 ug/mL) for 7 day before colonies were manually picked and expanded.

Validation of the hypoxia reporter line. Pluripotent stem cells expressing firefly luciferase fused to the oxygen-dependent degradation domain (ODD) of HIF1a under control of the chicken actin promotor (CAG) were lysed in 1× Passive lysis buffer (Dual-Luciferase® Reporter Assay Systems, Promega) with protease and phosphatase inhibitors (both Roche) after being exposed to hypoxia (5 or 1% $O_2$). Cell-containing or cell-free (lysis buffer only) lysates were mixed with Luciferase assay reagent II (Dual-Luciferase® Reporter Assay Systems, Promega) and luminescence was measured using a FlexStation 3 Multi-Mode Microplate Reader (Molecular Devices); mean±SEM; n=3:

| | Cell-free | | Cells | |
|---|---|---|---|---|
| Oxygen concentration | 21% | 21% | 5% | 1% |
| Luminescence (RLU, × 10E3) | 40 ± 4 | 216 ± 6 | 3300 ± 90 | 9380 ± 400 |

The increase in luminescence signal from the stably genetically integrated ODD-Luc reporter in response to lower oxygen concentrations demonstrated the utility of the ODD-Luc model in the sensing of hypoxia in human pluripotent stem cell models.

Bioluminescence imaging of hypoxia reporter EHM. ODD-Luc EHM were submerged in phosphate buffered saline containing 1 mg/ml XenoLight D-Luciferin (Perkin Elmer). Luminescence of EHM was imaged at 37° C. using an IVIS Lumina III system (Perkin Elmer). Luminescence is represented in grey scale in FIG. 3D. The 5-layered EHM showed less luminescence than the single-layered EHM.

Figure 4:
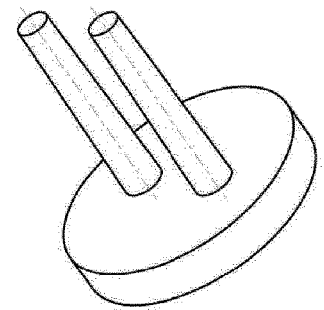
FIG. 4: Multi-well plate format for automated casting in a loop-format. A: custom-made stretchers (flexible poles fixed on a base plate) to support auxotonic contractions of engineered heart myocardium in loop format showing typical dimension of pole dimensions and arrangements. B: Multi-well plate format for automated casting, parallel culture and video-optic analysis of 48 engineered heart myocardium in loop-format with close-up view of a single well showing the cavity for casting and the flexible poles for maturation under defined mechanical loading (please refer to Tiburcy et al. 2020 for addition details)
Figure 4:
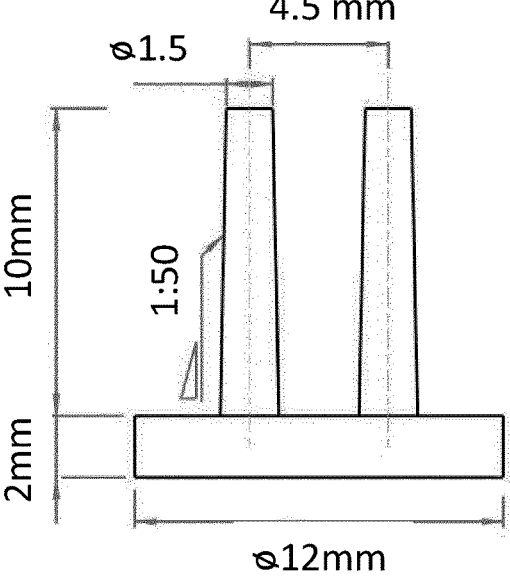
Figure 4:
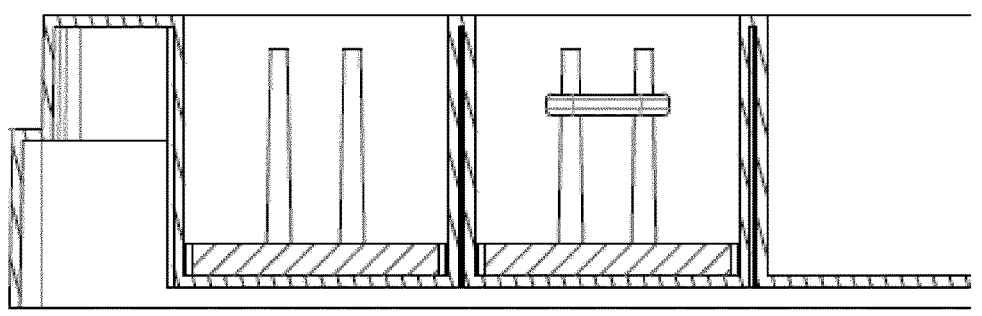
Figure 4:
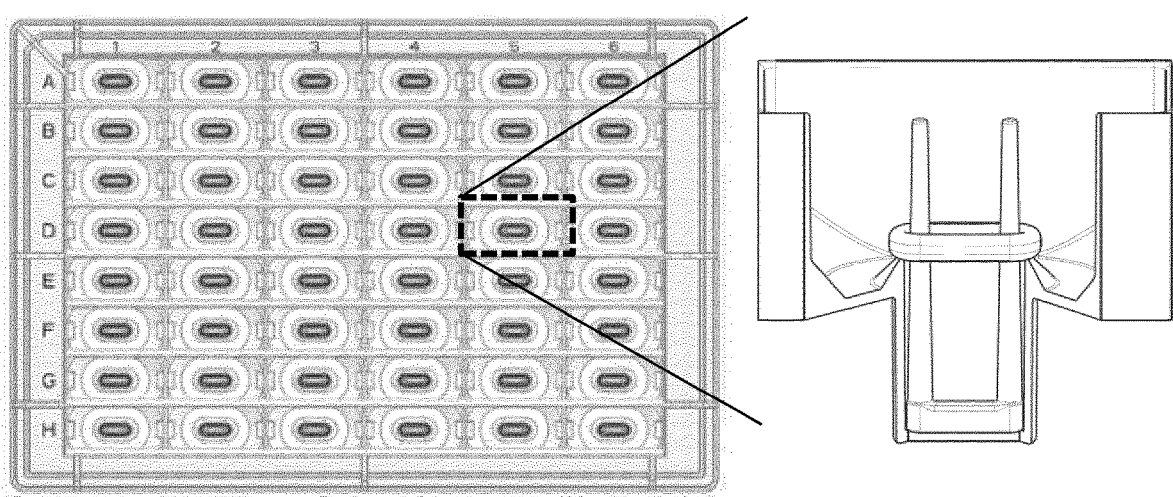
Figure 5:
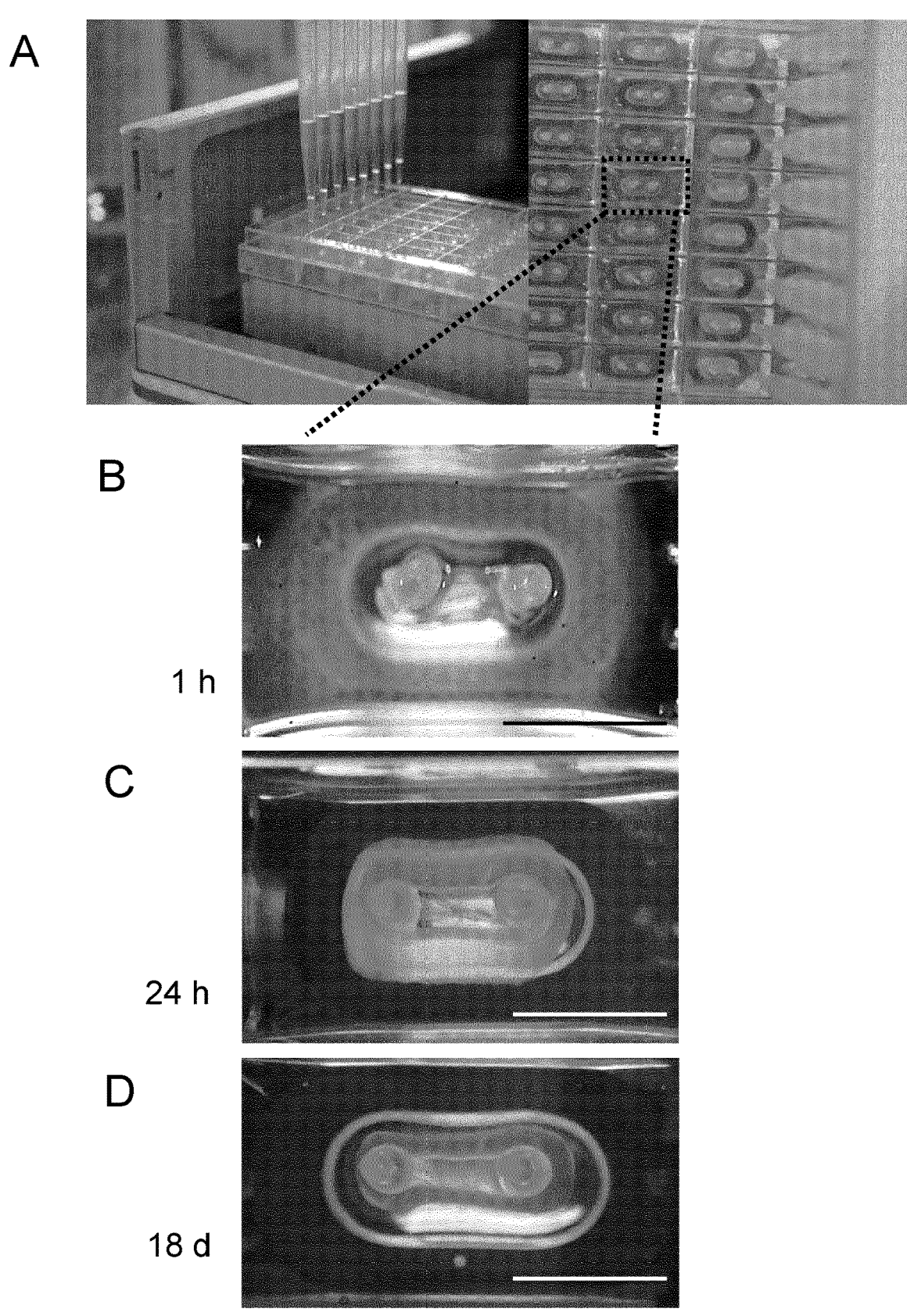
FIG. 5: EHM formation in loop-format. A: Automated casting of EHM in a multi-well plate. B: 1 hour after casting, EHM convert to a non-liquid state (collagen gelation results in an opaque appearance of the EHM reconstitution mixture) C: Notable EHM compaction and suspension on flexible poles for mechanical loading 24 hours after casting. D: EHM after completion of compaction on culture day 18 with EHM fully suspended on the flexible poles to impose bi-directional mechanical loading and to support auxotonic contractions under preloaded conditions. Scale bar: 5 mm

Example 3—Generation of EHM in Loop-Format in a Multi-Well Plate Illustrating the Condensation Process of Engineered Human Myocardium FIG. 5 provides a proof-of-principle overview of the condensation (after 1 h of gelation) and compaction (after 24 h and 18 days) of the reconstitution mixture in order to form a force-generating EHM in loop-format. For example, EHM in loop format can be generated on custom-made stretchers (flexible poles fixed on a base plate) to support auxotonic contractions of engineered human myocardium (FIG. 4A). As previously disclosed in Tiburcy et al. (2020), 48 EHMs in loop-format can be produced in parallel by using a defined multi-well plate (FIG. 4B). The multi-well plate is also further described in WO 2017/207431. The multi-well plate is characterized in that each mould is in the form of a ring channel. Each EHM is cast into a ring channel. During condensation and compaction of the reconstitution mixture, the engineered human myocardium detaches from the ring channel, moves upwards and closely wraps around the two poles.

In a first step, the reconstitution mixture was provided in the mould of the multi-well plate as described previously in Tiburcy et al. 2017 or Tiburcy et al. 2020. When the reconstitution mixture is cast into the mould, the reconstitution mixture is a viscous liquid translucent solution. After one hour of incubation at 37° C. in a humidified incubator with 5% $CO_2$, the engineered human myocardium turned opaque as the reconstitution mixture consolidated primarily by cell-independent gelation of the collagen hydrogel (refer also to Tiburcy et al. (2014), Schlick et al. (2019)). After consolidation (for e.g. 1 hour, FIG. 5B), culturing medium was added to the moulds, which provided nutrients and growth factors (see e.g. Tiburcy et al. (2017) and Tiburcy et al. (2020) for exemplary medium compositions). After culturing for e.g. 24 hours, the loop detached from the mould so that a space between the reconstitution mixture and the mould was visible. Furthermore, after 24 hours, the reconstitution mixture detached from the ring channel and closely wrapped around the two poles (FIG. 5C). The process of EHM formation around the flexible poles is a function of the stroma cell component and can further be facilitated by addition of effective concentrations of TGFb1. After engineered human myocardium are positioned on the flexible poles engineered human myocardium maintenance medium without TGFb1 was used. In the following 17 days, the mixture further condenses around the two poles as depicted in FIG. 5D and a compact and contracting engineered human myocardium develops. The poles are developed to bend in response to the EHM contractions and to pull the EHM apart to a defined resting length during the EHM relaxation phase to simulate the natural auxotonic contraction cycles of the heart.

Example 4—Excitability of Engineered Heart Muscle (EHM)

Figure 6:
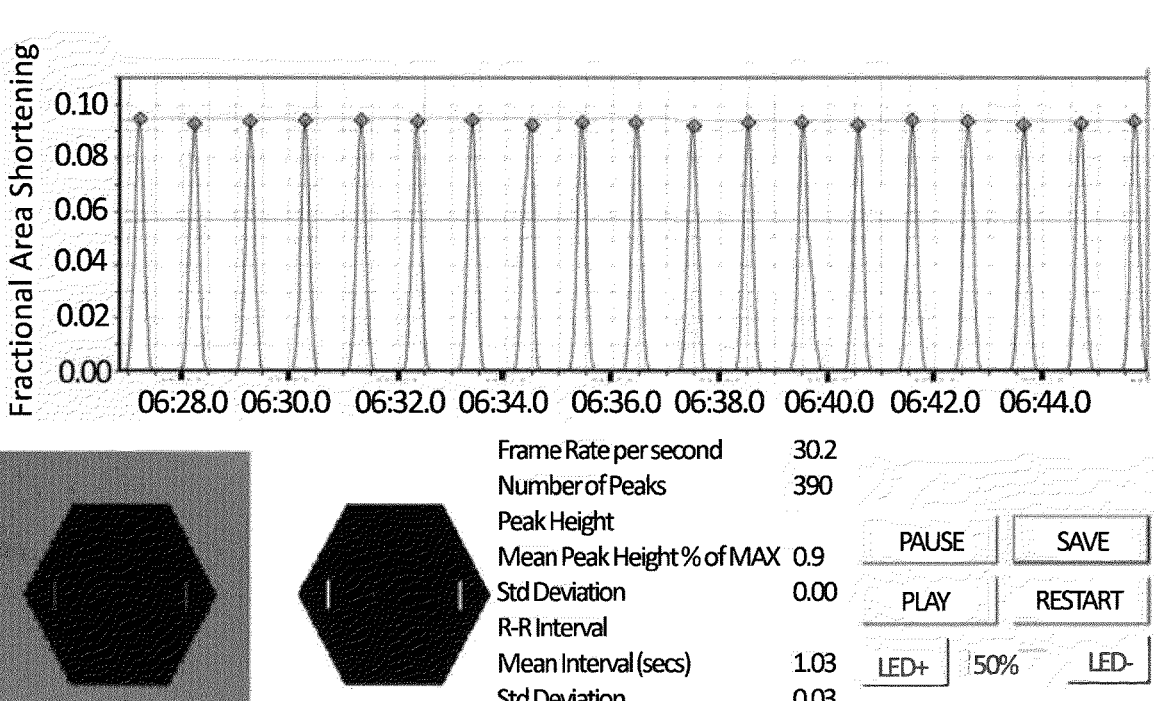
FIG. 6: A: Video-optical Analysis of EHM contraction with or without stimulation. A: Screenshot of the custom-made video-optic analysis tool for functional phenotyping of EHM by fractional area change (FAC) measurements. B: Device for electrical stimulation of EHM to induce contractions at a defined rate. Electrical field stimulation is increased until EHM are induced to contract at a defined beating rate (to typically 2 V/cm). (C) Alternatively, local point stimulation with electrodes touching the EHM can be applied to induce synchronous contractions of EHM for FAC analyses.
Figure 6:
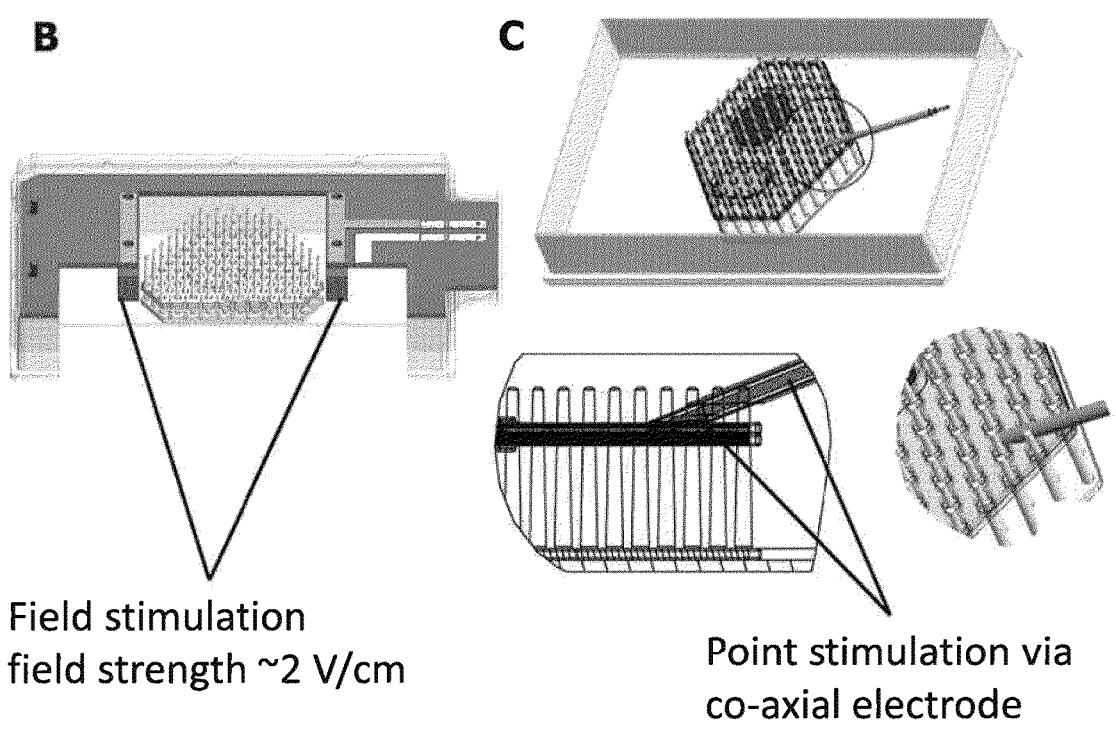

Excitation of cardiomyocytes typically leads to a contraction of these cells. In order to measure the contraction within EHMs, Tiburcy et al. (2017) described the fractional area change (FAC) of the patch upon contraction. FAC is a video-optical measurement, wherein the surface area of the patch is compared in a non-contracted and contracted state. By using said videooptic analysis tool, EHMs can be phenotyped and compared. FIG. 6A depicts a custom-made video-optic analysis tool in order to facilitate the measurement. FIG. 6B shows a device for electrical stimulation of EHM to induce contractions at a defined rate. Electrical field stimulation strength is increased (to typically 2 V/cm$^2$) until EHM are induced to contract at a defined beating rate (typically controlled at 0.1-3 Hz). Alternatively, local point stimulation with electrodes touching the EHM can be applied to induce synchronous contractions of EHM at a desired beating rate for FAC analyses (FIG. 6C).

FAC (fraction area change) is measured by comparing the EHM surface area upon video-optic imaging in maximal systole (maximally contracted state) and maximal diastole (maximally relaxed state). The change in surface area is recorded as function of time.

Example 5—Various Geometries for Multilayer Engineered Heart Muscle Designs

Figure 7:
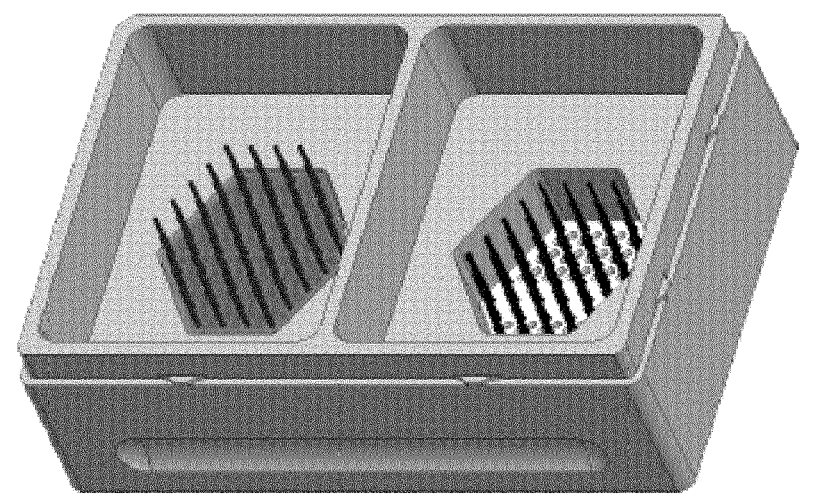
FIG. 7: Multilayer EHM casting moulds in patch format. A: Custom-designed casting mould with two recesses designed to hold a baseplate with poles (bottom) and culture medium (top). In the left recess with flexible poles, a compacted reconstitution mixture is depicted for clarification. Layers are stacked on top, inserted below or formulated around the first layer. B: Cross section thought recess in casting mould with vertically, perforating poles (grey and white) with layered EHM in black. C: Examples for pole designs with and without pole thickness gradient; note that by design of the poles (elastic properties, diameter or geometry of poles) homogeneous (no gradient, all poles are 0.9 mm in diameter in this example) and heterogeneous (example of a top to bottom gradient, poles have a diameter from 1.1 mm to 0.7 mm from top to bottom with 0.1 mm steps) mechanical loading imposed on the EHM can be controlled. D: Example of an EHM, which developed either isotropic (no gradient; wherein the poles have the same diameter) or anisotropic (vertical gradient; wherein the poles a gradient in diameter) contraction patterns. Contraction patterns are analysed by comparing the FAC of the upper and the lower part of the EHM. When all poles have the same diameter, the upper and the lower part of the EHM showed a similar contraction of around 1% FAC. In contrast, a vertical gradient lead to an increase in contraction force of the upper part to around 1.2% FAC (larger pole diameter) and lead to a decrease in contraction force of the lower part to around 0.7% FAC (smaller pole diameter).
Figure 7:
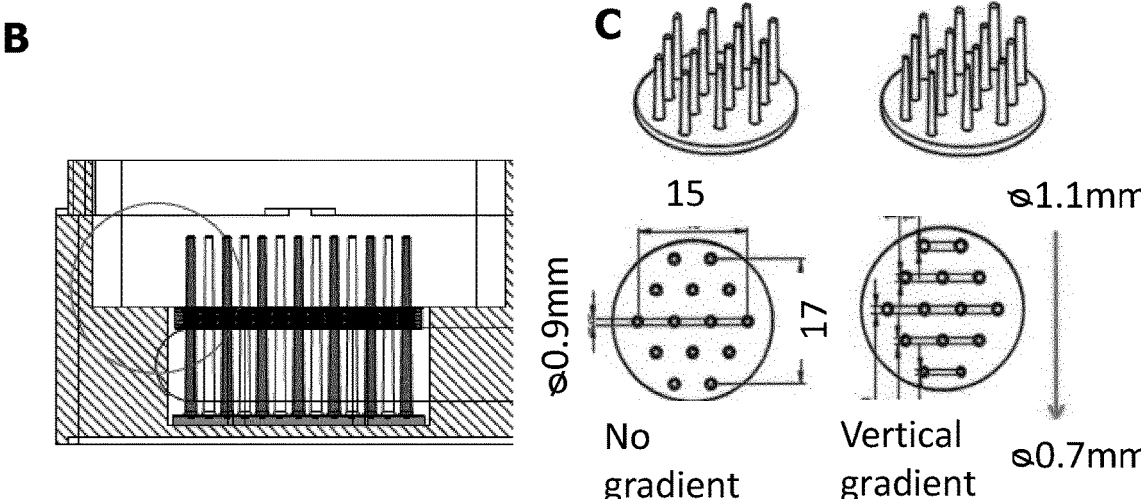
Figure 7:
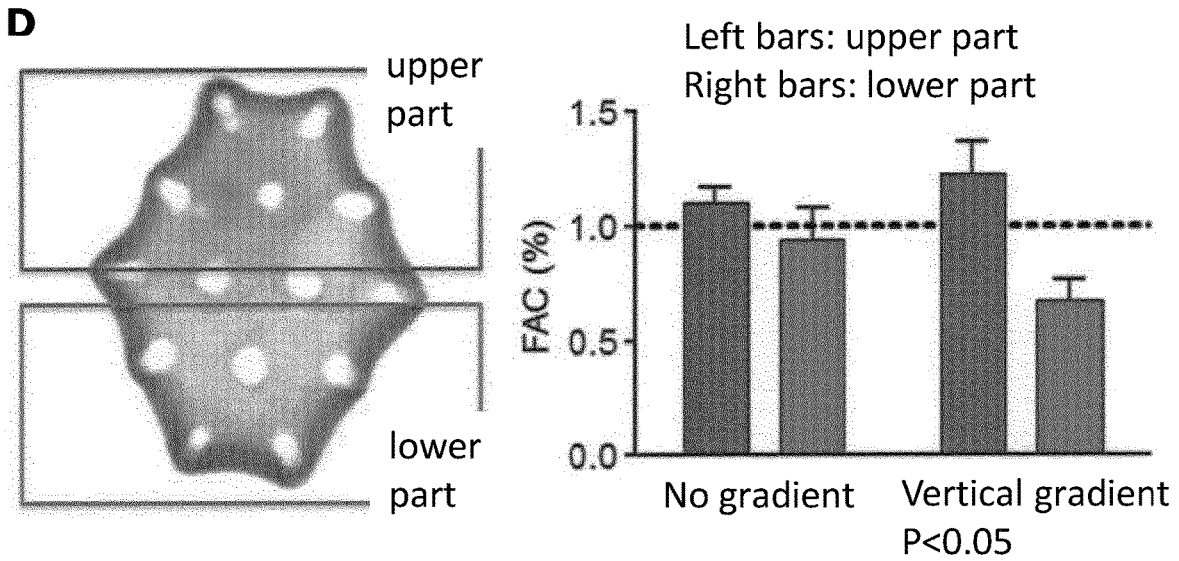
Figure 8:
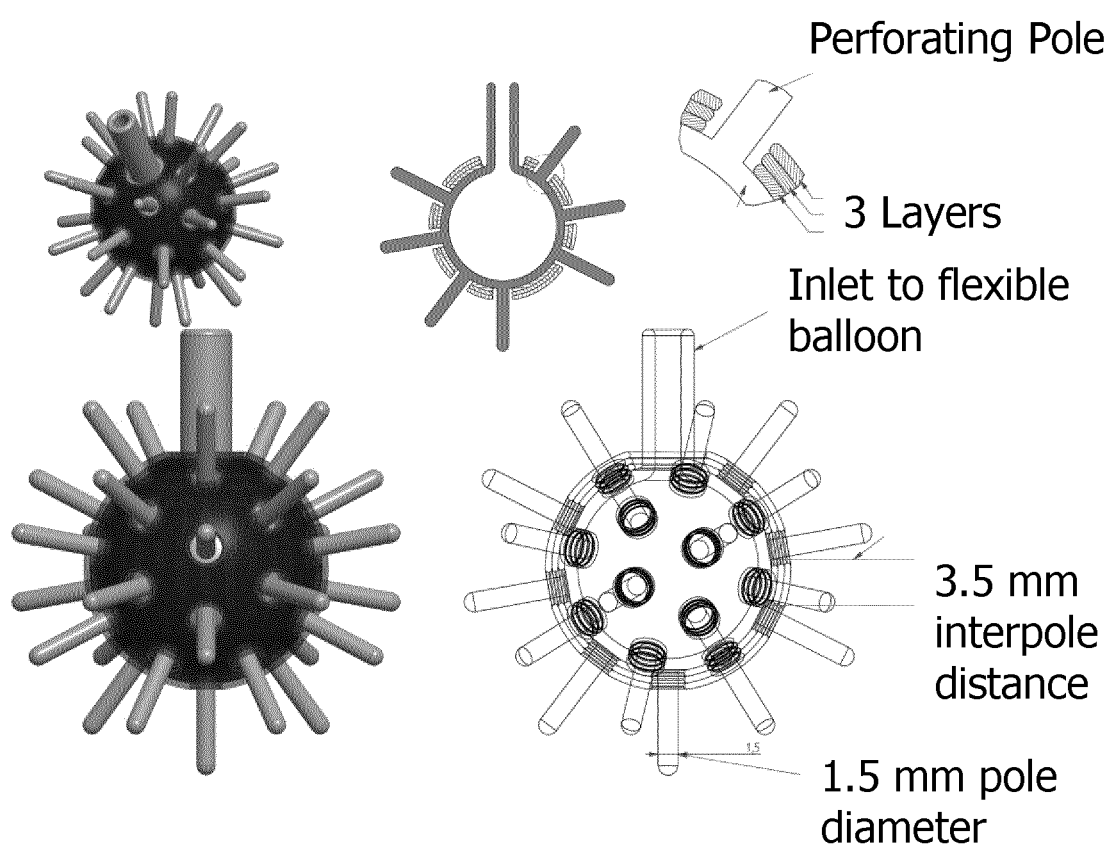
FIG. 8: Multilayer engineered heart muscle (MEHM) in variable geometries. Examples for multilayer engineered heart muscle (MEHM) designs. MEHM can be produced in pouch (A), cylinder (B), and patch formats (C) with variable thickness and x-y-dimensions (exemplified in patch format in C). In the MEHM pouch geometry (A), MEHM are cast in a circular or spherical mold with a central element (solid or flexible for biomechanical loading of the compacting EHM; similar as described in Zimmermann W H, Yildirim Y, Eschenhagen T: Pouch-like engineered heart muscle tissue. WO2008058917 and Yildirim et al. (2007) Circulation). In the depicted example, interpole distance is 3.5 mm with a pole diameter of 1.5 mm in analogy to a preferred embodiment described for EHM patches (FIG. 7). Poles can be adapted in size, geometry, and interpole distance as needed to create optimal loading and perforation for oxygen and nutrient supply. In case of the cylinder geometries (B), poles can be fabricated to point inwards or outwards and with wholes preferably in the cylinders with the outwards pointing poles. Layering can be supported by centrifugal forces (>2 g; "spin-coating") induced by controlled rotation. (C) Heterogeneous ("patch-in-patch") multi-layer strategies either by positioning of a perforated patch assembly is demonstrated, including the perforating pole element, into a new mould to accommodate additional layering (C1) or by making use of inserts to isolate a defined casting volume within a larger casting mold design (C2). This allows for a free design of MEHM with variable thickness and xy-dimensions to facilitate the fabrication of a patient heart matched/individualized patch.
Figure 8:
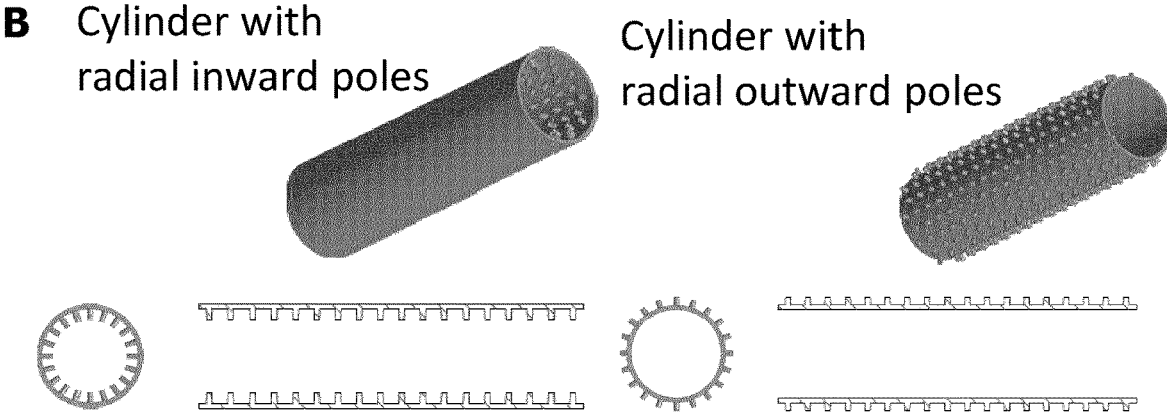
Figure 8:
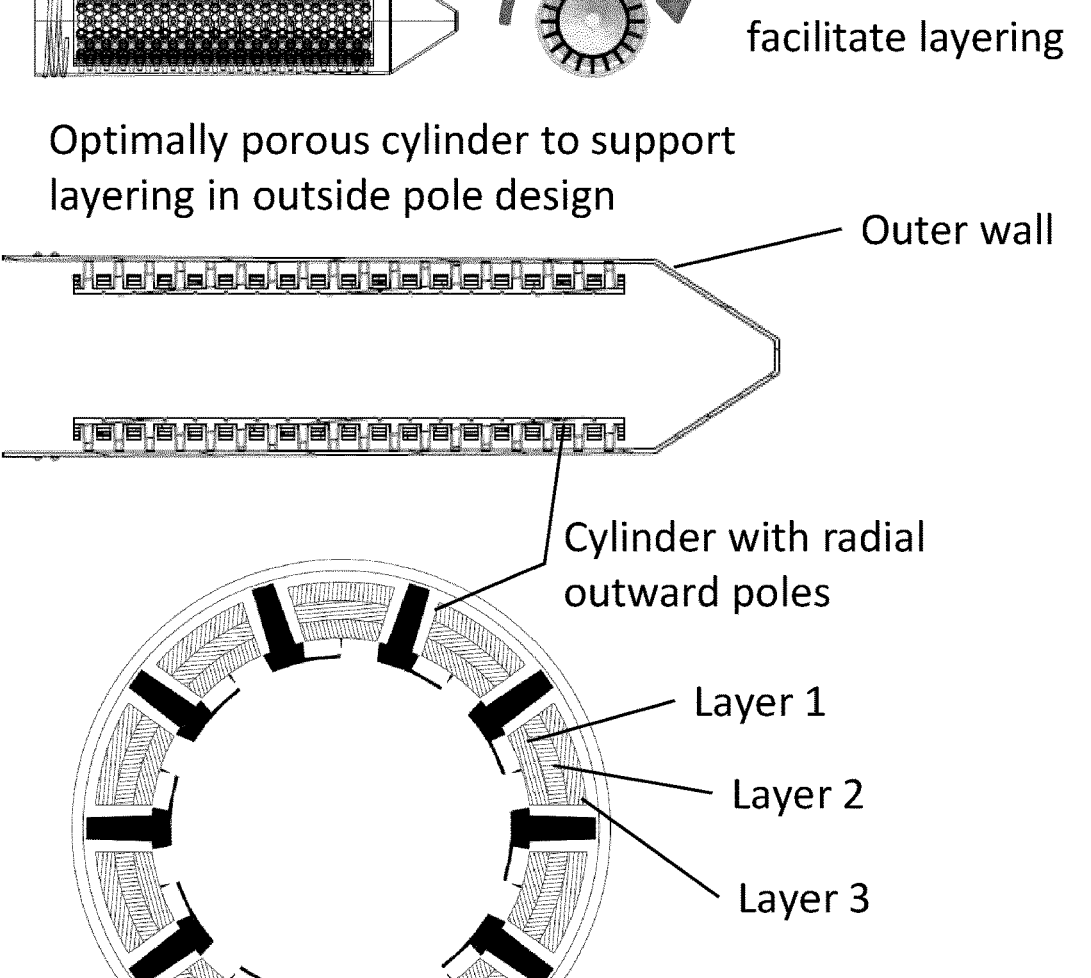
Figure 8:
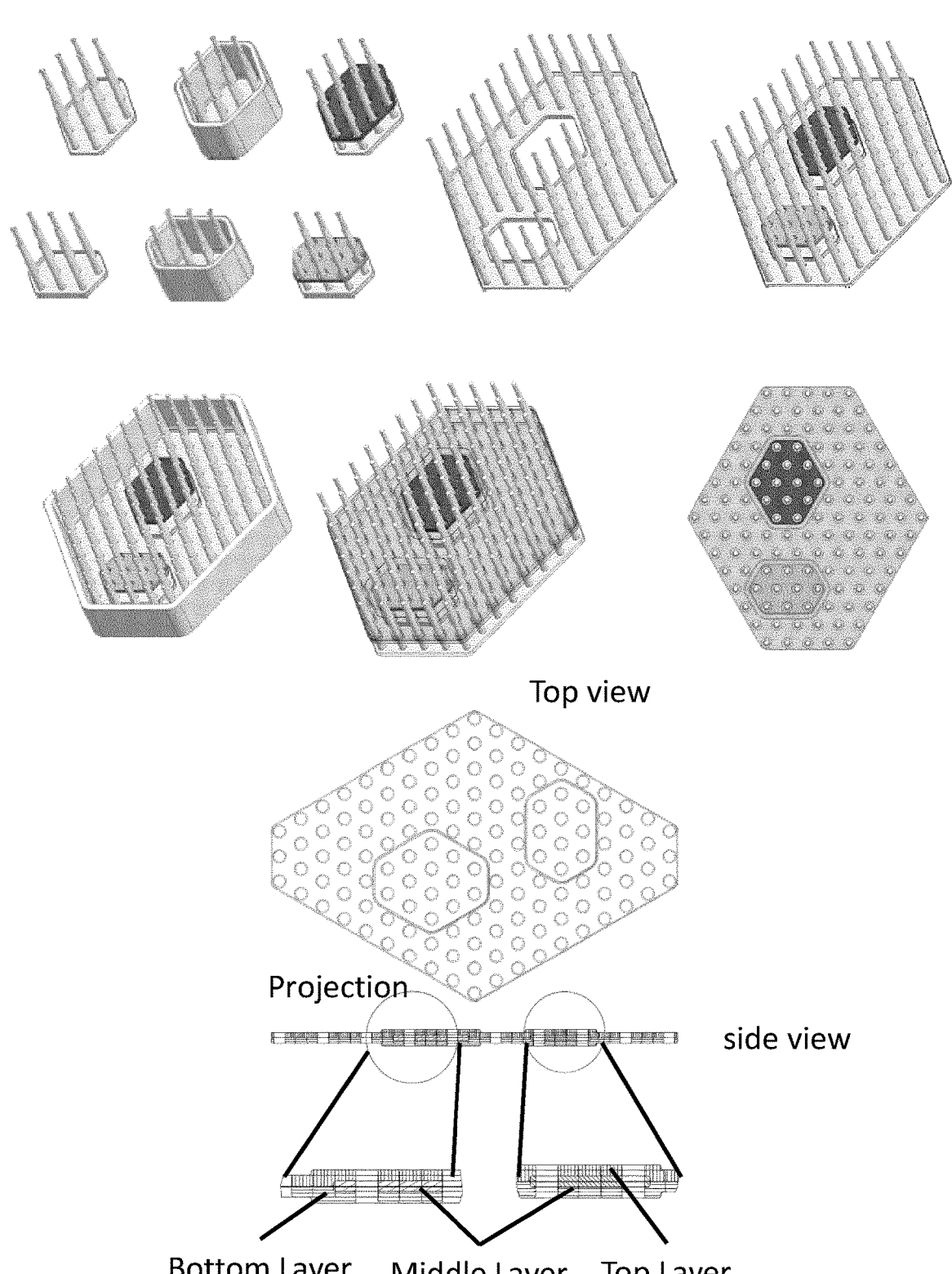
Figure 8:
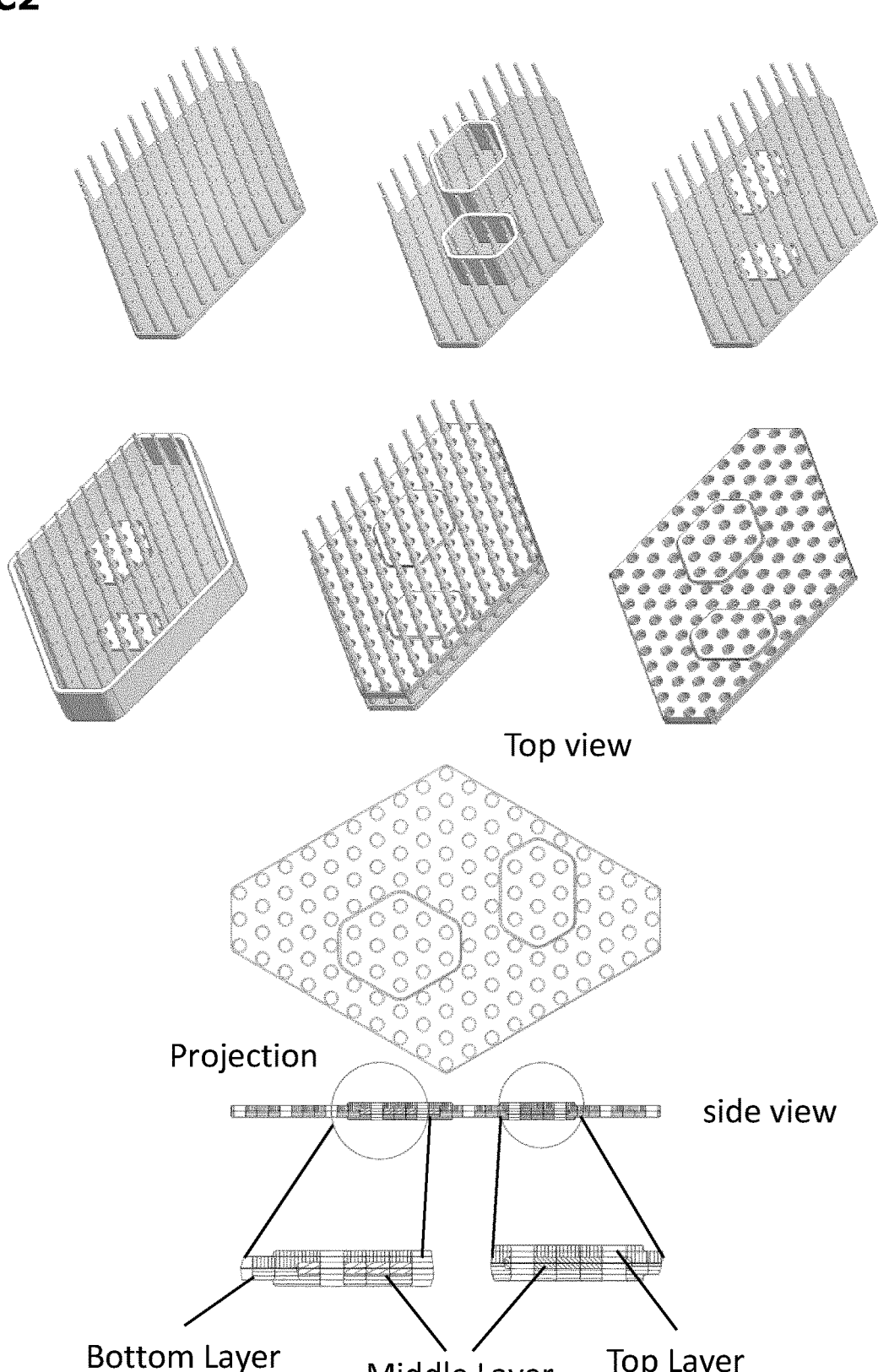

In general, MEHM can be generated in various three-dimensional shapes. The general principle is a mould equipped with perforating poles with homogeneous or heterogeneous shapes and dimensions to (i) impose mechanical resistance on the forming EHM and (ii) to create perforating channels for nutrient and oxygen supply. In the EHM pouch geometry (as depicted in FIG. 8A), EHM are cast in a circular or spherical mold with a central element (solid or flexible for biomechanical loading of the compacting EHM; similar as described in Zimmermann W H, Yildirim Y, Eschenhagen T: Pouch-like engineered heart muscle tissue. WO2008058917 and Yildirim et al. (2007) Circulation). In contrast to WO2008058917 and to reliably create, e.g. >1 mm, thick pouches with controlled muscle formation, perforating poles are created on top of the central element. In the depicted example of FIG. 8A, interpole distance is 3.5 mm with a pole diameter of 1.5 mm in analogy to a preferred embodiment described for EHM patches (FIG. 7). Poles can be adapted in size, geometry, and interpole distance as needed to create optimal loading and perforation for oxygen and nutrient supply.

In a further example, the MEHM can also have the form of a cylinder. In case of the cylinder geometries (FIG. 8B), poles can be fabricated to point inwards or outwards so that the reconstitution mixture is perforated. A key advantage of a cylindrical shaped EHM is that many EHMs can be produced on parallel using up comparatively little space. After completion of the cylindrical MEHM production, the MEHM can be sliced open on one side in order to obtain a patch or left intact to yield a MEHM cylinder/tube of desired dimensions. The MEHM dimensions can be scaled by freely adapting the circumference of the inner and/or outer mould cylinders with poles extending/radiating inwards or outwards. Moulds in the form of cylinders with perforating poles are produced for example by prototype 3D-printing to fit into a container. Said container then supplies the outer wall for cylindrical EHM production (for example 50 ml polypropylene or glass tube). The container is filled with sufficient reconstitution mixture to coat the inner or outer side of the cylinder. Layering can be supported by centrifugal forces (>2 g; "spin-coating") induced by controlled rotation. Tubular/cylindrical EHM generated in cylindrical, longitudinally spinning bioreactors should be performed at >2 g. Inserted tubular stretcher contain radially extruding poles to perforate EHM. Centrifugal force experienced by EHM can be controlled by adjusting rotation velocity to mimic increasing diastolic pressure during maturation. Furthermore, centrifugation ensures an equal spreading of the reconstitution mixture in order to ensure an equal thickness of the EHM. Equal coating in an outward radiating cylinder design can be further improved by using an inner mould cylinder with wholes to allow for equal distribution of the reconstitution mixture during a spin coating procedure. After coating and gelation, culturing medium can be added to facilitate compaction. The multilayering can be repeated until the desired layer composition is achieved. Layers can be added to the top and/or the bottom of the previous reconstitution mixture.

FIG. 8C demonstrates a further example of MEHM design. FIG. 8C shows heterogeneous ("patch-in-patch") multilayer strategies to create MEHM with variable thicknesses according to the needed in the production of individualized MEHM for example for clinical use in heart repair: Firstly, by positioning of a perforated patch assembly into a new mould to accommodate additional layering (C1), and secondly by making use of inserts to isolate a defined casting volume within a larger casting mold design (C2). This allows for a free design of EHM with (i) variable thickness and (ii) xy-dimensions to facilitate the fabrication of a patient heart matched/individualized patch. The described elements can be prepared by prototype 3D printing as described in Tiburcy et al. (2017), cast molding, or other suitable engineering methods. Moulds are typically created from teflon, PDMS, or agarose using milling or cast molding whereas the perforated pole assemblies are typically printed using 3D printing, for example with a Connex350 (Stratasys) 3D printer, or by cast molding. For 3D printing, a biocompatible MED610 polymer for stiff components (for example base plate in case of the perforated patch design or the outer mould elements of the pouch-design) in combination with a TangoBlack polymer for the flexible elements, such as the poles and cylinders, can be applied.

Tables

TABLE 1

Composition of the serum-free supplement 'B27 minus insulin' (50× concentration, liquid) 20 ml of 'B27 minus insulin' per 500 ml medium corresponds to 4% B27 minus insulin (v/v):

| Ingredients | concentration in B27 µg/ml | final concentration in medium µg/ml |
|---|---|---|
| Bovine serum albumin, fraction V IgG free, fatty acid poor | 125000 | 5000 |
| Catalase | 125 | 5 |
| Glutathion reduced | 50 | 2 |
| Superoxide Dismutase | 125 | 5 |
| Humanes Holo-Transferrin | 250 | 10 |
| T3 (triodo-I-thyronine) | 0.1 | 0.004 |
| L-carnitine-HCl | 100 | 4 |
| Ethanolamine | 50 | 2 |
| D+-galactose | 750 | 30 |
| Putrescine | 805 | 32.2 |
| sodium-Selenite | 0.625 | 0.0250 |

TABLE 1-continued

Composition of the serum-free supplement 'B27 minus insulin'
(50× concentration, liquid) 20 ml of 'B27 minus insulin'
per 500 ml medium corresponds to 4% B27 minus insulin (v/v);

| Ingredients | concentration in B27 μg/ml | final concentration in medium μg/ml |
|---|---|---|
| Corticosterone | 1 | 0.04 |
| linoleic acid | 50 | 2 |
| linolenic acid | 50 | 2 |
| Progesterone | 0.315 | 0.0126 |
| Retinylacetate | 5 | 0.2 |
| DL-alpha tocopherole (Vit E) | 50 | 2 |
| DL-alpha tocopherol Acetate | 50 | 2 |
| Biotin | 125 | 5 |

LIST OF REFERENCES

EP2099508

EP20188364.2

EP2842581 A1

EP2840132 B1

WO 2007/054286

WO 2008/058917 A1

WO 2015/025030

WO 2017/207431

Bao X, et al. Long-term self-renewing human epicardial cells generated from pluripotent stem cells under defined xeno-free conditions. Nat Biomed Eng. 2016; 1; or Bao X, et al. Directed differentiation and long-term maintenance of epicardial cells derived from human pluripotent stem cells under fully defined conditions. Nat Protoc. 2017 September; 12(9):1890-1900.

Brewer, G. J., Torricelli, J. R., Evege, E. K. and Price, P. J. (1993), Optimized survival of hippocampal neurons in B27-supplemented Neurobasal™, a new serum-free medium combination. J. Neurosci. Res., 35: 567-576.

Fujita N, Duerinekx A J, Higgins C B. Variation in left ventricular regional wall stress with cine magnetic resonance imaging: normal subjects versus dilated cardiomyopathy. Am Heart J. 1993 125:1337-45.

Hanses, U., Kleinsorge, M., Roos, L., Yigit, G., Li, Y., Barbarics, B., El-Battrawy, I., Lan, H., Tiburcy, M., Hindmarsh, R., et al. (2020). Intronic CRISPR Repair in a Preclinical Model of Noonan Syndrome-Associated Cardiomyopathy. Circulation Hesse A R, Levent E, Zieseniss A, Tiburcy M, Zimmermann W H, Katschinski D M (2014) Lights on for HIF-1α: Genetically Enhanced Mouse Cardiomyocytes for Heart Tissue Imaging. Cell Physiol Biochem. 34:455-462

Hynes R O, Naba A. Overview of the matrisome—an inventory of extracellular matrix constituents and functions. Cold Spring Harb Perspect Biol. 2012; 4(1): a004903.

Ieda M, Fu J D, Delgado-Olguin P, Vedantham V, Hayashi Y, Bruneau B G, Srivastava D. Direct reprogramming of fibroblasts into func-tional cardiomyocytes by defined factors. Cell. 2010 Aug. 6; 142(3):375-86. Iyer D, et al. Robust derivation of epicardium and its differentiated smooth muscle cell progeny from human pluripotent stem cells. Development. 2015 Apr. 15; 142(8):1528-41;

Iyer R K, Radisic M, Cannizzaro C, Vunjak-Novakovic G. Synthetic oxygen carriers in cardiac tissue engineering. Artif Cells Blood Substit Immobil Biotechnol. 2007; 35(1):135-48.

Kawel N, Turkbey E B, Carr J J, Eng J, Gomes A S, Hundley W G, Johnson C, Masri S C, Prince M R, van der Geest R J, Lima J A, Bluemke D A. Normal left ventricular myocardial thickness for middle-aged and older subjects with steady-state free precession cardiac magnetic resonance: the multi-ethnic study of atherosclerosis. Circ Cardiovasc Imaging. 2012 July; 5(4):500-8.

Kensah, G., Roa Lara, A., Dahlmann, J., Zweigerdt, R., Schwanke, K., Hegermann, J., Skvorc, D., Gawol, A., Azizian, A., Wagner, S., et al. (2013). Murine and human pluripotent stem cell-derived cardiac bodies form contractile myocardial tissue in vitro. Eur Heart J 34, 1134-1146

Mills, R. J., Parker, B. L., Quaife-Ryan, G. A., Voges, H. K., Needham, E. J., Bornot, A., Ding, M., Andersson, H., Polla, M., Elliott, D. A., et al. (2019). Drug Screening in Human PSC-Cardiac Organoids Identifies Pro-proliferative Compounds Acting via the Mevalonate Pathway. Cell Stem Cell 24, 895-907 e896.

Mouw J K, Ou G, Weaver V M. Extracellular matrix assembly: a multiscale deconstruction. Nat Rev Mol Cell Biol. 2014; 15(12):771-785. doi:10.1038/nrm3902

Mulieri L A, Hasenfuss G, Leavitt B, Allen P D, Alpert N R. Altered myocardial force-frequency relation in human heart failure. Circulation. 1992 May; 85(5):1743-50.

Nam Y J, Song K, Luo X, Daniel E, Lambeth K, West K, Hill J A, DiMaio J M, Baker L A, Bassel-Duby R, Olson E N. Reprogramming of human fibroblasts toward a cardiac fate. Proc Natl Acad Sci USA. 2013 Apr. 2; 110(14):5588-93.

Nowosielski M, Schocke M, Mayr A, Pedarnig K, Klug G, Köhler A, Bartel T, Müller S, Trieb T, Pachinger O, Metzler B. Comparison of wall thickening and ejection fraction by cardiovascular magnetic resonance and echocardiography in acute myocardial infarction. J Cardiovasc Magn Reson. 2009 Jul. 9; 11(1):22.

Naito, H., Melnychenko, I., Didie, M., Schneiderbanger, K., Schubert, P., Rosenkranz, S., Eschenhagen, T., and Zimmermann, W. H. (2006). Optimizing engineered heart tissue for therapeutic applications as surrogate heart muscle. Circulation 114, 172-78

O'Leary L E, Fallas J A, Bakota E L, Kang M K, Hartgerink J D. Multi-hierarchical self-assembly of a collagen mimetic peptide from triple helix to nanofibre and hydrogel. Nat Chem. 2011 Aug. 28; 3(10):821-8. doi: 10.1038/nchem.1123. PMID: 21941256.

Pislaru C, Urban M W, Pislaru S V, Kinnick R R, Greenleaf J F. Viscoelastic properties of normal and infarcted myocardium measured by a multifrequency shear wave method: comparison with pressure-segment length method. Ultrasound Med Biol. 2014 August; 40(8):1785-95

Radisic M, Deen W, Langer R, Vunjak-Novakovic G. Mathematical model of oxygen distribution in engineered cardiac tissue with parallel channel array perfused with culture medium containing oxygen carriers. Am J Physiol Heart Circ Physiol. 2005 March; 288(3):H1278-89

Riegler, J., Tiburcy, M., Ebert, A., Tzatzalos, E., Raaz, U., Abilez, O. J., Shen, Q., Kooreman, N. G., Neofytou, E., Chen, V. C., et al. (2015). Human Engineered Heart Muscles Engraft and Survive Long Term in a Rodent Myocardial Infarction Model. Circulation research 117, 720-730

Ronaldson-Bouchard, K., Ma, S. P., Yeager, K., Chen, T., Song, L., Sirabella, D., Morikawa, K., Teles, D., Yazawa, M., and Vunjak-Novakovic, G. (2018). Advanced maturation of human cardiac tissue grown from pluripotent stem cells. Nature 556, 239-243

Rump, J., Klatt, D., Braun, J., Warmuth, C. and Sack, I. (2007), Fractional encoding of harmonic motions in MR elastography. Magn. Reson. Med., 57: 388-395

Schlick S F, Spreckelsen F, Tiburcy M, Iyer L M, Meyer T, Zelarayan L C, Luther S, Parlitz U, Zimmermann W H, Rehfeldt F. Agonistic and antagonistic roles of fibroblasts and cardiomyocytes on viscoelastic stiffening of engineered human myocardium. Prog Biophys Mol Biol. 2019 July; 144:51-60.

Song K, Nam Y J, Luo X, Qi X, Tan W, Huang G N, Acharya A, Smith C L, Tallquist M D, Neilson E G, Hill J A, Bassel-Duby R, Olson E N. Heart repair by reprogramming non-myocytes with cardiac transcription factors. Nature. 2012 May 13; 485(7400):599-604.

Soong P L, Tiburcy M, and Zimmermann (2012) Cardiac differentiation of human embryonic stem cells and their assembly into engineered heart muscle. Curr Protoc Cell Biol. Chapter 23:Unit23.8.

Stoker M E, Gerdes A M, May J F. Regional differences in capillary density and myocyte size in the normal human heart. Anat Rec. 1982 February; 202(2):187-91.

Tulloch N L, Muskheli V, Razumova M V, et al. (2011) Growth of engineered human myocardium with mechanical loading and vascular coculture. Circ Res 109(1):47-59.

Tiburcy M, Meyer T, Soong P L, Zimmermann W H. Collagen-based engineered heart muscle. Methods Mol Biol. 2014; 1181:167-76. doi: 10.1007/978-1-4939-1047-2_15. PMID: 25070336.

Tiburcy, M., Hudson, J. E., Balfanz, P., Schlick, S., Meyer, T., Chang Liao, M. L., Levent, E., Raad, F., Zeidler, S., Wingender, E., et al. (2017). Defined Engineered Human Myocardium With Advanced Maturation for Applications in Heart Failure Modeling and Repair. Circulation 135, 1832-1847.

Tiburcy, M., Meyer, T., Liaw, N. Y., and Zimmermann, W. H. (2020). Generation of Engineered Human Myocardium in a Multi-well Format. STAR Protocols.

Wiegerinck R F, Cojoc A, Zeidenweber C M, Ding G, Shen M, Joyner R W, Fernandez J D, Kanter K R, Kirshbom P M, Kogon B E, Wagner M B. Force frequency relationship of the human ventricle increases during early postnatal development. Pediatr Res. 2009; 65:414-419.

Weinberger F, Breckwoldt K, Pecha S, et al. (2016) Cardiac repair in guinea pigs with human engineered heart tissue from induced pluripotent stem cells. Sci Transl Med 8(363):363ra148.

Witty A D, Mihic A, Tam R Y, et al. Generation of the epicardial lineage from human pluripotent stem cells. Nat Biotechnol. 2014; 32(10):1026-1035;

Yildirim Y, Naito H, Didié M, Karikkineth B C, Biermann D, Eschenhagen T, Zimmermann W H. Development of a biological ventricular assist device: preliminary data from a small animal model. Circulation. 2007 Sep. 11; 116(11 Suppl):I16-23.

Zhang, D., Shadrin, I. Y., Lam, J., Xian, H. Q., Snodgrass, H. R., and Bursac, N. (2013). Tissue-engineered cardiac patch for advanced functional maturation of human ESC-derived cardiomyocytes. Biomaterials 34, 5813-5820

Zimmermann W H, Melnychenko I, Wasmeier G, et al. (2006) Engineered heart tissue grafts improve systolic and diastolic function in infarcted rat hearts. Nat Med 12(4): 452-8.

The invention claimed is:

1. A method of manufacturing a multilayer engineered heart muscle (MEHM), the method comprising the steps of:
   (i) providing a liquid reconstitution mixture in a mould, wherein said reconstitution mixture is perforated by at least two poles,
   wherein said reconstitution mixture comprises (a) collagen, (b) a cellular mixture of cardiac myocytes and non-myocytes and (c) a suitable reconstitution medium, whereby said reconstitution mixture undergoes gelation in the mould,
   (ii) culturing the mixture obtained by step (i) in said mould in a suitable culturing medium, whereby the reconstitution mixture compacts in the mould;
   (iii) a) adding a further liquid reconstitution mixture as defined in step (i) from the top and/or from the bottom to the compacted reconstitution mixture obtained by step (ii) whereby said further liquid reconstitution mixture undergoes gelation, followed by culturing under the same conditions as in step ii), whereby said further reconstitution mixture compacts in the mould; or
      b) transferring the compacted reconstitution mixture obtained by step (ii) into a different mould, wherein said reconstitution mixture is perforated by at least two poles, followed by carrying out step (iii) a) in said different mould;
   thereby obtaining a multilayer engineered heart muscle (MEHM), and
   (iv) optionally culturing the MEHM of step (iii) in said mould in a suitable maturating medium,
   wherein the MEHM is capable of contracting,
   wherein the MEHM is from 0.7 mm to 30 mm in thickness, and
   wherein the MEHM has an interpole distance from 0.1 mm to 5 mm.

2. The method of claim 1, wherein an ability of the MEHM to contract is assessed by visual inspection.

3. The method of claim 1, wherein the non-myocyte cells are selected from one or more of the group consisting of stromal cells, endothelial cells, smooth muscle cells, and mesenchymal stem cells.

4. The method of claim 1, wherein the MEHM has a form of a patch, a pouch or a cylinder.

5. The method of claim 1, wherein in the gelation in step (i) the reconstitution mixture is opaque.

6. The method of claim 1, wherein step (iii)a) or step (iii)b) is repeated 2-200 times.

7. A multilayer engineered heart muscle (MEHM) obtained by the method according to claim 1.

8. A multilayer engineered heart muscle (MEHM), comprising
   (a) collagen and
   (b) a cellular mixture of cardiac myocytes and non-myocytes,
   wherein the MEHM comprises at least 2 layers, and
   wherein the MEHM is from 0.7 mm to 30 mm in thickness, and
   wherein the MEHM has an interpole distance from 0.1 mm to 5 mm.

9. The MEHM of claim 8,
   wherein the MEHM has been generated by a repetitive and sequential layering method,
   wherein the MEHM originates from 2-200 layers, and
   wherein the layers have been merged to each other and thereby expand the MEHM thickness.

10. The MEHM of claim 8, wherein the cardiac myocytes in the MEHM are sufficiently supplied with oxygen.

11. An in vitro manufacture method of an engineered human myocardium, comprising:

assessing a three-dimensional shape of a myocardial defect specific to a patient;

manufacturing a MEHM according to the method of claim 1, the MEHM having a three-dimensional shape that matches the three-dimensional shape of the myocardial defect specific to the patient.

12. A method of repairing a heart of a patient, comprising repairing the heart of the patient using the multilayer EHM (MEHM) obtained by the method according to claim 1.

13. The method of claim 1, wherein the MEHM is from 0.9 mm to 20 mm in thickness.

14. The method of claim 1, wherein the poles have a diameter of 0.5 to 3 mm.

\* \* \* \* \*